(12) United States Patent
Biediger et al.

(10) Patent No.: US 10,246,451 B2
(45) Date of Patent: Apr. 2, 2019

(54) PROPIONIC ACID DERIVATIVES AND METHODS OF USE THEREOF

(71) Applicants: Ronald J. Biediger, Houston, TX (US); Michele A. Benish, The Woodlands, TX (US); Robert V. Market, Pearland, TX (US); Michael M. Savage, Pearland, TX (US); Brandon M. Young, Germantown, TN (US)

(72) Inventors: Ronald J. Biediger, Houston, TX (US); Michele A. Benish, The Woodlands, TX (US); Robert V. Market, Pearland, TX (US); Michael M. Savage, Pearland, TX (US); Brandon M. Young, Germantown, TN (US)

(73) Assignee: Aviara Pharmaceuticals, Inc., Houston, TX (US)

( * ) Notice: Subject to any disclaimer, the term of this patent is extended or adjusted under 35 U.S.C. 154(b) by 0 days.

(21) Appl. No.: 15/497,416

(22) Filed: Apr. 26, 2017

(65) Prior Publication Data

US 2018/0312498 A1    Nov. 1, 2018

(51) Int. Cl.
| | | |
|---|---|---|
| *C07D 213/75* | (2006.01) | |
| *C07D 417/12* | (2006.01) | |
| *A61K 31/44* | (2006.01) | |

(52) U.S. Cl.
CPC ......... *C07D 417/12* (2013.01); *C07D 213/75* (2013.01)

(58) Field of Classification Search
None
See application file for complete search history.

(56) References Cited

U.S. PATENT DOCUMENTS 6,972,296 B2 * 12/2005 Biediger .............. C07D 213/75
514/349

* cited by examiner

*Primary Examiner* — Zinna Northington Davis
(74) *Attorney, Agent, or Firm* — Benjamin Aaron Adler

(57) ABSTRACT

Provided herein are compounds and pharmaceutical compositions of formula I

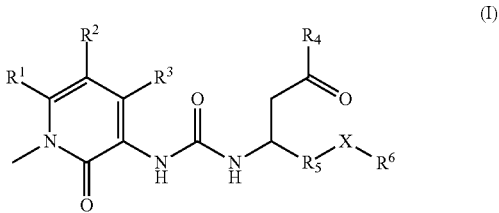

where $R^1$, $R^2$, $R^3$, $R^4$, $R^5$, X and $R^6$ are as described herein. Also provided pharmaceutically acceptable salts or stereoisomer(s) of these compounds. In addition methods are provided for antagonizing the action of an α4-integrin to treat various pathophysiological conditions.

14 Claims, No Drawings

PROPIONIC ACID DERIVATIVES AND METHODS OF USE THEREOF

BACKGROUND OF THE INVENTION

Field of the Invention

The present invention relates generally to field of medicinal chemistry and therapeutic compounds. Specifically, the present invention relates to derivatives of propionic acid as integrin inhibitors.

Description of the Related Art

Integrins are a large family of cell adhesion protein molecules that are expressed on numerous cells and which mediate a variety of cell-cell and cell-matrix interactions. Accordingly, the regulation of a number of physiological processes, such as, and including, cell adhesion, migration, signaling, survival and differentiation are known to involve these molecules. Each Integrin consists of a non-covalently associated alpha and beta transmembrane heterodimer subunit, with 18 different alpha and 8 different beta units being identified to date. Integrins function as conduits for signaling that occurs between the inside of cells and their external environment. Through ligand interactions, integrins sense the extracellular environment, activate, and then relay this information to the inside of the cell. This process is fundamental to the functional interaction of cells to various tissues such as and including the vascular endothelium, bone marrow stromal cells, some tumor cells and the gastrointestinal mucosal. Additionally, as integrins are widely expressed on leukocytes, especially T-cells, and thus are critical players in the regulation of the pathophysiologic processes of inflammation and autoimmune disease.

To date, approximately 24 different integrin molecules have been identified. Of these, the integrins derived from the alpha 4 subunit are associated with disease states of current unmet medical need. Two such integrins are alpha 4 beta 1 (α4β1, also called VLA-4 for very late antigen-4) and alpha 4 beta 7 (α4β7, also known as mucosal vascular addressin cell adhesion molecule 1 (MAdCAM-1)). These two alpha-4 integrins are the primary pathogenic targets of this patent application.

There are three main types of white blood cells: granulocytes, monocytes and lymphocytes. The alpha 4 integrins are expressed on the surface of monocytes, lymphocytes and two subclasses of granulocytes: eosinophils and basophils. These proteins play a key role in cell adhesion through their ability to recognize and bind to other cell surface proteins or other proteins such as vascular cell adhesion molecule 1 (VCAM-I), fibronectin, or other proteins associated with the endothelial cells that line the interior wall of capillaries. For example, following infection or damage of tissue surrounding a capillary, endothelial cells express a series of adhesion molecules, including VCAM-I, that are critical for binding the white blood cells that are necessary for fighting infection. In a similar fashion, alpha 4 beta 7, critical for homing to intestinal mucosa, is induced during T cell activation in Peyer's patches or mesenteric lymph nodes.

Some of the disease conditions that currently are, and in the future might be, treated by the inhibition of the alpha 4 integrins include, but is not limited to, hematopoietic stem cell transplant therapy, sickle cell disease, dry eye, atherosclerosis, rheumatoid arthritis, asthma, allergy, multiple sclerosis, lupus, inflammatory bowel disease, graft rejection, contact hypersensitivity, and diabetes. In addition to being found on some white blood cells, alpha 4 integrins are also found on various cancer cells, including leukemia, melanoma, lymphoma and sarcoma cells. Cell adhesion involving alpha 4 beta1 is thought to be involved in the metastasis and survival of certain cancer cells. Inhibitors of alpha 4 beta1 binding may, therefore, also be useful in the treatment of some forms of cancer.

The isolation and purification of a peptide which inhibits the binding of alpha 4 beta 1 to a protein is disclosed in U.S. Pat. No. 5,510,332. Peptides which inhibit binding are disclosed in WO 95/15973, EP 0 341915, EP 0 422 938 A1, U.S. Pat. No. 5,192,746 and WO 96/06108. Novel small molecule compounds which are useful for inhibition and prevention of cell adhesion and cell adhesion-mediated pathologies are disclosed in WO 96/22966, WO 98/04247 and US 2004/0234624 A1 (WO 98/04913), WO2005014534 A1, U.S. Pat. Nos. 7,812,030, 6,972,296, 6,723,711, 6,262,084.

It is the objective of this invention to provide novel small molecule compounds which are antagonists of the action of alpha 4 beta 1 and alpha 4 beta 7 binding and their corresponding pharmaceutical compositions which include such novel compounds.

SUMMARY OF THE INVENTION

The present invention is directed to a compound of formula I having a chemical structure of

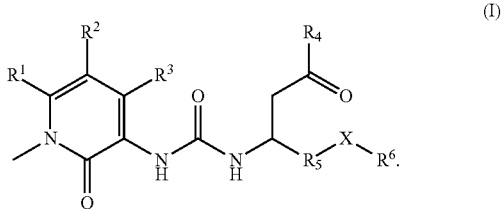

In these compounds, $R^1$ and $R^2$ independently may be hydrogen, halogen, $C_{1-4}$ alkyl, $C_{3-6}$ cycloalkyl, or arylalkyl. $R^3$ may be hydroxyl or oxido paired with a pharmaceutically acceptable cation. $R^4$ may be hydroxyl, $C_{1-4}$ alkyoxy, or oxido paired with a pharmaceutically acceptable cation. $R^5$ may be phenyl, aryl, heteroaryl or arylalkyl which is substituted with one or more of $C_{1-4}$ alkyl, alkoxy, aryloxy, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl, haloalkyl. X may be $CH_2$, O, or $CF_2$. $R^6$ may be $C_{1-4}$ alkyl, phenyl, aryl, heteroaryl which is substituted with one or more of $C_{1-4}$ alkyl, alkoxy, aryl, aryloxy, halogen, haloalkoxy, hydroxyl, —$CF_3$, —$OCF_3$, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl or haloalkyl. The compounds encompass pharmaceutically acceptable salts or stereoisomers thereof.

The present invention is directed to a related compound of formula II having a chemical structure of

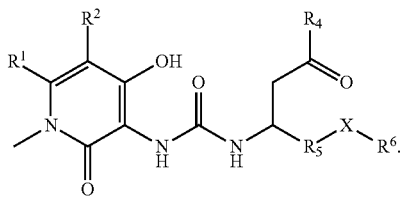

(II)

In these compounds, $R^1$ and $R^2$ independently may be hydrogen or methyl. $R^4$ may be hydroxyl, $C_{1-4}$ alkyoxy, or oxido paired with a pharmaceutically acceptable cation. $R^5$ may be phenyl, aryl, heteroaryl or arylalkyl which is substituted with one or more of $C_{1-4}$ alkyl, alkoxy, aryloxy, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl, haloalkyl. X may be $CH_2$, O, or $CF_2$. $R^6$ may be $C_{1-4}$ alkyl, phenyl, aryl, heteroaryl which is substituted with one or more of $C_{1-4}$ alkyl, alkoxy, aryl, aryloxy, halogen, haloalkoxy, hydroxyl, —$CF_3$, —$OCF_3$, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl or haloalkyl. The compounds encompass pharmaceutically acceptable salts or stereoisomers thereof.

The present invention also is directed to pharmaceutical composition, comprising at least one compound as described herein and one or more pharmaceutically acceptable carriers.

The present invention is directed further to a method for treating a pathophysiological condition mediated by α4 integrins, i.e. α4β1, α4β7 or mixed α4β1 and α4β7 integrin in a subject in need of such treatment. The method comprises administering to the subject a pharmacologically effective amount of the pharmaceutical composition as described herein.

The present invention is directed further still to a method for antagonizing α4-integrin action of a cell associated with a pathophysiological condition. The method comprises contacting the cell with one or more compounds as described herein.

The present invention is directed further still to a method for antagonizing the action of an α4 integrin to treat a pathophysiological condition in a subject. The method comprises administering to the subject a pharmacologically effective amount of one or more of the compounds as described herein.

The present invention is directed further still to a method for treatment of hematopoietic stem cell transplant therapy, sickle cell disease, dry eye, atherosclerosis, rheumatoid arthritis, asthma, allergy, multiple sclerosis, lupus, inflammatory bowel disease, graft rejection, contact hypersensitivity, stroke, pulmonary arterial hypertension, diabetes, or cancer which comprises administering to the subject an effective amount of at least one compound disclosed in this invention.

Other and further aspects, features, benefits, and advantages of the present invention will be apparent from the following description of the presently preferred embodiments of the invention given for the purpose of disclosure.

DETAILED DESCRIPTION OF THE INVENTION

As used herein in the specification, "a" or "an" may mean one or more. As used herein in the claim(s), when used in conjunction with the word "comprising", the words "a" or "an" may mean one or more than one.

As used herein, the acronym "nd" is intended to mean not yet determined.

As used herein, the term alpha 4 integrin(s) (aka α4-integrin(s)) refers to the class of integrin dimer molecules composed of the alpha 4 subunit coupled with another subunit normally referred to as a beta (b) subunit. Typical, but not exclusive, examples are α4β1 and α4β7.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

The term "alkyl" as used herein, alone or in combination, refers to $C_1$-$C_{12}$ straight or branched, substituted or unsubstituted saturated chain radicals derived from saturated hydrocarbons by the removal of one hydrogen atom, unless the term alkyl is preceded by a $C_x$-$C_y$ designation. Representative examples of alkyl groups include methyl, ethyl, n-propyl, iso-propyl, n-butyl, sec-butyl, iso-butyl, and tert-butyl among others.

The term "cycloalkyl" as used herein refers to an aliphatic ring system having 3 to 10 carbon atoms and 1 to 3 rings, including, but not limited to cyclopropyl, cyclopentyl, cyclohexyl, norbornyl, and adamantyl among others. Cycloalkyl groups can be unsubstituted or substituted with one, two or three substituents independently selected from lower alkyl, haloalkyl, alkoxy, thioalkoxy, amino, alkylamino, dialkylamino, hydroxyl, halo, mercapto, nitro, carboxaldehyde, carboxy, alkoxycarbonyl and carboxamide.

"Cycloalkyl" includes cis or trans forms. Furthermore, the substituents may either be in endo or exo positions in the bridged bicyclic systems.

The term "halo" or "halogen" as used herein refers to I, Br, Cl or F.

The term "haloalkyl" as used herein refers to $C_1$-$C_4$ alkyl radical, to which is appended at least one halogen substituent, for example chloromethyl, fluoroethyl, difluoromethyl, trifluoromethyl and pentafluoroethyl among others.

The term "alkoxy" as used herein, alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "haloalkoxy" as used herein, alone or in combination, refers to an haloalkyl ether radical, wherein the term "haloalkyl" is as defined above. Examples of suitable haloalkyl ether radicals include, but are not limited to, chloromethoxy, trifluoromethoxy, difluoromethoxy, trifluoroethoxy and the like.

The term "thioalkoxy" refers to a thioether radical of formula alkyl-S—, wherein "alkyl" is as defined above.

The term "dialkylamino" as used herein refers to $R_f R_g$ N— wherein $R_f$ and $R_g$ are independently selected from $C_1$-$C_4$ alkyl, for example diethylamino, and methyl propylamino, among others.

The term "aryl" or "aromatic" as used herein alone or in combination refers to a substituted or unsubstituted carbocyclic aromatic group having about 6 to 12 carbon atoms such as phenyl, naphthyl, indenyl, indanyl, azulenyl, fluorenyl and anthracenyl; or a heterocyclic aromatic group containing at least one endocyclic N, O or S atom such as furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxyazinyl, pyrazolo[1,5-c]triazinyl and the like. "Aralkyl" and "alkylaryl" employ the term "alkyl" as defined above. Rings may be multiply substituted.

The term "arylalkyl" as used herein, alone or in combination, refers to an aryl substituted alkyl radical, wherein the terms "alkyl" and "aryl" are as defined above. Examples of suitable arylalkyl radicals include, but are not limited to, phenylmethyl, phenethyl, phenylhexyl, diphenylmethyl, pyridylmethyl, tetrazolyl methyl, furylmethyl, imidazolyl methyl, indolylmethyl, thienylpropyl and the like.

The term "aryloxy" as used herein, alone or in combination, refers to an aryl ether radical, wherein the term "aryl" is as defined above.

The term "benzyl" as used herein refers to $C_6H_5CH_2$—.

The term "heterocyclyl" as used herein, alone or in combination, refers to a non-aromatic 3- to 10-membered ring containing at least one endocyclic N, O, or S atom. The heterocycle may be optionally aryl-fused. The heterocycle may also optionally be substituted with at least one substituent which is independently selected from the group consisting of hydrogen, halogen, hydroxyl, amino, nitro, trifluoromethyl, trifluoromethoxy, alkyl, aralkyl, alkenyl, alkynyl, aryl, cyano, carboxy, carboalkoxy, carboxyalkyl, oxo, arylsulfonyl and aralkylaminocarbonyl among others.

The term "heteroaryl" as used herein refers to aromatic moieties containing one or more heteroatoms (e.g., N, O, S, or the like) as part of the ring structure and having in the range of 5 up to 14 total atoms in the ring structure (i.e., carbon atoms and heteroatoms). "Substituted heteroaryl" refers to heteroaryl groups further bearing one or more substituents.

The term "stereoisomer" as used herein refers to a compound made up of the same atoms bonded by the same bonds but having different three-dimensional structures which are not interchangeable. The three-dimensional structures are called configurations.

The term "pharmaceutically acceptable salts" as used herein of a compound is meant salts which are pharmaceutically acceptable as defined herein and which have the desired pharmacological action of the parent compound. Such salts comprise the addition salts of pharmaceutically acceptable bases formed when an acid proton contained in the parent compound is either replaced by a metal ion e.g. an alkaline metal ion, an alkaline-earth metal ion or aluminium ion; or coordinated with a pharmaceutically acceptable organic or inorganic base. Acceptable organic bases include diethanolamine, ethanolamine, N-methylglucamine, triethanolamine, tromethamine and the like. Acceptable inorganic bases include aluminium hydroxide, calcium hydroxide, potassium hydroxide, sodium carbonate and sodium hydroxide.

The term "pharmaceutically acceptable cation" as used herein is the cation component of a "pharmaceutically acceptable salt". Especially, in both instances, sodium is preferred.

The term "effective amount" as used herein refers to generally an amount effective to accomplish the intended purpose, e.g., a pharmacologically effective amount. However, the amount can be less than that amount when a plurality of the compositions are to be administered, i.e., the total effective amount can be administered in cumulative dosage units. The amount of active agent can also be more than the effective amount when the composition provides sustained release of the pharmacologically active agent. The total amount of a pharmacologically active agent to be used can be determined by methods known to those skilled in the art. However, because the compositions may deliver the pharmacologically active agent more efficiently than prior compositions, less amounts of active agent than those used in prior dosage unit forms or delivery systems can be administered to a subject while still achieving the same blood levels and/or therapeutic effects.

As used herein, the term "sodium" means the sodium salt of the disclosed compounds and includes the monosodium salt, the disodium salt and mixtures thereof.

As used herein, the term "contacting" refers to any suitable method of bringing a compound or a pharmaceutical composition into contact with a cell in vivo, in vitro or ex vivo. For in vivo applications, any known method of administration is suitable as described herein.

As used herein, the term "subject" refers to any recipient, for example a human or non-human mammal, of the compounds and/or pharmaceutical compositions described herein.

Use of the above terms is meant to encompass substituted and unsubstituted moieties. Substitution may be by one or more groups such as alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogens, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, hereroaryl, heterocyclyl, alkylheterocyclyl, heterocyclylalkyl, oxo, arylsulfonyl and aralkylaminocarbonyl or any of the substituents of the preceding paragraphs or any of those substituents either attached directly or by suitable linkers. The linkers are typically short chains of 1-3 atoms containing any combination of —C—, —C(O)—, —NH—, —S—, —S(O)—, —O—, —C(O)O— or —S(O)O—. Rings may be substituted multiple times.

In one embodiment of the invention, there is provided a compound of formula I having a chemical structure of

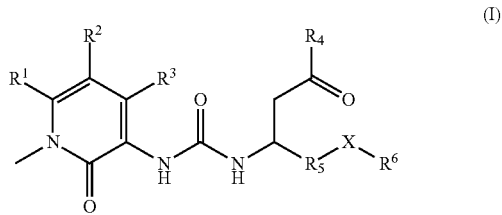

where $R^1$ and $R^2$ are independently hydrogen, halogen, $C_{1-4}$ alkyl, $C_{3-6}$ cycloalkyl or arylalkyl; $R^3$ is hydroxyl or oxido paired with a pharmaceutically acceptable cation; $R^4$ is hydroxyl, $C_{1-4}$ alkyoxy, or oxido paired with a pharmaceutically acceptable cation; $R^5$ is phenyl, aryl, heteroaryl or aralkyl which is substituted with one or more of $C_{1-4}$ alkyl, alkoxy, aryloxy, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl, haloalkyl; X is $CH_2$, O, or $CF_2$; $R^6$ is $C_{1-4}$ alkyl, phenyl, aryl, heteroaryl which is substituted with one or more of $C_{1-4}$ alkyl, alkoxy, aryloxy, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl or haloalkyl; or a pharmaceutically acceptable salt or stereoisomers thereof.

In this embodiment, $R^4$ is hydroxyl, methoxy, ethoxy, t-butoxy, or oxido paired with a pharmaceutically acceptable cation. Also in this embodiment $R^3$ is hydroxyl or oxido paired with a pharmaceutically acceptable cation. Also in this embodiment and all aspects thereof as described the pharmaceutically acceptable salt is a mono or a disodium salt and the stereoisomer is of the (S)-configuration.

In one aspect of this embodiment, the provided compound of formula I is a compound of formula IA having a chemical structure of

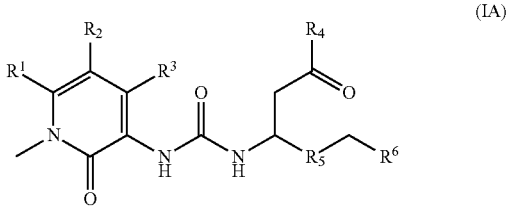

(IA)

where $R^1$ and $R^2$ are independently hydrogen, halogen, $C_{1-4}$ alkyl, $C_{3-6}$ cycloalkyl or arylalkyl; $R^3$ is hydroxyl or oxido paired with a pharmaceutically acceptable cation; $R^4$ is hydroxyl, $C_{1-4}$ alkyoxy, or oxido paired with a pharmaceutically acceptable cation; $R^5$ is phenyl, aryl, heteroaryl or aralkyl which is substituted with one or more of $C_{1-4}$ alkyl, alkoxy, aryloxy, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl, haloalkyl; X is $CH_2$, O, or $CF_2$; $R^6$ is $C_{1-4}$ alkyl, phenyl, aryl, heteroaryl which is substituted with one or more of $C_{1-4}$ alkyl, alkoxy, aryloxy, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl or haloalkyl; or a pharmaceutically acceptable salt or stereoisomers thereof.

In another aspect of this embodiment, the provided compound of formula I is a compound of formula IB having a chemical structure of

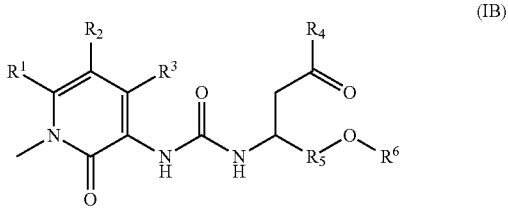

(IB)

where $R^1$ and $R^2$ are independently hydrogen, halogen, $C_{1-4}$ alkyl, $C_{3-6}$ cycloalkyl or arylalkyl; $R^3$ is hydroxyl or oxido paired with a pharmaceutically acceptable cation; $R^4$ is hydroxyl, $C_{1-4}$ alkyoxy, or oxido paired with a pharmaceutically acceptable cation; $R^5$ is phenyl, aryl, heteroaryl or aralkyl which is substituted with one or more of $C_{1-4}$ alkyl, alkoxy, aryloxy, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl, haloalkyl; X is $CH_2$, O, or $CF_2$; $R^6$ is $C_{1-4}$ alkyl, phenyl, aryl, heteroaryl which is substituted with one or more of $C_{1-4}$ alkyl, alkoxy, aryloxy, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl or haloalkyl; or a pharmaceutically acceptable salt or stereoisomers thereof.

In yet another aspect of this embodiment, the provided compound of formula I is a compound of formula IC having a chemical structure of

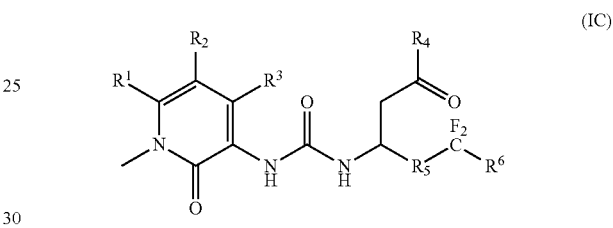

(IC)

where $R^1$ and $R^2$ are independently hydrogen, halogen, $C_{1-4}$ alkyl, $C_{3-6}$ cycloalkyl or arylalkyl; $R^3$ is hydroxyl or oxido paired with a pharmaceutically acceptable cation; $R^4$ is hydroxyl, $C_{1-4}$ alkyoxy, or oxido paired with a pharmaceutically acceptable cation; $R^5$ is phenyl, aryl, heteroaryl or aralkyl which is substituted with one or more of $C_{1-4}$ alkyl, alkoxy, aryloxy, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl, haloalkyl; X is $CH_2$, O, or $CF_2$; $R^6$ is $C_{1-4}$ alkyl, phenyl, aryl, heteroaryl which is substituted with one or more of $C_{1-4}$ alkyl, alkoxy, aryloxy, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl or haloalkyl; or a pharmaceutically acceptable salt or stereoisomers thereof.

In another embodiment of the invention, there is provided pharmaceutical compositions comprising at least one compound as described supra and one or more pharmaceutically acceptable carriers.

In yet another embodiment of the invention, there is provided a method for treating a pathophysiological condition mediated by an α4 integrins i.e. α4β1, α4β7 or mixed α4β1 and α4β7 integrin in a subject in need of such treatment comprising administering to the subject a pharmacologically effective amount of the pharmaceutical composition as described supra. In this embodiment, representative pathophysiological conditions include but are not limited to atherosclerosis, rheumatoid arthritis, asthma, allergy, multiple sclerosis, lupus, inflammatory bowel disease, graft rejection, contact hypersensitivity, dry eye, hematopoietic stem cell transplant therapy, diabetes, sickle cell disease, or cancer.

In yet another embodiment of the invention, there is provided a method for antagonizing α4-integrin action of a cell associated with a pathophysiological condition, comprising: contacting the cell with one or more compounds as described supra. In this embodiment the α4-integrin is α4β1 or α4β7. Also in this embodiment the pathophysiological condition is a cancer.

In yet another embodiment of the invention, there is provided a method antagonizing the action of an α4 integrin to treat a pathophysiological condition in a subject, comprising administering to the subject a pharmacologically effective amount of one or more of the compounds as described supra. In this embodiment, the representative pathophysiological conditions include but are not limited to, hematopoietic stem cell transplant therapy, sickle cell disease, dry eye, atherosclerosis, rheumatoid arthritis, asthma, allergy, multiple sclerosis, lupus, inflammatory bowel disease, graft rejection, contact hypersensitivity, stroke, pulmonary arterial hypertension and diabetes, or cancer.

In yet another embodiment of the invention, there is provided a compound of formula II having a chemical structure of

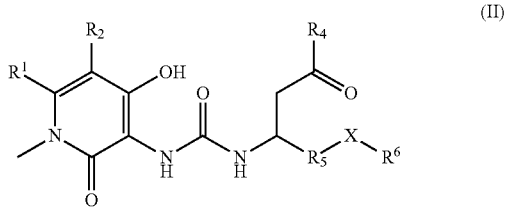

(II)

where $R^1$ and $R^2$ are independently hydrogen or methyl; $R^4$ is hydroxyl, $C_{1-4}$ alkyoxy, or oxido paired with a pharmaceutically acceptable cation; $R^5$ is phenyl, aryl, heteroaryl or arylalkyl which is substituted with one or more of $C_{1-4}$ alkyl, alkoxy, aryloxy, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl, haloalkyl; X is $CH_2$, O, or $CF_2$; $R^6$ is $C_{1-4}$ alkyl, phenyl, aryl, heteroaryl which is substituted with one or more of $C_{1-4}$ alkyl, alkoxy, aryloxy, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl or haloalkyl; or a pharmaceutically acceptable salt or stereoisomers thereof.

In one aspect of this embodiment, the provided compound of formula II is a compound of formula II A having a chemical structure of

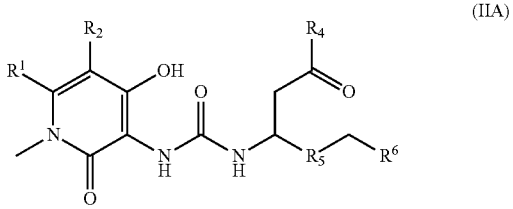

(IIA)

where $R^1$ and $R^2$ are independently hydrogen or methyl; $R^4$ is hydroxyl, $C_{1-4}$ alkyoxy, or oxido paired with a pharmaceutically acceptable cation; $R^5$ is phenyl, aryl, heteroaryl or arylalkyl which is substituted with one or more of $C_{1-4}$ alkyl, alkoxy, aryloxy, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl, haloalkyl; $R^6$ is $C_{1-4}$ alkyl, phenyl, aryl, heteroaryl which is substituted with one or more of $C_{1-4}$ alkyl, alkoxy, aryloxy, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl or haloalkyl; or a pharmaceutically acceptable salt or stereoisomers thereof.

In another aspect of the embodiment, the provided compound of formula II is a compound of formula II B having a chemical structure of

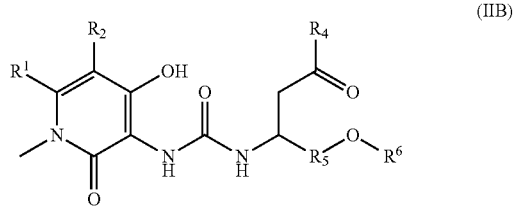

(IIB)

where $R^1$ and $R^2$ are independently hydrogen or methyl; $R^4$ is hydroxyl, $C_{1-4}$ alkyoxy, or oxido paired with a pharmaceutically acceptable cation; $R^5$ is phenyl, aryl, heteroaryl or arylalkyl which is substituted with one or more of $C_{1-4}$ alkyl, alkoxy, aryloxy, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl, haloalkyl; X is $CH_2$, O, or $CF_2$; $R^6$ is $C_{1-4}$ alkyl, phenyl, aryl, heteroaryl which is substituted with one or more of $C_{1-4}$ alkyl, alkoxy, aryloxy, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl or haloalkyl; or a pharmaceutically acceptable salt or stereoisomers thereof.

In yet another aspect of the embodiment, the provided compound of formula II is a compound of formula II C having a chemical structure of

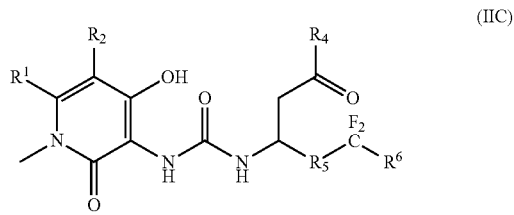

(IIC)

where $R^1$ and $R^2$ are independently hydrogen or methyl; $R^4$ is hydroxyl, $C_{1-4}$ alkyoxy, or oxido paired with a pharmaceutically acceptable cation; $R^5$ is phenyl, aryl, heteroaryl or arylalkyl which is substituted with one or more of $C_{1-4}$ alkyl, alkoxy, aryloxy, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl, haloalkyl; X is $CH_2$, O, or $CF_2$; $R^6$ is $C_{1-4}$ alkyl, phenyl, aryl, heteroaryl which is substituted with one or more of $C_{1-4}$ alkyl, alkoxy, aryloxy, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl or haloalkyl; or a pharmaceutically acceptable salt or stereoisomers thereof.

In yet another embodiment of the invention, there are provided the compounds:
ethyl 3-(3-(4-hydroxy-1,5-dimethyl-2-oxo-1,2-dihydropyridin-3-yl)ureido)-3-(3-phenoxy phenyl)propanoate 1-1, ethyl (S)-3-(3-(4-hydroxy-1,5-dimethyl-2-oxo-1,2-dihydropyridin-3-yl)ureido)-3-(3-phenoxyphenyl)propanoate 1-2,
ethyl (S)-3-(3-benzylphenyl)-3-(3-(4-hydroxy-1,5-dimethyl-2-oxo-1,2-dihydro pyridin-3-yl)ureido)propanoate 1-3,
ethyl 3-(3-(2-chlorobenzyl)phenyl)-3-(3-(4-hydroxy-1,5-dimethyl-2-oxo-1,2-di hydropyridin-3-yl)ureido)propanoate 1-4,
ethyl 3-(3-(3-chlorobenzyl)phenyl)-3-(3-(4-hydroxy-1,5-dimethyl-2-oxo-1,2-di hydropyridin-3-yl)ureido)propanoate 1-5,
ethyl 3-(3-(4-chlorobenzyl)phenyl)-3-(3-(4-hydroxy-1,5-dimethyl-2-oxo-1,2-di hydropyridin-3-yl)ureido)propanoate 1-6,
ethyl (S)-3-(4-(2-chlorobenzyl)phenyl)-3-(3-(4-hydroxy-1,5-dimethyl-2-oxo-1,2-di hydropyridin-3-yl)ureido)propanoate 1-7,
ethyl (S)-3-(3-(4-hydroxy-1,5-dimethyl-2-oxo-1,2-dihydropyridin-3-yl)ureido)-3-(3-(2-methylbenzyl)phenyl)propanoate 1-8,
ethyl (S)-3-(3-(4-hydroxy-1,5-dimethyl-2-oxo-1,2-dihydropyridin-3-yl)ureido)-3-(3-(3-methylbenzyl)phenyl)propanoate 1-9,
ethyl (S)-3-(3-(4-hydroxy-1,5-dimethyl-2-oxo-1,2-dihydropyridin-3-yl)ureido)-3-(3-(4-methylbenzyl)phenyl)propanoate 1-10,
ethyl (S)-3-(3-(4-hydroxy-1,6-dimethyl-2-oxo-1,2-dihydropyridin-3-yl)ureido)-3-(4-(2-methoxyphenoxy)phenyl)propanoate 2-1,
ethyl (S)-3-(3-(4-hydroxy-1,6-dimethyl-2-oxo-1,2-dihydropyridin-3-yl)ureido)-3-(4-(3-methoxyphenoxy)phenyl)propanoate 2-2,
ethyl (S)-3-(3-(4-hydroxy-1,6-dimethyl-2-oxo-1,2-dihydropyridin-3-yl)ureido)-3-(3-(p-tolyloxy)phenyl)propanoate 2-3,
ethyl (S)-3-(3-(4-hydroxy-1,6-dimethyl-2-oxo-1,2-dihydropyridin-3-yl)ureido)-3-(3-(2-methylbenzyl)phenyl)propanoate 2-4,
ethyl (S)-3-(3-(4-hydroxy-1,6-dimethyl-2-oxo-1,2-dihydropyridin-3-yl)ureido)-3-(5-(2-methylbenzyl)thiophen-2-yl)propanoate 2-5,
ethyl (S)-3-(3-(difluoro(o-tolyl)methyl)phenyl)-3-(3-(4-hydroxy-1-methyl-2-oxo-1,2-dihydropyridin-3-yl)ureido)propanoate 3-1,
ethyl (R)-3-(3-(difluoro(o-tolyl)methyl)phenyl)-3-(3-(4-hydroxy-1-methyl-2-oxo-1,2-dihydropyridin-3-yl)ureido)propanoate 3-2,
ethyl (S)-3-(3-(4-hydroxy-1-methyl-2-oxo-1,2-dihydropyridin-3-yl)ureido)-3-(3-phenoxyphenyl)propanoate 3-3,
ethyl (S)-3-(3-(4-hydroxy-1-methyl-2-oxo-1,2-dihydropyridin-3-yl)ureido)-3-(4-(2-methoxyphenoxy)phenyl)propanoate 3-4,
ethyl (S)-3-(3-(4-hydroxy-1-methyl-2-oxo-1,2-dihydropyridin-3-yl)ureido)-3-(4-(3-methoxyphenoxy)phenyl)propanoate 3-5,
ethyl (S)-3-(3-(4-hydroxy-1-methyl-2-oxo-1,2-dihydropyridin-3-yl)ureido)-3-(4-(o-tolyloxy)phenyl)propanoate 3-6,
ethyl (S)-3-(3-(4-hydroxy-1-methyl-2-oxo-1,2-dihydropyridin-3-yl)ureido)-3-(4-(p-tolyloxy)phenyl)propanoate 3-7,
ethyl (S)-3-(4-benzylphenyl)-3-(3-(4-hydroxy-1-methyl-2-oxo-1,2-dihydropyridin-3-yl)ureido)propanoate 3-8,
ethyl (S)-3-(3-(4-hydroxy-1-methyl-2-oxo-1,2-dihydropyridin-3-yl)ureido)-3-(4-(2-methylbenzyl)phenyl)propanoate 3-9,
ethyl (S)-3-(3-(4-hydroxy-1-methyl-2-oxo-1,2-dihydropyridin-3-yl)ureido)-3-(4-(3-methylbenzyl)phenyl)propanoate 3-10,
ethyl (S)-3-(3-(4-hydroxy-1-methyl-2-oxo-1,2-dihydropyridin-3-yl)ureido)-3-(4-(4-methylbenzyl)phenyl)propanoate 3-11,
ethyl (S)-3-(3-(2-ethylbenzyl)phenyl)-3-(3-(4-hydroxy-1-methyl-2-oxo-1,2-dihydropyridin-3-yl)ureido)propanoate 3-12,
ethyl (S)-3-(3-(4-hydroxy-1-methyl-2-oxo-1,2-dihydropyridin-3-yl)ureido)-3-(3-(2-methylbenzyl)phenyl)propanoate 3-13,
ethyl (S)-3-(3-(4-hydroxy-1-methyl-2-oxo-1,2-dihydropyridin-3-yl)ureido)-3-(3-(3-methylbenzyl)phenyl)propanoate 3-14,
ethyl (S)-3-(3-(4-hydroxy-1-methyl-2-oxo-1,2-dihydropyridin-3-yl)ureido)-3-(3-(4-methylbenzyl)phenyl)propanoate 3-15,
ethyl (S)-3-(3-(4-hydroxy-1-methyl-2-oxo-1,2-dihydropyridin-3-yl)ureido)-3-(3-(2-(trifluoromethyl)benzyl)phenyl)propanoate 3-16,
ethyl (S)-3-(3-(4-hydroxy-1-methyl-2-oxo-1,2-dihydropyridin-3-yl)ureido)-3-(3-(3-(trifluoromethyl)benzyl)phenyl)propanoate 3-17,
ethyl (S)-3-(3-(4-hydroxy-1-methyl-2-oxo-1,2-dihydropyridin-3-yl)ureido)-3-(3-(4-(trifluoromethyl)benzyl)phenyl)propanoate 3-18,
ethyl (S)-3-(3-(2-(difluoromethoxy)benzyl)phenyl)-3-(3-(4-hydroxy-1-methyl-2-oxo-1,2-dihydropyridin-3-yl)ureido)propanoate 3-19,
ethyl (S)-3-(3-(4-hydroxy-1-methyl-2-oxo-1,2-dihydropyridin-3-yl)ureido)-3-(3-(2-methoxybenzyl)phenyl)propanoate 3-20,
ethyl (S)-3-(3-(2-fluorobenzyl)phenyl)-3-(3-(4-hydroxy-1-methyl-2-oxo-1,2-dihydropyridin-3-yl)ureido)propanoate 3-21,
ethyl (S)-3-(3-(2,6-dimethylbenzyl)phenyl)-3-(3-(4-hydroxy-1-methyl-2-oxo-1,2-dihydropyridin-3-yl)ureido)propanoate 3-22,
ethyl (S)-3-(3-(5-fluoro-2-methylbenzyl)phenyl)-3-(3-(4-hydroxy-1-methyl-2-oxo-1,2-dihydropyridin-3-yl)ureido)propanoate 3-23,
ethyl (S)-3-(3-(4-hydroxy-1-methyl-2-oxo-1,2-dihydropyridin-3-yl)ureido)-3-(5-(2-methylbenzyl)thiophen-2-yl)propanoate 3-24,
ethyl (S)-3-(5-benzylthiophen-2-yl)-3-(3-(4-hydroxy-1-methyl-2-oxo-1,2-di hydropyridin-3-yl)ureido)propanoate 3-25,
ethyl (S)-3-(3-(4-hydroxy-1-methyl-2-oxo-1,2-dihydropyridin-3-yl)ureido)-3-(3-(o-tolyloxy)phenyl)propanoate 3-26,
ethyl (S)-3-(3-(4-hydroxy-1-methyl-2-oxo-1,2-dihydropyridin-3-yl)ureido)-3-(3-(m-tolyloxy)phenyl)propanoate 3-27,
ethyl (S)-3-(3-(4-hydroxy-1-methyl-2-oxo-1,2-dihydropyridin-3-yl)ureido)-3-(3-(p-tolyloxy)phenyl)propanoate 3-28,
ethyl (S)-3-(3-(4-hydroxy-1-methyl-2-oxo-1,2-dihydropyridin-3-yl)ureido)-3-(3-(2-methoxyphenoxy)phenyl)propanoate 3-29,
ethyl (S)-3-(3-(2-chlorophenoxy)phenyl)-3-(3-(4-hydroxy-1-methyl-2-oxo-1,2-dihydropyridin-3-yl)ureido)propanoate 3-30,
ethyl (S)-3-(3-(2,4-difluorophenoxy)phenyl)-3-(3-(4-hydroxy-1-methyl-2-oxo-1,2-dihydropyridin-3-yl)ureido) propanoate 3-31, ethyl (S)-3-(3-(2,6-dimethylphenoxy)phenyl)-3-(3-(4-hydroxy-1-methyl-2-oxo-1,2-dihydropyridin-3-yl)ureido) propanoate 3-32,
3-(3-(4-hydroxy-1,5-dimethyl-2-oxo-1,2-dihydropyridin-3-yl)ureido)-3-(3-phenoxyphenyl)propanoic acid 1-11,
(S)-3-(3-(4-hydroxy-1,5-dimethyl-2-oxo-1,2-dihydropyridin-3-yl)ureido)-3-(3-phenoxyphenyl)propanoic acid 1-12,
(S)-3-(3-benzylphenyl)-3-(3-(4-hydroxy-1,5-dimethyl-2-oxo-1,2-dihydropyridin-3-yl)ureido)propanoic acid 1-13,
3-(3-(2-chlorobenzyl)phenyl)-3-(3-(4-hydroxy-1,5-dimethyl-2-oxo-1,2-dihydropyridin-3-yl)ureido)propanoic acid 1-14,
3-(3-(3-chlorobenzyl)phenyl)-3-(3-(4-hydroxy-1,5-dimethyl-2-oxo-1,2-dihydropyridin-3-yl)ureido)propanoic acid 1-15,
3-(3-(4-chlorobenzyl)phenyl)-3-(3-(4-hydroxy-1,5-dimethyl-2-oxo-1,2-dihydropyridin-3-yl)ureido)propanoic acid 1-16,
(S)-3-(4-(2-chlorobenzyl)phenyl)-3-(3-(4-hydroxy-1,5-dimethyl-2-oxo-1,2-dihydropyridin-3-yl)ureido)propanoic acid 1-17,
(S)-3-(3-(4-hydroxy-1,5-dimethyl-2-oxo-1,2-dihydropyridin-3-yl)ureido)-3-(3-(2-methylbenzyl)phenyl)propanoic acid 1-18,
(S)-3-(3-(4-hydroxy-1,5-dimethyl-2-oxo-1,2-dihydropyridin-3-yl)ureido)-3-(3-(3-methylbenzyl)phenyl)propanoic acid 1-19,
(S)-3-(3-(4-hydroxy-1,5-dimethyl-2-oxo-1,2-dihydropyridin-3-yl)ureido)-3-(3-(4-methylbenzyl)phenyl)propanoic acid 1-20,
(S)-3-(3-(4-hydroxy-1,6-dimethyl-2-oxo-1,2-dihydropyridin-3-yl)ureido)-3-(4-(2-methoxyphenoxy)phenyl)propanoic acid 2-6,
(S)-3-(3-(4-hydroxy-1,6-dimethyl-2-oxo-1,2-dihydropyridin-3-yl)ureido)-3-(4-(3-methoxyphenoxy)phenyl)propanoic acid 2-7,
(S)-3-(3-(4-hydroxy-1,6-dimethyl-2-oxo-1,2-dihydropyridin-3-yl)ureido)-3-(3-(p-tolyloxy)phenyl)propanoic acid 2-8,
(S)-3-(3-(4-hydroxy-1,6-dimethyl-2-oxo-1,2-dihydropyridin-3-yl)ureido)-3-(3-(2-methylbenzyl)phenyl)propanoic acid 2-9,
(S)-3-(3-(4-hydroxy-1,6-dimethyl-2-oxo-1,2-dihydropyridin-3-yl)ureido)-3-(5-(2-methylbenzyl)thiophen-2-yl)propanoic acid 2-10,
(S)-3-(3-(difluoro(o-tolyl)methyl)phenyl)-3-(3-(4-hydroxy-1-methyl-2-oxo-1,2-dihydropyridin-3-yl)ureido)propanoic acid 3-33,
(R)-3-(3-(difluoro(o-tolyl)methyl)phenyl)-3-(3-(4-hydroxy-1-methyl-2-oxo-1,2-dihydropyridin-3-yl)ureido)propanoic acid 3-34,
(S)-3-(3-(4-hydroxy-1-methyl-2-oxo-1,2-dihydropyridin-3-yl)ureido)-3-(3-phenoxyphenyl)propanoic acid 3-35,
(S)-3-(3-(4-hydroxy-1-methyl-2-oxo-1,2-dihydropyridin-3-yl)ureido)-3-(4-(2-methoxyphenoxy)phenyl)propanoic acid 3-36,
(S)-3-(3-(4-hydroxy-1-methyl-2-oxo-1,2-dihydropyridin-3-yl)ureido)-3-(4-(3-methoxyphenoxy)phenyl)propanoic acid 3-37,
(S)-3-(3-(4-hydroxy-1-methyl-2-oxo-1,2-dihydropyridin-3-yl)ureido)-3-(4-(o-tolyloxy)phenyl)propanoic acid 3-38,
(S)-3-(3-(4-hydroxy-1-methyl-2-oxo-1,2-dihydropyridin-3-yl)ureido)-3-(4-(p-tolyloxy)phenyl)propanoic acid 3-39,
(S)-3-(4-benzylphenyl)-3-(3-(4-hydroxy-1-methyl-2-oxo-1,2-dihydropyridin-3-yl)ureido)propanoic acid 3-40,
(S)-3-(3-(4-hydroxy-1-methyl-2-oxo-1,2-dihydropyridin-3-yl)ureido)-3-(4-(2-methylbenzyl)phenyl)propanoic acid 3-41,
(S)-3-(3-(4-hydroxy-1-methyl-2-oxo-1,2-dihydropyridin-3-yl)ureido)-3-(4-(3-methylbenzyl)phenyl)propanoic acid 3-42,
(S)-3-(3-(4-hydroxy-1-methyl-2-oxo-1,2-dihydropyridin-3-yl)ureido)-3-(4-(4-methylbenzyl)phenyl)propanoic acid 3-43,
(S)-3-(3-(2-ethylbenzyl)phenyl)-3-(3-(4-hydroxy-1-methyl-2-oxo-1,2-dihydro pyridin-3-yl)ureido)propanoic acid 3-44,
(S)-3-(3-(4-hydroxy-1-methyl-2-oxo-1,2-dihydropyridin-3-yl)ureido)-3-(3-(2-methylbenzyl)phenyl)propanoic acid 3-45,
(S)-3-(3-(4-hydroxy-1-methyl-2-oxo-1,2-dihydropyridin-3-yl)ureido)-3-(3-(3-methylbenzyl)phenyl)propanoic acid 3-46,
(S)-3-(3-(4-hydroxy-1-methyl-2-oxo-1,2-dihydropyridin-3-yl)ureido)-3-(3-(4-methylbenzyl)phenyl)propanoic acid 3-47,
(S)-3-(3-(4-hydroxy-1-methyl-2-oxo-1,2-dihydropyridin-3-yl)ureido)-3-(3-(2-(trifluoromethyl)benzyl)phenyl)propanoic acid 3-48,
(S)-3-(3-(4-hydroxy-1-methyl-2-oxo-1,2-dihydropyridin-3-yl)ureido)-3-(3-(3-(trifluoromethyl)benzyl)phenyl)propanoic acid 3-49,
(S)-3-(3-(4-hydroxy-1-methyl-2-oxo-1,2-dihydropyridin-3-yl)ureido)-3-(3-(4-(trifluoromethyl)benzyl)phenyl)propanoic acid 3-50,
(S)-3-(3-(2-(difluoromethoxy)benzyl)phenyl)-3-(3-(4-hydroxy-1-methyl-2-oxo-1,2-dihydropyridin-3-yl)ureido)propanoic acid 3-51,
(S)-3-(3-(4-hydroxy-1-methyl-2-oxo-1,2-dihydropyridin-3-yl)ureido)-3-(3-(2-methoxybenzyl)phenyl)propanoic acid 3-52,
(S)-3-(3-(2-fluorobenzyl)phenyl)-3-(3-(4-hydroxy-1-methyl-2-oxo-1,2-dihydropyridin-3-yl)ureido)propanoic acid 3-53,
(S)-3-(3-(2,6-dimethylbenzyl)phenyl)-3-(3-(4-hydroxy-1-methyl-2-oxo-1,2-dihydropyridin-3-yl)ureido)propanoic acid 3-54,
(S)-3-(3-(5-fluoro-2-methyl benzyl)phenyl)-3-(3-(4-hydroxy-1-methyl-2-oxo-1,2-dihydropyridin-3-yl)ureido) propanoic acid 3-55,
(S)-3-(3-(4-hydroxy-1-methyl-2-oxo-1,2-dihydropyridin-3-yl)ureido)-3-(5-(2-methylbenzyl)thiophen-2-yl)propanoic acid 3-56,
(S)-3-(5-benzylthiophen-2-yl)-3-(3-(4-hydroxy-1-methyl-2-oxo-1,2-dihydropyridin-3-yl)ureido)propanoic acid 3-57,
(S)-3-(3-(4-hydroxy-1-methyl-2-oxo-1,2-dihydropyridin-3-yl)ureido)-3-(3-(o-tolyloxy)phenyl)propanoic acid 3-58,
(S)-3-(3-(4-hydroxy-1-methyl-2-oxo-1,2-dihydropyridin-3-yl)ureido)-3-(3-(m-tolyloxy)phenyl)propanoic acid 3-59,
(S)-3-(3-(4-hydroxy-1-methyl-2-oxo-1,2-dihydropyridin-3-yl)ureido)-3-(3-(p-tolyloxy)phenyl)propanoic acid 3-60,
(S)-3-(3-(4-hydroxy-1-methyl-2-oxo-1,2-dihydropyridin-3-yl)ureido)-3-(3-(2-methoxyphenoxy)phenyl)propanoic acid 3-61,
(S)-3-(3-(2-chlorophenoxy)phenyl)-3-(3-(4-hydroxy-1-methyl-2-oxo-1,2-dihydropyridin-3-yl)ureido)propanoic acid 3-62,
(S)-3-(3-(2,4-difluorophenoxy)phenyl)-3-(3-(4-hydroxy-1-methyl-2-oxo-1,2-dihydropyridin-3-yl)ureido)propanoic acid 3-63, (S)-3-(3-(2,6-dimethylphenoxy)phenyl)-3-(3-(4-hydroxy-1-methyl-2-oxo-1,2-dihydropyridin-3-yl)ureido)propanoic acid 3-64,
sodium 3-(3-(1,5-dimethyl-4-oxido-2-oxo-1,2-dihydropyridin-3-yl)ureido)-3-(3-phenoxyphenyl)propanoate 1-22,
sodium (S)-3-(3-benzylphenyl)-3-(3-(1,5-dimethyl-4-oxido-2-oxo-1,2-dihydropyridin-3-yl)ureido)propanoate 1-23,
sodium 3-(3-(2-chlorobenzyl)phenyl)-3-(3-(1,5-dimethyl-4-oxido-2-oxo-1,2-dihydropyridin-3-yl)ureido)propanoate 1-24,
sodium 3-(3-(3-chlorobenzyl)phenyl)-3-(3-(1,5-dimethyl-4-oxido-2-oxo-1,2-dihydropyridin-3-yl)ureido)propanoate 1-25,
sodium 3-(3-(4-chlorobenzyl)phenyl)-3-(3-(1,5-dimethyl-4-oxido-2-oxo-1,2-dihydropyridin-3-yl)ureido)propanoate 1-26,
sodium 3-(4-(2-chlorobenzyl)phenyl)-3-(3-(1,5-dimethyl-4-oxido-2-oxo-1,2-dihydropyridin-3-yl)ureido)propante 1-27,
sodium (S)-3-(3-(1,5-dimethyl-4-oxido-2-oxo-1,2-dihydropyridin-3-yl)ureido)-3-(3-(2-methylbenzyl)phenyl)propanoate 1-28,
sodium (S)-3-(3-(1,5-dimethyl-4-oxido-2-oxo-1,2-dihydropyridin-3-yl)ureido)-3-(3-(3-methylbenzyl)phenyl)propanoate 1-29,
sodium (S)-3-(3-(1,5-dimethyl-4-oxido-2-oxo-1,2-dihydropyridin-3-yl)ureido)-3-(3-(4-methylbenzyl)phenyl)propanoate 1-30,
sodium (S)-3-(3-(1,6-dimethyl-4-oxido-2-oxo-1,2-dihydropyridin-3-yl)ureido)-3-(4-(2-methoxyphenoxy)phenyl)propanoate 2-11,
sodium (S)-3-(3-(1,6-dimethyl-4-oxido-2-oxo-1,2-dihydropyridin-3-yl)ureido)-3-(4-(3-methoxyphenoxy)phenyl)propanoate 2-12,
sodium (S)-3-(3-(1,6-dimethyl-4-oxido-2-oxo-1,2-dihydropyridin-3-yl)ureido)-3-(3-(p-tolyloxy)phenyl)propanoate 2-13,
sodium (S)-3-(3-(1,6-dimethyl-4-oxido-2-oxo-1,2-dihydropyridin-3-yl)ureido)-3-(3-(2-methylbenzyl)phenyl)propanoate 2-14,
sodium (S)-3-(3-(1,6-dimethyl-4-oxido-2-oxo-1,2-dihydropyridin-3-yl)ureido)-3-(5-(2-methylbenzyl)thiophen-2-yl)propanoate 2-15,
sodium (S)-3-(3-(difluoro(o-tolyl)methyl)phenyl)-3-(3-(1-methyl-4-oxido-2-oxo-1,2-dihydropyridin-3-yl)ureido)propanoate 3-65,
sodium (R)-3-(3-(difluoro(o-tolyl)methyl)phenyl)-3-(3-(1-methyl-4-oxido-2-oxo-1,2-dihydropyridin-3-yl)ureido)propanoate 3-66,
sodium (S)-3-(3-(1-methyl-4-oxido-2-oxo-1,2-dihydropyridin-3-yl)ureido)-3-(3-(o-tolyloxy)phenyl)propanoate 3-67,
sodium (S)-3-(3-(2-methoxyphenoxy)phenyl)-3-(3-(1-methyl-4-oxido-2-oxo-1,2-dihydropyridin-3-yl)ureido)propanoate 3-68,
sodium (S)-3-(3-(2-chlorophenoxy)phenyl)-3-(3-(1-methyl-4-oxido-2-oxo-1,2-dihydropyridin-3-yl)ureido)propanoate 3-69,
sodium (S)-3-(3-(5-fluoro-2-methylbenzyl)phenyl)-3-(3-(1-methyl-4-oxido-2-oxo-1,2-dihydropyridin-3-yl)ureido)propanoate 3-70,
sodium (S)-3-(3-(1-methyl-4-oxido-2-oxo-1,2-dihydropyridin-3-yl)ureido)-3-(3-phenoxyphenyl)propanoate 3-71,
sodium (S)-3-(4-(2-methoxyphenoxy)phenyl)-3-(3-(1-methyl-4-oxido-2-oxo-1,2-dihyopriddin-3-yl)ureido)propanoate 3-72,
sodium (S)-3-(4-(3-methoxyphenoxy)phenyl)-3-(3-(1-methyl-4-oxido-2-oxo-1,2-di hydropyridin-3-yl)ureido)propanoate 3-73,
sodium (S)-3-(3-(1-methyl-4-oxido-2-oxo-1,2-dihydropyridin-3-yl)ureido)-3-(4-(o-tolyloxy)phenyl)propanoate 3-74,
sodium (S)-3-(3-(1-methyl-4-oxido-2-oxo-1,2-dihydropyridin-3-yl)ureido)-3-(4-(p-tolyloxy)phenyl)propanoate 3-75,
sodium (S)-3-(4-benzylphenyl)-3-(3-(1-methyl-4-oxido-2-oxo-1,2-dihydropyridin-3-yl)ureido)propanoate 3-76,
sodium (S)-3-(3-(1-methyl-4-oxido-2-oxo-1,2-dihydropyridin-3-yl)ureido)-3-(4-(2-methylbenzyl)phenyl)propanoate 3-77,
sodium (S)-3-(3-(1-methyl-4-oxido-2-oxo-1,2-dihydropyridin-3-yl)ureido)-3-(4-(3-methylbenzyl)phenyl)propanoate 3-78,
sodium (S)-3-(3-(1-methyl-4-oxido-2-oxo-1,2-dihydropyridin-3-yl)ureido)-3-(4-(4-methylbenzyl)phenyl)propanoate 3-79,
sodium (S)-3-(3-(2-ethylbenzyl)phenyl)-3-(3-(1-methyl-4-oxido-2-oxo-1,2-dihydropyridin-3-yl)ureido)propanoate 3-80,
sodium (S)-3-(3-(1-methyl-4-oxido-2-oxo-1,2-dihydropyridin-3-yl)ureido)-3-(3-(2-methylbenzyl)phenyl)propanoate 3-81,
sodium (S)-3-(3-(1-methyl-4-oxido-2-oxo-1,2-dihydropyridin-3-yl)ureido)-3-(3-(4-methylbenzyl)phenyl)propanoate 3-82,
sodium (S)-3-(3-(1-methyl-4-oxido-2-oxo-1,2-dihydropyridin-3-yl)ureido)-3-(3-(m-tolyloxy)phenyl)propanoate 3-84,
sodium (S)-3-(3-(1-methyl-4-oxido-2-oxo-1,2-dihydropyridin-3-yl)ureido)-3-(3-(p-tolyloxy)phenyl)propanoate 3-85,
sodium (S)-3-(3-(2,4-difluorophenoxy)phenyl)-3-(3-(1-methyl-4-oxido-2-oxo-1,2-dihydropyridin-3-yl)ureido)propanoate 3-86,
sodium (S)-3-(3-(2,6-dimethylphenoxy)phenyl)-3-(3-(1-methyl-4-oxido-2-oxo-1,2-dihydropyridin-3-yl)ureido)propanoate 3-87,
sodium (S)-3-(3-(1-methyl-4-oxido-2-oxo-1,2-dihydropyridin-3-yl)ureido)-3-(3-(2-(trifluoromethyl)benzyl)phenyl)propanoate 3-88,
sodium (S)-3-(3-(1-methyl-4-oxido-2-oxo-1,2-dihydropyridin-3-yl)ureido)-3-(3-(3-(trifluoromethyl)benzyl)phenyl)propanoate 3-89,
sodium (S)-3-(3-(1-methyl-4-oxido-2-oxo-1,2-dihydropyridin-3-yl)ureido)-3-(3-(4-(trifluoromethyl)benzyl)phenyl)propanoate 3-90,
sodium (S)-3-(3-(2-(difluoromethoxy)benzyl)phenyl)-3-(3-(1-methyl-4-oxido-2-oxo-1,2-dihydropyridin-3-yl)ureido)propanoate 3-91,
sodium (S)-3-(3-(2-methoxybenzyl)phenyl)-3-(3-(1-methyl-4-oxido-2-oxo-1,2-dihydropyridin-3-yl)ureido)propanoate 3-92,
sodium (S)-3-(3-(2-fluorobenzyl)phenyl)-3-(3-(1-methyl-4-oxido-2-oxo-1,2-dihydropyridin-3-yl)ureido)propanoate 3-93, sodium (S)-3-(3-(2,6-dimethylbenzyl)phenyl)-3-(3-(1-methyl-4-oxido-2-oxo-1,2-di hydropyridin-3-yl)ureido)propanoate 3-94, sodium (S)-3-(3-(1-methyl-4-oxido-2-oxo-1,2-dihydropyridin-3-yl)ureido)-3-(5-(2-methylbenzyl)thiophen-2-yl)propanoate 3-95, sodium (S)-3-(5-benzylthiophen-2-yl)-3-(3-(1-methyl-4-oxido-2-oxo-1,2-dihydropyridin-3-yl)ureido)propanoate 3-96.

Provided herein are compounds and pharmaceutical compositions thereof that are derivatives of propanoic acid. Particularly, these compounds may comprise derivatives of diphenylether propanoates and diphenylmethane propanoates such as, but not limited to, those compounds described in the Examples. These compounds encompass their pharmaceutically acceptable salts and/or their stereoisomers.

As is known in the art, pharmaceutical compositions may comprise known carriers, excipients, diluents, etc, for example, saline, a buffer, an oil, or a powder. The pharmaceutical compositions may delivered in a vehicle such as, but not limited to, a spray, a liposome, a nanoparticle, a microparticle, a microcapsule, a nanosuspension, a microsuspension, or a hydrogel.

The compounds and pharmaceutical compositions disclosed herein are useful as therapeutics and prophylactics against pathophysiological conditions in a subject in need of such treatment. The compounds and pharmaceutical composition may be administered one or more times to achieve a therapeutic effect. The compounds and pharmaceutical composition may be administered with other therapeutics for a particular pathophysiological condition. As is known in the art, the skilled person is well-able to determine dose, dosage regimens and routes of administration depending on the condition to be treated and the subject requiring treatment.

For example, treatment may be associated with inhibiting the binding of $\alpha_4\beta_1$ integrin. Representative examples of a pathophysiological condition that might be treated by the inhibition of an α4, binding include, but are not limited to, atherosclerosis, rheumatoid arthritis, asthma, allergy, multiple sclerosis, lupus, inflammatory bowel disease, graft rejection, contact hypersensitivity, dry eye, hematopoietic stem cell transplant therapy, diabetes, stroke, pulmonary arterial hypertension, sickle cell disease and cancer. In addition to being found on some white blood cells, α4 integrins are also found on various cancer cells, including leukemia, melanoma, lymphoma and sarcoma cells. It has been suggested that cell adhesion involving α4 integrins may be involved in the metastasis of certain cancers. Inhibitors of α4 integrins binding may, therefore, also be useful in the treatment of some forms of cancer.

The following examples are given for the purpose of illustrating various embodiments of the invention and are not meant to limit the present invention in any fashion.

Example 1

Synthesis of sodium 3-(3-(1,5-dimethyl-4-oxido-2-oxo-1,2-dihydropyridin-3-yl)ureido)-3-(3-phenoxyphenyl)propanoate (1-21)

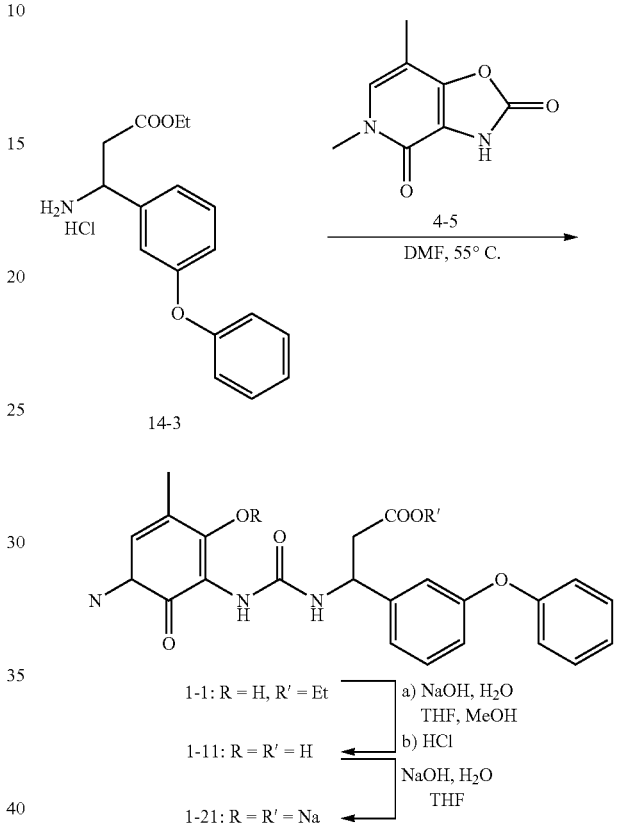

Step One: A suspension of 14-3 (153 mg, 0.54 mmol) and 4-5 (92 mg, 0.51 mmol) in DMF (1 mL) under a dry nitrogen atmosphere was heated to 55° C. overnight, cooled to room temperature and then diluted with water. The resulting mixture was extracted with dichloromethane three times and the combined organic layers were dried over MgSO$_4$ and filtered. The filtrate was concentrated under reduced pressure and the resulting residue was purified by silica gel chromatography, eluting with a gradient of 15 to 55% ethyl acetate in hexanes to give racemic ethyl 3-(3-(4-hydroxy-1,5-dimethyl-2-oxo-1,2-dihydropyridin-3-yl)ureido)-3-(3-phenoxyphenyl)propanoate (1-1, 64 mg).

In general, the temperature for this transformation was varied from 50 to 90° C. without a significant difference in the outcome. The progress of the reaction was monitored by TLC to ensure completion and the time and temperature was adjusted as needed.

By the procedure of Step One, use of the (S)-enantiomer of 14-3 yielded (S)-ethyl 3-(3-(4-hydroxy-1,5-dimethyl-2-oxo-1,2-dihydropyridin-3-yl)ureido)-3-(3-phenoxy phenyl) propanoate 1-2. Likewise, the reaction of other (S)-ethyl 3-aminopropanoate analogs with compound 4-5 also was used for the preparation of the following compounds.

| Name | Structure |
|---|---|
| ethyl 3-(3-(4-hydroxy-1,5-dimethyl-2-oxo-1,2-dihydropyridin-3-yl)ureido)-3-(3-phenoxyphenyl)propanoate 1-1 | 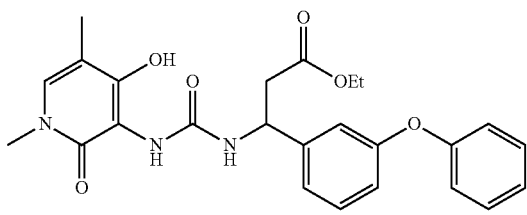 |
| ethyl (S)-3-(3-(4-hydroxy-1,5-dimethyl-2-oxo-1,2-dihydropyridin-3-yl)ureido)-3-(3-phenoxyphenyl)propanoate 1-2 | 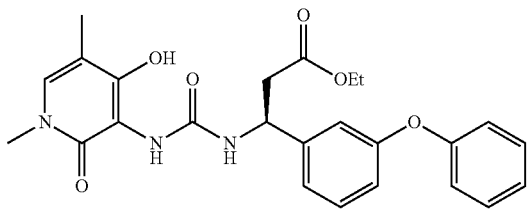 [SMILES: CCOC(=O)C[C@H](NC(=O)Nc1c(O)c(C)cn(C)c1=O)c1cccc(Cc2ccccc2)c1] |
| ethyl (S)-3-(3-benzylphenyl)-3-(3-(4-hydroxy-1,5-dimethyl-2-oxo-1,2-dihydropyridin-3-yl)ureido)propanoate 1-3 | 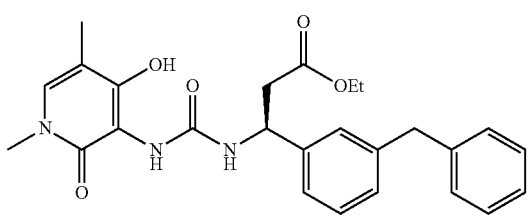 |
| ethyl 3-(3-(2-chlorobenzyl)phenyl)-3-(3-(4-hydroxy-1,5-dimethyl-2-oxo-1,2-dihydropyridin-3-yl)ureido)propanoate 1-4 | 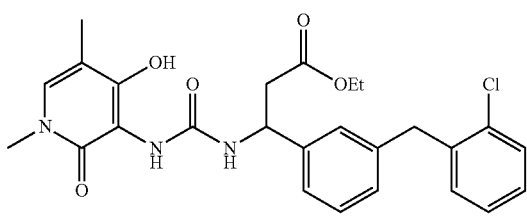 |
| ethyl 3-(3-(3-chlorobenzyl)phenyl)-3-(3-(4-hydroxy-1,5-dimethyl-2-oxo-1,2-dihydropyridin-3-yl)ureido)propanoate 1-5 | 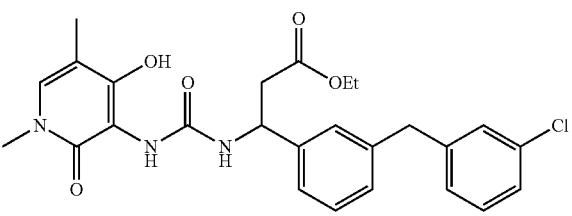 [SMILES: CCOC(=O)CC(NC(=O)Nc1c(O)c(C)cn(C)c1=O)c1cccc(Cc2cccc(Cl)c2)c1] |
| ethyl 3-(3-(4-chlorobenzyl)phenyl)-3-(3-(4-hydroxy-1,5-dimethyl-2-oxo-1,2-dihydropyridin-3-yl)ureido)propanoate 1-6 | 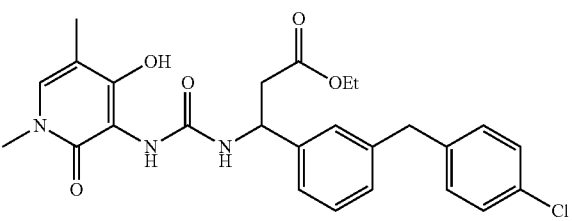 |
| ethyl (S)-3-(4-(2-chlorobenzyl)phenyl)-3-(3-(4-hydroxy-1,5-dimethyl-2-oxo-1,2-dihydropyridin-3-yl)ureido)propanoate 1-7 | 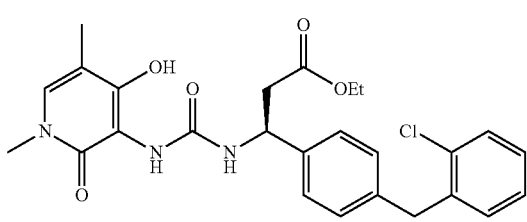 |

| Name | Structure |
|---|---|
| ethyl (S)-3-(3-(4-hydroxy-1,5-dimethyl-2-oxo-1,2-dihydropyridin-3-yl)ureido)-3-(3-(2-methylbenzyl)phenyl)propanoate 1-8 | 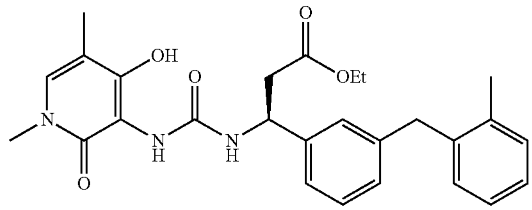 [SMILES: CCOC(=O)C[C@H](NC(=O)Nc1c(O)c(C)cn(C)c1=O)c1cccc(Cc2ccccc2C)c1] |
| ethyl (S)-3-(3-(4-hydroxy-1,5-dimethyl-2-oxo-1,2-dihydropyridin-3-yl)ureido)-3-(3-(3-methylbenzyl)phenyl)propanoate 1-9 | 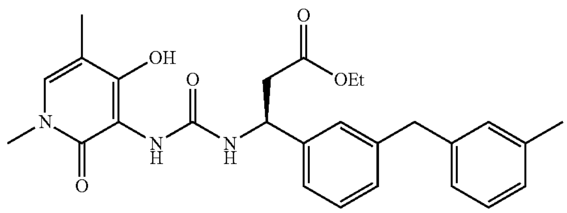 |
| ethyl (S)-3-(3-(4-hydroxy-1,5-dimethyl-2-oxo-1,2-dihydropyridin-3-yl)ureido)-3-(3-(4-methylbenzyl)phenyl)propanoate 1-10 | 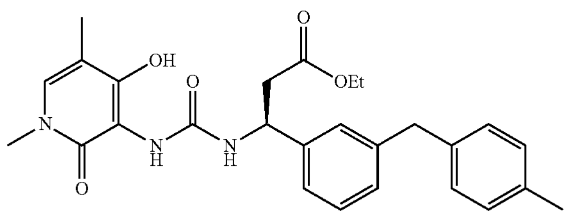 |

Step Two: To a solution of 1-1 (49.5 mg, 0.106 mmol) in THF (1 mL) at room temperature sodium hydroxide (2 N, 0.53 mL, 1.06 mmol) and methanol (0.5 mL) were added. The mixture was stirred for 2 hours, and the organic solvents were removed on the rotary evaporator. The remaining aqueous solution was diluted with water, and extracted with ether. The aqueous layer was acidified with HCl (2 N) and extracted with ethyl acetate. The ethyl acetate layer was washed with brine, dried, filtered, and concentrated to give 3-(3-(4-hydroxy-1,5-dimethyl-2-oxo-1,2-dihydropyridin-3-yl)ureido)-3-(3-phenoxyphenyl)propanoic acid (1-11, 42.8 mg).

This procedure was also performed without the aid of methanol as a co-solvent. In addition, this procedure was also carried out using acetonitrile in place of THF, without the aid of methanol as a co-solvent, with stirring overnight. The procedure could also be accomplished using methanol without THF. This variation was used to prepare (S)-3-(3-(4-hydroxy-1,5-dimethyl-2-oxo-1,2-dihydropyridin-3-yl)ureido)-3-(3-(2-methylbenzyl)phenyl)propanoic acid 1-19.

Likewise, in analogy with this procedure, the hydrolysis reaction of other ethyl 3-aminopropanoate analogs to free carboxylic acids was also used for the preparation of additional compounds listed below.

| Name | Structure |
|---|---|
| 3-(3-(4-hydroxy-1,5-dimethyl-2-oxo-1,2-dihydropyridin-3-yl)ureido)-3-(3-phenoxyphenyl)propanoic acid 1-11 | 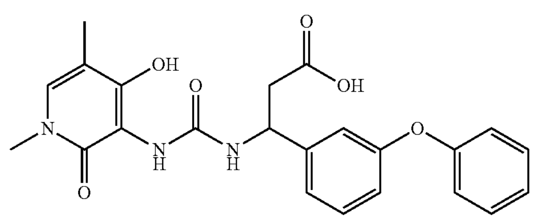 [SMILES: Cc1cn(C)c(=O)c(NC(=O)NC(CC(=O)O)c2cccc(Oc3ccccc3)c2)c1O] |
| (S)-3-(3-(4-hydroxy-1,5-dimethyl-2-oxo-1,2-dihydropyridin-3-yl)ureido)-3-(3-phenoxyphenyl)propanoic acid 1-12 | 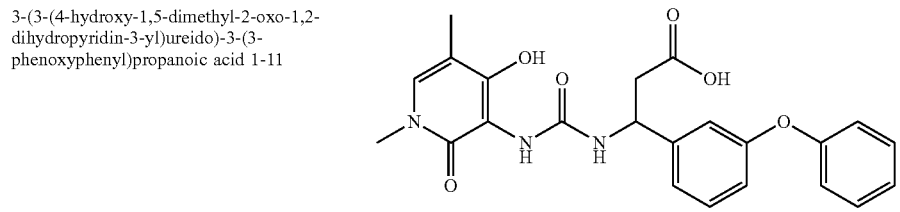 |

(S)-3-(3-benzylphenyl)-3-(3-(4-hydroxy-1,5-dimethyl-2-oxo-1,2-dihydropyridin-3-yl)ureido)propanoic acid 1-13

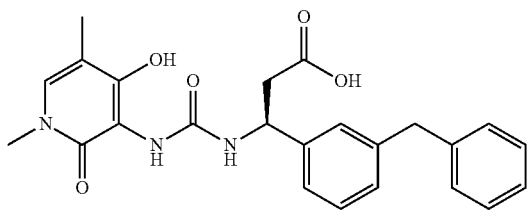 [SMILES: Cc1cn(C)c(=O)c(NC(=O)N[C@@H](CC(=O)O)c2cccc(Cc3ccccc3)c2)c1O]

3-(3-(2-chlorobenzyl)phenyl)-3-(3-(4-hydroxy-1,5-dimethyl-2-oxo-1,2-dihydropyridin-3-yl)ureido)propanoic acid 1-14

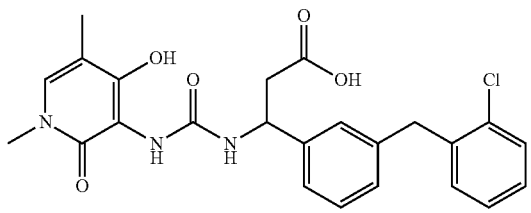

3-(3-(3-chlorobenzyl)phenyl)-3-(3-(4-hydroxy-1,5-dimethyl-2-oxo-1,2-dihydropyridin-3-yl)ureido)propanoic acid 1-15

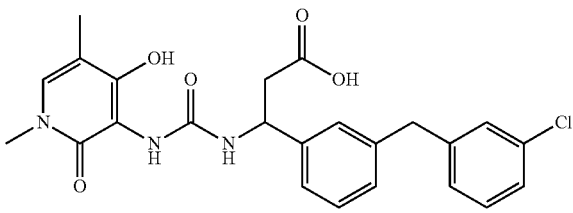 [SMILES: Cc1cn(C)c(=O)c(NC(=O)NC(CC(=O)O)c2cccc(Cc3cccc(Cl)c3)c2)c1O]

3-(3-(4-chlorobenzyl)phenyl)-3-(3-(4-hydroxy-1,5-dimethyl-2-oxo-1,2-dihydropyridin-3-yl)ureido)propanoic acid 1-16

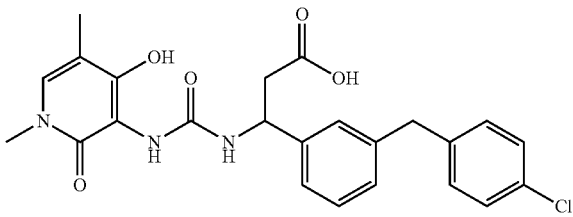 [SMILES: Cc1cn(C)c(=O)c(NC(=O)NC(CC(=O)O)c2cccc(Cc3ccc(Cl)cc3)c2)c1O]

(S)-3-(4-(2-chlorobenzyl)phenyl)-3-(3-(4-hydroxy-1,5-dimethyl-2-oxo-1,2-dihydropyridin-3-yl)ureido)propanoic acid 1-17

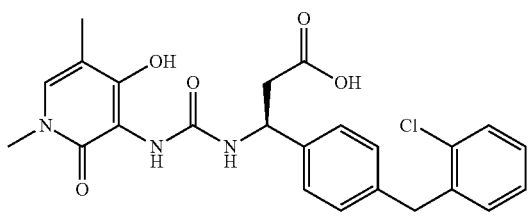

(S)-3-(3-(4-hydroxy-1,5-dimethyl-2-oxo-1,2-dihydropyridin-3-yl)ureido)-3-(3-(3-methylbenzyl)phenyl)propanoic acid 1-18

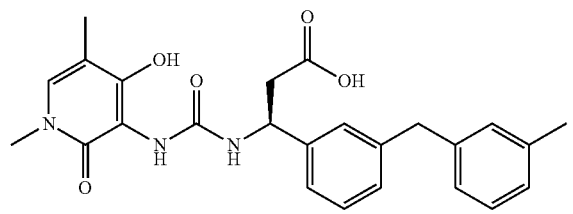

(S)-3-(3-(4-hydroxy-1,5-dimethyl-2-oxo-1,2-dihydropyridin-3-yl)ureido)-3-(3-(2-methylbenzyl)phenyl)propanoic acid 1-19

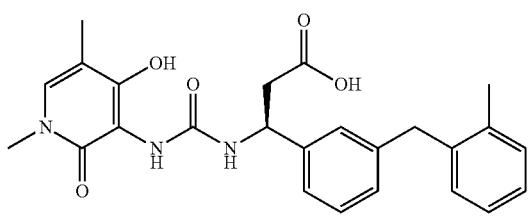

| | |
|---|---|
| (S)-3-(3-(4-hydroxy-1,5-dimethyl-2-oxo-1,2-dihydropyridin-3-yl)ureido)-3-(3-(4-methylbenzyl)phenyl)propanoic acid 1-20 | 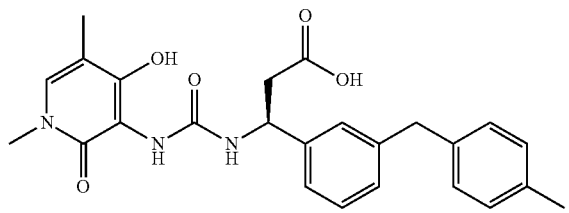 |

Step Three: To a solution of 1-11 (42.8 mg, 0.098 mmol) in inhibitor free THF (1 mL), aqueous sodium hydroxide (0.1000 N, 1.96 mL, 0.196 mmol) was added. The mixture was heated briefly to 40° C. to give a homogeneous mixture, and the THF was removed by rotary evaporation. The mixture was diluted with deionized water, then frozen in a dry ice/acetone bath and lyophilized to give sodium 3-(3-(1,5-dimethyl-4-oxido-2-oxo-1,2-dihydropyridin-3-yl)ureido)-3-(3-phenoxyphenyl)propanoate (1-21; MS [M+H$^+$]$^+$: 437.95). Likewise, in analogy, this procedure was also used as well to prepare the other 3-aminopropanoic acid sodium salts listed below.

| | |
|---|---|
| sodium 3-(3-(1,5-dimethyl-4-oxido-2-oxo-1,2-dihydropyridin-3-yl)ureido)-3-(3-phenoxyphenyl)propanoate 1-21<br>MS [M + H$^+$]$^+$: 437.95; a4b1 IC$_{50}$ = <200 nM: a4b7 IC$_{50}$ = nd | 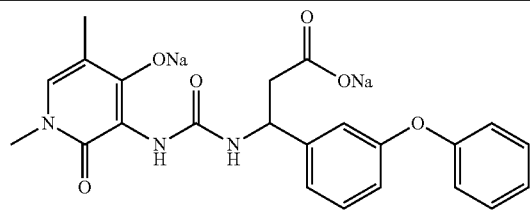 |
| sodium (S)-3-(3-(1,5-dimethyl-4-oxido-2-oxo-1,2-dihydropyridin-3-yl)ureido)-3-(3-phenoxyphenyl)propanoate 1-22<br>MS [M + H$^+$]$^+$: 437.95; a4b1 IC$_{50}$ = <200 nM: a4b7 IC$_{50}$ = nd | 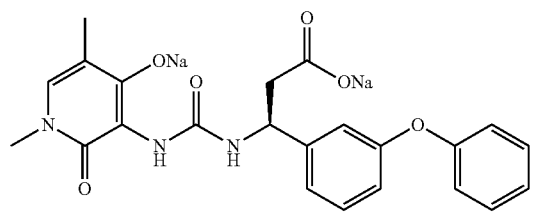 |
| sodium (S)-3-(3-benzylphenyl)-3-(3-(1,5-dimethyl-4-oxido-2-oxo-1,2-dihydropyridin-3-yl)ureido)propanoate 1-23<br>MS [M + H$^+$]$^+$: 436.12; a4b1 IC$_{50}$ = <200 nM: a4b7 IC$_{50}$ = nd | 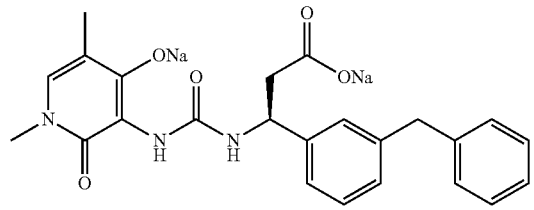 |
| sodium 3-(3-(2-chlorobenzyl)phenyl)-3-(3-(1,5-dimethyl-4-oxido-2-oxo-1,2-dihydropyridin-3-yl)ureido)propanoate 1-24<br>MS [M + H$^+$]$^+$: 469.94; a4b1 IC$_{50}$ = <200 nM: a4b7 IC$_{50}$ = nd | 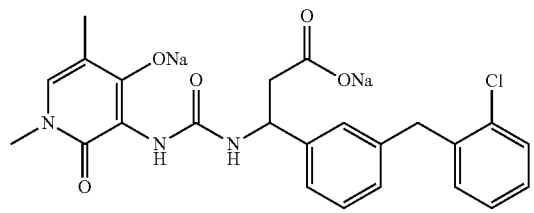 |

| | |
|---|---|
| sodium 3-(3-(3-chlorobenzyl)phenyl)-3-(3-(1,5-dimethyl-4-oxido-2-oxo-1,2-dihydropyridin-3-yl)ureido)propanoate 1-25 MS [M + H$^+$]$^+$: 469.92; a4b1 IC$_{50}$ = <200 nM; a4b7 IC$_{50}$ = nd | 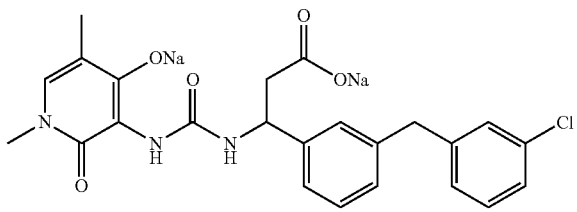 |
| sodium 3-(3-(4-chlorobenzyl)phenyl)-3-(3-(1,5-dimethyl-4-oxido-2-oxo-1,2-dihydropyridin-3-yl)ureido)propanoate 1-26 MS [M + H$^+$]$^+$: 469.95; a4b1 IC$_{50}$ = >200 nM; a4b7 IC$_{50}$ = nd | 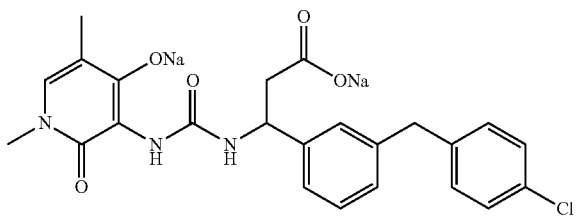 |
| sodium (S)-3-(4-(2-chlorobenzyl)phenyl)-3-(3-(4-hydroxy-1,5-dimethyl-2-oxo-1,2-dihydropyridin-3-yl)ureido)propanoate 1-27 MS [M + H$^+$]$^+$: 470.00; a4b1 IC$_{50}$ = >200 nM; a4b7 IC$_{50}$ = nd | 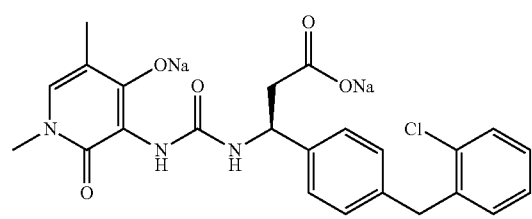 |
| sodium (S)-3-(3-(1,5-dimethyl-4-oxido-2-oxo-1,2-dihydropyridin-3-yl)ureido)-3-(3-(2-methylbenzyl)phenyl)propanoate 1-28 MS [M + H$^+$]$^+$: 450.08; a4b1 IC$_{50}$ = <20 nM; a4b7 IC$_{50}$ = nd | 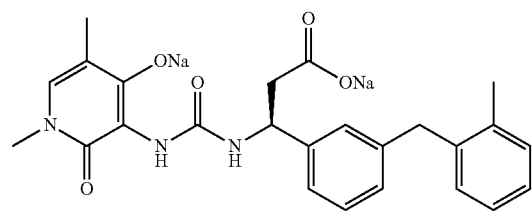 |
| sodium (S)-3-(3-(1,5-dimethyl-4-oxido-2-oxo-1,2-dihydropyridin-3-yl)ureido)-3-(3-(3-methylbenzyl)phenyl)propanoate 1-29 MS [M + H$^+$]$^+$: 449.95; a4b1 IC$_{50}$ = <200 nM; a4b7 IC$_{50}$ = nd | 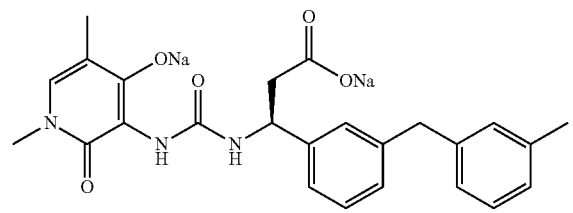 |
| sodium (S)-3-(3-(1,5-dimethyl-4-oxido-2-oxo-1,2-dihydropyridin-3-yl)ureido)-3-(3-(4-methylbenzyl)phenyl)propanoate 1-30 MS [M + H$^+$]$^+$: 449.96; a4b1 IC$_{50}$ = <200 nM; a4b7 IC$_{50}$ = nd | 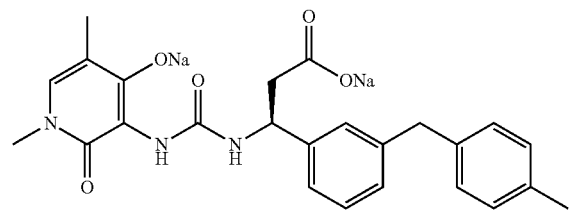 |

Example 2

Synthesis of sodium 3-(3-(1,5-dimethyl-4-oxido-2-oxo-1,2-dihydropyridin-3-yl)ureido)-3-(4-(2-methoxyphenoxy)phenyl)propanoate (2-11)

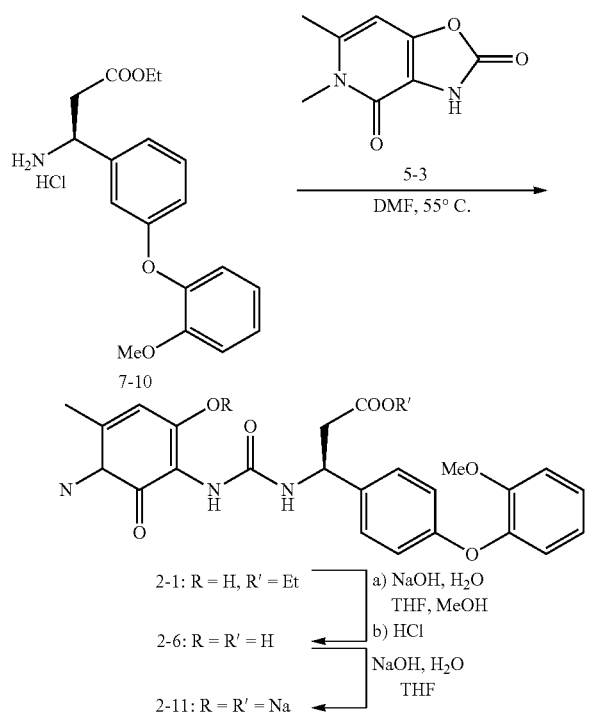

Step One: In analogy to Example 1, Step One, a suspension of 7-10 and 5-3 in DMF under a dry nitrogen atmosphere was heated to 55° C. overnight, cooled to room temperature and then diluted with water. The resulting mixture was extracted with dichloromethane three times and the combined organic layers were dried over $MgSO_4$ and filtered. The filtrate was concentrated under reduced pressure and the resulting residue was purified by silica gel chromatography, eluting with a gradient of 15 to 55% ethyl acetate in hexanes to give (S)-ethyl-3-(3-(4-hydroxy-1,6-dimethyl-2-oxo-1,2-dihydropyridin-3-yl)ureido)-3-(4-(2-methoxyphenoxy)phenyl)propanoate (2-1).

In general, the temperature for this transformation was varied from 50 to 90° C. without a significant difference in the outcome. The progress of the reaction was monitored by TLC to ensure completion and the time and temperature was adjusted as needed.

Likewise, the reaction of other (S)-ethyl 3-aminopropanoate analogs with compound 5-3 also was used for the preparation of the following compounds.

ethyl (S)-3-(3-(4-hydroxy-1,6-dimethyl-2-oxo-1,2-dihydropyridin-3-yl)ureido)-3-(4-(2-methoxyphenoxy)phenyl)propanoate 2-1

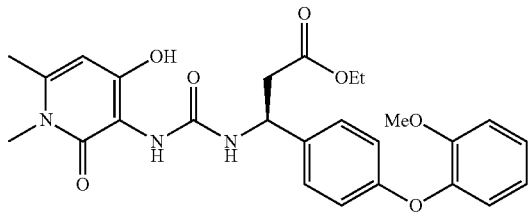

ethyl (S)-3-(3-(4-hydroxy-1,6-dimethyl-2-oxo-1,2-dihydropyridin-3-yl)ureido)-3-(4-(3-methoxyphenoxy)phenyl)propanoate 2-2

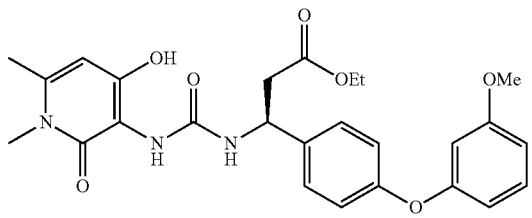 [SMILES: CCOC(=O)C[C@H](NC(=O)Nc1c(O)cc(C)n(C)c1=O)c1ccc(Oc2cccc(OC)c2)cc1]

ethyl (S)-3-(3-(4-hydroxy-1,6-dimethyl-2-oxo-1,2-dihydropyridin-3-yl)ureido)-3-(3-(p-tolyloxy)phenyl)propanoate 2-3

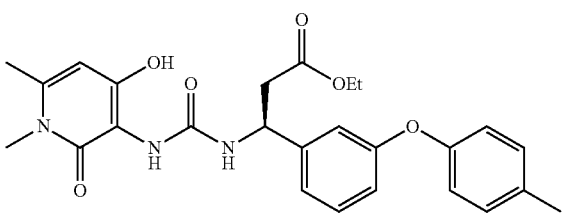

| | |
|---|---|
| ethyl (S)-3-(3-(4-hydroxy-1,6-dimethyl-2-oxo-1,2-dihydropyridin-3-yl)ureido)-3-(3-(2-methylbenzyl)phenyl)propanoate 2-4 | 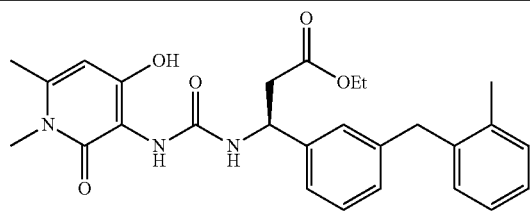 |
| ethyl (S)-3-(3-(4-hydroxy-1,6-dimethyl-2-oxo-1,2-dihydropyridin-3-yl)ureido)-3-(5-(2-methylbenzyl)thiophen-2-yl)propanoate 2-5 | 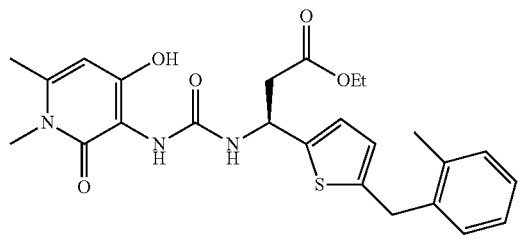 |

Step Two: In analogy to Example 1, Step Two, to a solution of 2-1 in THF at room temperature was added sodium hydroxide (2 N) and methanol. The mixture was stirred for 2 hours, and the organic solvents were removed on the rotary evaporator. The remaining aqueous solution was diluted with water, and extracted with ether. The aqueous layer was acidified with HCl (2 N) and extracted with ethyl acetate. The ethyl acetate layer was washed with brine, dried, filtered, and concentrated to give (S)-3-(3-(4-hydroxy-1,6-dimethyl-2-oxo-1,2-dihydropyridin-3-yl)ureido)-3-(4-(2-methoxyphenoxy)phenyl)propanoic acid 2-6.

Likewise, in analogy with this procedure, the hydrolysis reaction of other ethyl 3-aminopropanoate analogs to free carboxylic acids was also used for the preparation of additional compounds listed below.

| | |
|---|---|
| (S)-3-(3-(4-hydroxy-1,6-dimethyl-2-oxo-1,2-dihydropyridin-3-yl)ureido)-3-(4-(2-methoxyphenoxy)phenyl)propanoic acid 2-6 | 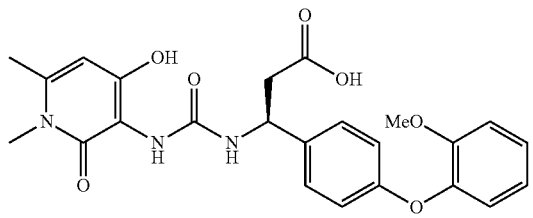 [SMILES: COc1ccccc1Oc1ccc([C@H](CC(=O)O)NC(=O)Nc2c(O)cc(C)n(C)c2=O)cc1] |
| (S)-3-(3-(4-hydroxy-1,6-dimethyl-2-oxo-1,2-dihydropyridin-3-yl)ureido)-3-(4-(3-methoxyphenoxy)phenyl)propanoic acid 2-7 | 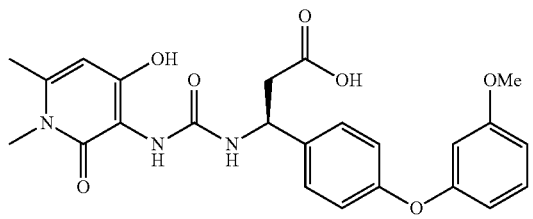 [SMILES: COc1cccc(Oc2ccc([C@H](CC(=O)O)NC(=O)Nc3c(O)cc(C)n(C)c3=O)cc2)c1] |
| (S)-3-(3-(4-hydroxy-1,6-dimethyl-2-oxo-1,2-dihydropyridin-3-yl)ureido)-3-(3-(p-tolyloxy)phenyl)propanoic acid 2-8 | 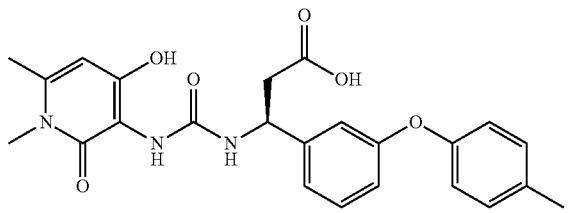 |
| (S)-3-(3-(4-hydroxy-1,6-dimethyl-2-oxo-1,2-dihydropyridin-3-yl)ureido)-3-(3-(2-methylbenzyl)phenyl)propanoic acid 2-9 | 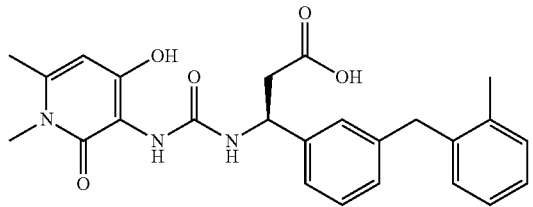 [SMILES: Cc1ccccc1Cc1cccc([C@H](CC(=O)O)NC(=O)Nc2c(O)cc(C)n(C)c2=O)c1] |

| | |
|---|---|
| (S)-3-(3-(4-hydroxy-1,6-dimethyl-2-oxo-1,2-dihydropyridin-3-yl)ureido)-3-(5-(2-methylbenzyl)thiophen-2-yl)propanoic acid 2-10 | 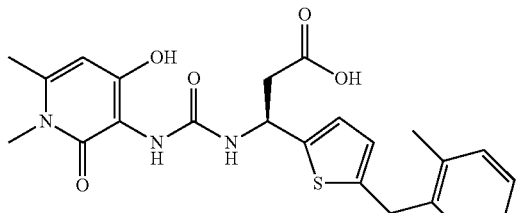 |

Step Three: In analogy to Example 1, Step Three, to a solution of 2-6 in inhibitor free THF, aqueous sodium hydroxide (0.1000 N) was added. The mixture was heated briefly to 40° C. to give a homogeneous mixture, and the THF was removed by rotary evaporation. The mixture was diluted with deionized water, then frozen in a dry ice/acetone bath and lyophilized to give sodium sodium (S)-3-(3-(1,6-dimethyl-4-oxido-2-oxo-1,2-dihydropyridin-3-yl)ureido)-3-(4-(2-methoxyphenoxy)phenyl)propanoate 2-11.

Likewise, in analogy, this procedure was also used to prepare sodium other 3-aminopropanoic acid sodium salts listed below.

| | |
|---|---|
| sodium (S)-3-(3-(1,6-dimethyl-4-oxido-2-oxo-1,2-dihydropyridin-3-yl)ureido)-3-(4-(2-methoxyphenoxy)phenyl)propanoate 2-11, MS [M + H⁺]⁺: 437.95; a4b1 IC$_{50}$ = <200 nM; a4b7 IC$_{50}$ = nd | 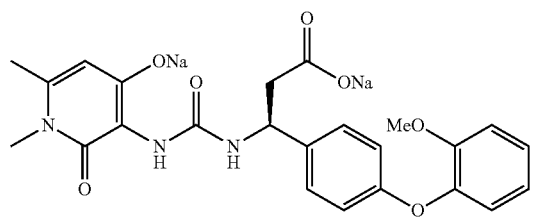 |
| sodium (S)-3-(3-(1,6-dimethyl-4-oxido-2-oxo-1,2-dihydropyridin-3-yl)ureido)-3-(4-(3-methoxyphenoxy)phenyl)propanoate 2-12, MS [M + H⁺]⁺: 468.18; a4b1 IC$_{50}$ = <200 nM; a4b7 IC$_{50}$ = nd | 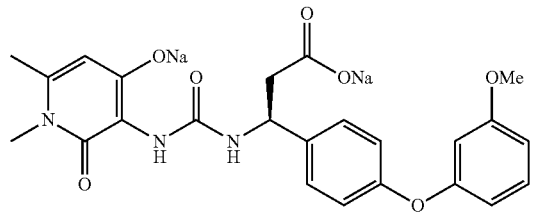 |
| sodium (S)-3-(3-(1,6-dimethyl-4-oxido-2-oxo-1,2-dihydropyridin-3-yl)ureido)-3-(3-(p-tolyloxy)phenyl)propanoate 2-13 MS [M + H⁺]⁺: 452.18; a4b1 IC$_{50}$ = na; a4b7 IC$_{50}$ = nd | 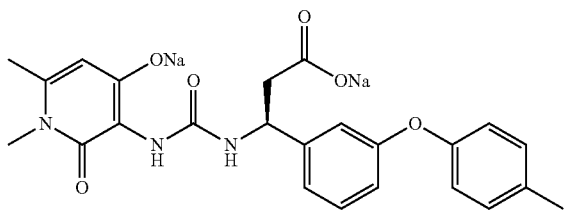 |
| sodium (S)-3-(3-(1,6-dimethyl-4-oxido-2-oxo-1,2-dihydropyridin-3-yl)ureido)-3-(3-(2-methylbenzyl)phenyl)propanoate 2-14 MS [M + H⁺]⁺: 450.03; a4b1 IC$_{50}$ = <20 nM; a4b7 IC$_{50}$ = nd | 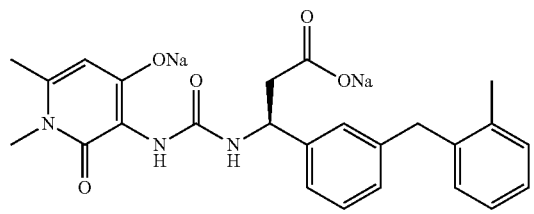 |
| sodium (S)-3-(3-(1,6-dimethyl-4-oxido-2-oxo-1,2-dihydropyridin-3-yl)ureido)-3-(5-(2-methylbenzyl)thiophen-2-yl)propanoate 2-15 MS [M + H⁺]⁺: 456.02; a4b1 IC$_{50}$ = 20 nM; a4b7 IC$_{50}$ = nd | 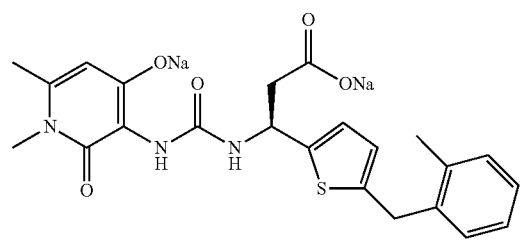 |

Example 3

Synthesis of Sodium (S)-3-(3-(difluoro(o-tolyl)methyl) phenyl)-3-(3-(1-methyl-4-oxido-2-oxo-1,2-dihydropyridin-3-yl)ureido)propanoate (1-64)

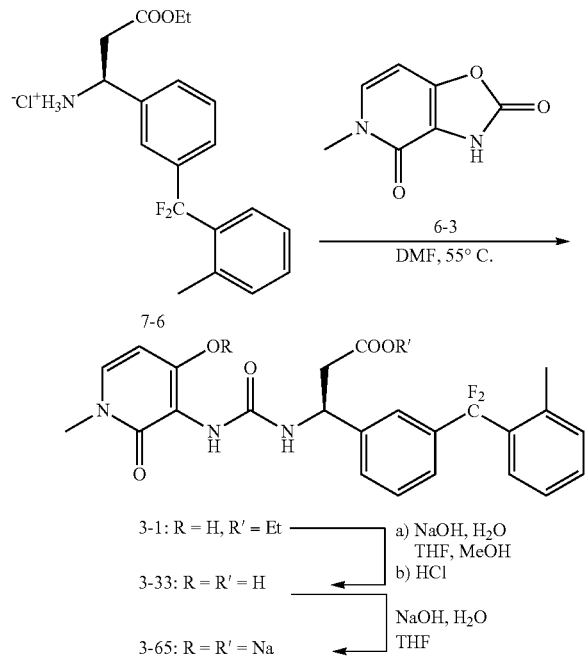

Step One: In analogy to Example 1, Step One, a suspension of 7-6 and 6-3 in DMF under a dry nitrogen atmosphere was heated to 55° C. overnight, cooled to room temperature and then diluted with water. The resulting mixture was extracted with dichloromethane three times and the combined organic layers were dried over MgSO$_4$ and filtered. The filtrate was concentrated under reduced pressure and the resulting residue was purified by silica gel chromatography, eluting with a gradient of 15 to 55% ethyl acetate in hexanes to give (S)-ethyl-3-(3-(difluoro(o-tolyl)methyl)phenyl)-3-(3-(4-hydroxy-1-methyl-2-oxo-1,2-dihydropyridin-3-yl)ureido)propanoate 3-1.

In general, the temperature for this transformation was varied from 50 to 90° C. without a significant difference in the outcome. The progress of the reaction was monitored by TLC to ensure completion and the time and temperature was adjusted as needed.

This reaction could also be conducted in the presence of a slight excess of N-methylmorpholine. This modification was used in all instances where the amine was isolated as a hydrochloride salt, but could also be used when using a freebase. This modification was used to prepare ethyl (S)-3-(3-(4-hydroxy-1-methyl-2-oxo-1,2-dihydropyridin-3-yl)ureido)-3-(3-(o-tolyloxy)phenyl)propanoate 3-26. Likewise, the reaction of other ethyl (S)-3-aminopropanoate analogs with compound 6-3 was also used for the preparation of the following compounds.

| | |
|---|---|
| ethyl (S)-3-(3-(difluoro(o-tolyl)methyl)phenyl)-3-(3-(4-hydroxy-1-methyl-2-oxo-1,2-dihydropyridin-3-yl)ureido)propanoate 3-1 | 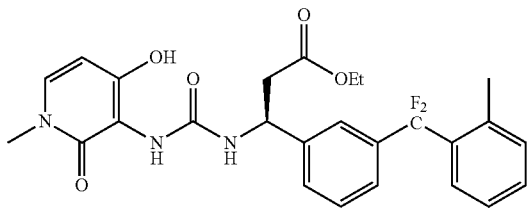 |
| ethyl (R)-3-(3-(difluoro(o-tolyl)methyl)phenyl)-3-(3-(4-hydroxy-1-methyl-2-oxo-1,2-dihydropyridin-3-yl)ureido)propanoate 3-2 | 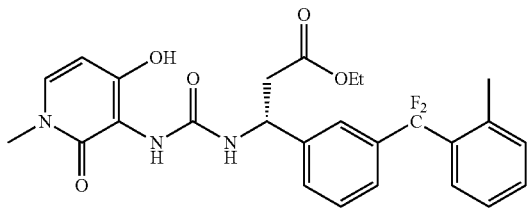 [SMILES: CCOC(=O)C[C@@H](NC(=O)Nc1c(O)ccn(C)c1=O)c1cccc(C(F)(F)c2ccccc2C)c1] |
| ethyl (S)-3-(3-(4-hydroxy-1-methyl-2-oxo-1,2-dihydropyridin-3-yl)ureido)-3-(3-phenoxyphenyl)propanoate 3-3 | 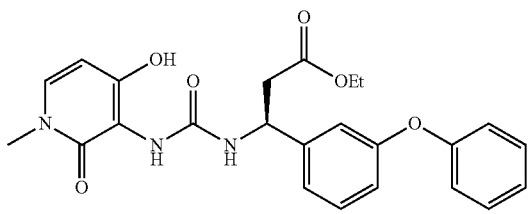 |

-continued ethyl (S)-3-(3-(4-hydroxy-1-methyl-2-oxo-1,2-dihydropyridin-3-yl)ureido)-3-(4-(2-methoxyphenoxy)phenyl)propanoate 3-4

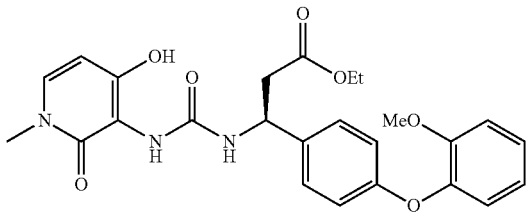 [SMILES: CCOC(=O)C[C@H](NC(=O)Nc1c(O)ccn(C)c1=O)c1ccc(Oc2ccccc2OC)cc1]

ethyl (S)-3-(3-(4-hydroxy-1-methyl-2-oxo-1,2-dihydropyridin-3-yl)ureido)-3-(4-(3-methoxyphenoxy)phenyl)propanoate 3-5

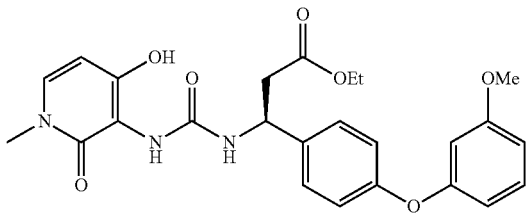

ethyl (S)-3-(3-(4-hydroxy-1-methyl-2-oxo-1,2-dihydropyridin-3-yl)ureido)-3-(4-(o-tolyloxy)phenyl)propanoate 3-6

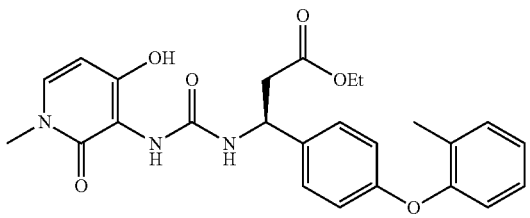 [SMILES: CCOC(=O)C[C@H](NC(=O)Nc1c(O)ccn(C)c1=O)c1ccc(Oc2ccccc2C)cc1]

ethyl (S)-3-(3-(4-hydroxy-1-methyl-2-oxo-1,2-dihydropyridin-3-yl)ureido)-3-(4-(p-tolyloxy)phenyl)propanoate 3-7

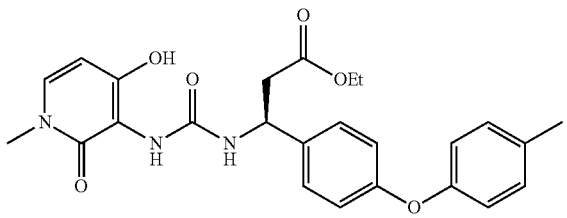

ethyl (S)-3-(4-benzylphenyl)-3-(3-(4-hydroxy-1-methyl-2-oxo-1,2-dihydropyridin-3-yl)ureido)propanoate 3-8

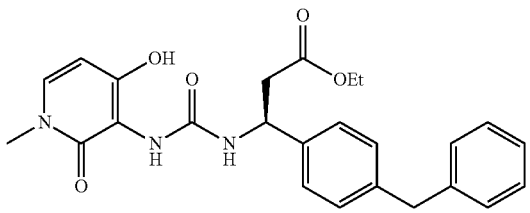

ethyl (S)-3-(3-(4-hydroxy-1-methyl-2-oxo-1,2-dihydropyridin-3-yl)ureido)-3-(4-(2-methylbenzyl)phenyl)propanoate 3-9

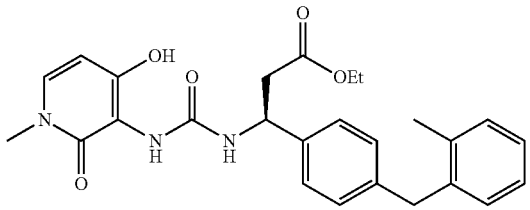 [SMILES: CCOC(=O)C[C@H](NC(=O)Nc1c(O)ccn(C)c1=O)c1ccc(Cc2ccccc2C)cc1]

ethyl (S)-3-(3-(4-hydroxy-1-methyl-2-oxo-1,2-dihydropyridin-3-yl)ureido)-3-(4-(3-methylbenzyl)phenyl)propanoate 3-10

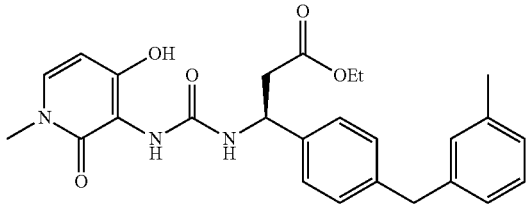

-continued ethyl (S)-3-(3-(4-hydroxy-1-methyl-2-oxo-1,2-dihydropyridin-3-yl)ureido)-3-(4-(4-methylbenzyl)phenyl)propanoate 3-11

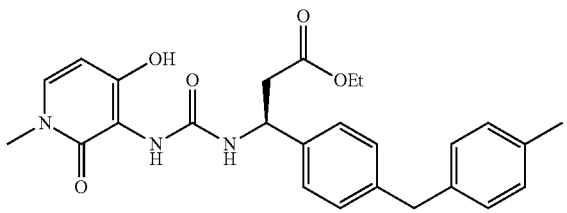

ethyl (S)-3-(3-(2-ethylbenzyl)phenyl)-3-(3-(4-hydroxy-1-methyl-2-oxo-1,2-dihydropyridin-3-yl)ureido)propanoate 3-12

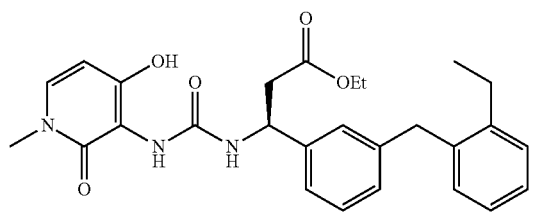 [SMILES: CCOC(=O)C[C@H](NC(=O)Nc1c(O)ccn(C)c1=O)c1cccc(Cc2ccccc2CC)c1]

ethyl (S)-3-(3-(4-hydroxy-1-methyl-2-oxo-1,2-dihydropyridin-3-yl)ureido)-3-(3-(2-methylbenzyl)phenyl)propanoate 3-13

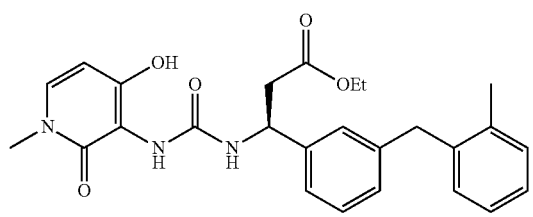 [SMILES: CCOC(=O)C[C@H](NC(=O)Nc1c(O)ccn(C)c1=O)c1cccc(Cc2ccccc2C)c1]

ethyl (S)-3-(3-(4-hydroxy-1-methyl-2-oxo-1,2-dihydropyridin-3-yl)ureido)-3-(3-(3-methylbenzyl)phenyl)propanoate 3-14

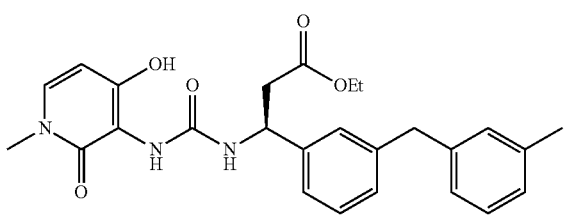

ethyl (S)-3-(3-(4-hydroxy-1-methyl-2-oxo-1,2-dihydropyridin-3-yl)ureido)-3-(3-(4-methylbenzyl)phenyl)propanoate 3-15

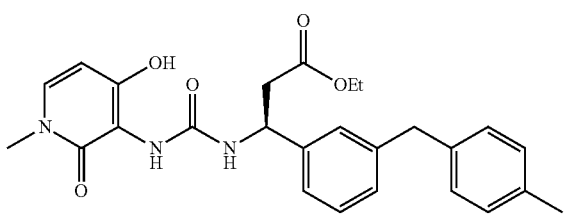

ethyl (S)-3-(3-(4-hydroxy-1-methyl-2-oxo-1,2-dihydropyridin-3-yl)ureido)-3-(3-(2-(trifluoromethyl)benzyl)phenyl)propanoate 3-16

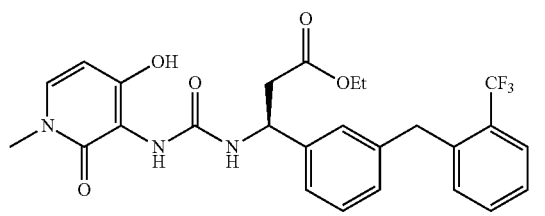 [SMILES: CCOC(=O)C[C@H](NC(=O)Nc1c(O)ccn(C)c1=O)c1cccc(Cc2ccccc2C(F)(F)F)c1]

ethyl (S)-3-(3-(4-hydroxy-1-methyl-2-oxo-1,2-dihydropyridin-3-yl)ureido)-3-(3-(3-(trifluoromethyl)benzyl)phenyl)propanoate 3-17

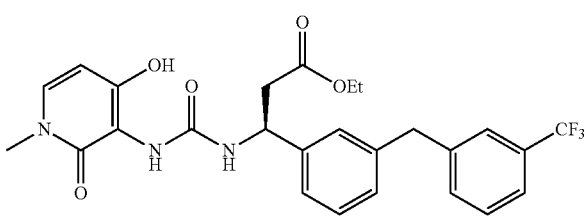 [SMILES: CCOC(=O)C[C@H](NC(=O)Nc1c(O)ccn(C)c1=O)c1cccc(Cc2cccc(C(F)(F)F)c2)c1]

| | |
|---|---|
| ethyl (S)-3-(3-(4-hydroxy-1-methyl-2-oxo-1,2-dihydropyridin-3-yl)ureido)-3-(3-(4-(trifluoromethyl)benzyl)phenyl)propanoate 3-18 | 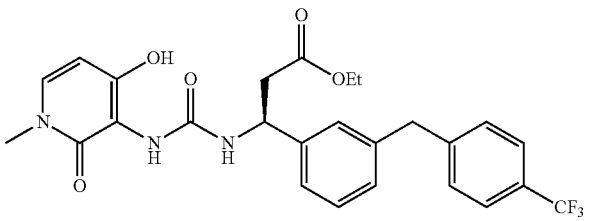 [SMILES: CCOC(=O)C[C@H](NC(=O)Nc1c(O)ccn(C)c1=O)c1cccc(Cc2ccc(C(F)(F)F)cc2)c1] |
| ethyl (S)-3-(3-(2-(difluoromethoxy)benzyl)phenyl)-3-(3-(4-hydroxy-1-methyl-2-oxo-1,2-dihydropyridin-3-yl)ureido)propanoate 3-19 | 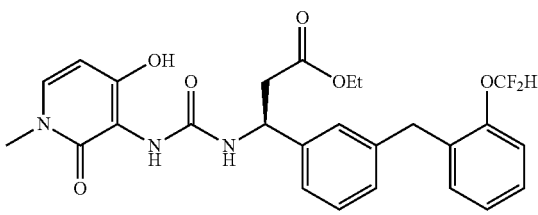 |
| ethyl (S)-3-(3-(4-hydroxy-1-methyl-2-oxo-1,2-dihydropyridin-3-yl)ureido)-3-(3-(2-methoxybenzyl)phenyl)propanoate 3-20 | 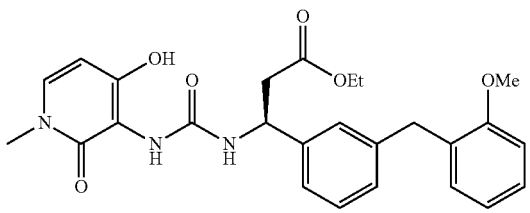 |
| ethyl (S)-3-(3-(2-fluorobenzyl)phenyl)-3-(3-(4-hydroxy-1-methyl-2-oxo-1,2-dihydropyridin-3-yl)ureido)propanoate 3-21 | 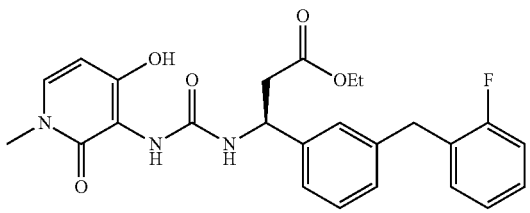 [SMILES: CCOC(=O)C[C@H](NC(=O)Nc1c(O)ccn(C)c1=O)c1cccc(Cc2ccccc2F)c1] |
| ethyl (S)-3-(3-(2,6-dimethylbenzyl)phenyl)-3-(3-(4-hydroxy-1-methyl-2-oxo-1,2-dihydropyridin-3-yl)ureido)propanoate 3-22 | 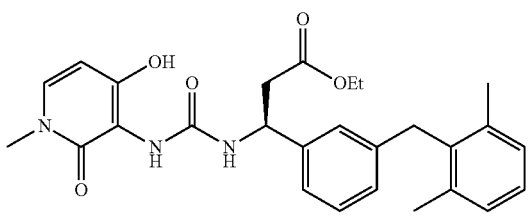 [SMILES: CCOC(=O)C[C@H](NC(=O)Nc1c(O)ccn(C)c1=O)c1cccc(Cc2c(C)cccc2C)c1] |
| ethyl (S)-3-(3-(5-fluoro-2-methylbenzyl)phenyl)-3-(3-(4-hydroxy-1-methyl-2-oxo-1,2-dihydropyridin-3-yl)ureido)propanoate 3-23 | 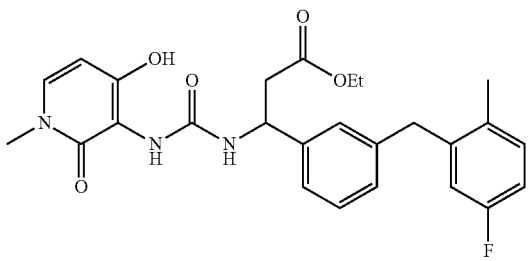 [SMILES: CCOC(=O)CC(NC(=O)Nc1c(O)ccn(C)c1=O)c1cccc(Cc2cc(F)ccc2C)c1] |
| ethyl (S)-3-(3-(4-hydroxy-1-methyl-2-oxo-1,2-dihydropyridin-3-yl)ureido)-3-(5-(2-methylbenzyl)thiophen-2-yl)propanoate 3-24 | 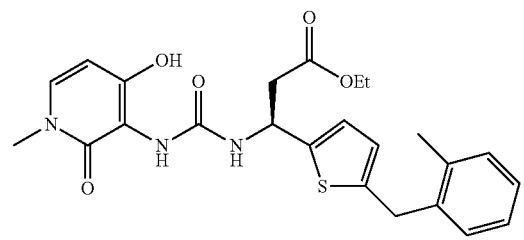 [SMILES: CCOC(=O)C[C@H](NC(=O)Nc1c(O)ccn(C)c1=O)c1ccc(Cc2ccccc2C)s1] |

-continued ethyl (S)-3-(5-benzylthiophen-2-yl)-3-(3-(4-hydroxy-1-methyl-2-oxo-1,2-dihydropyridin-3-yl)ureido)propanoate 3-25

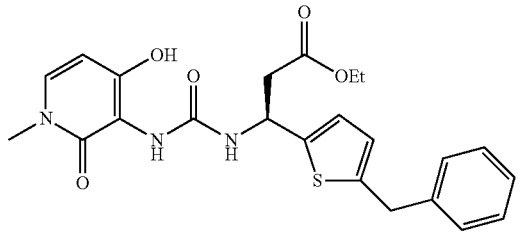

ethyl (S)-3-(3-(4-hydroxy-1-methyl-2-oxo-1,2-dihydropyridin-3-yl)ureido)-3-(3-(o-tolyloxy)phenyl)propanoate 3-26

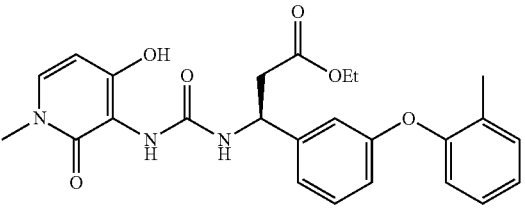 [SMILES: CCOC(=O)C[C@H](NC(=O)Nc1c(O)ccn(C)c1=O)c1cccc(Oc2ccccc2C)c1]

ethyl (S)-3-(3-(4-hydroxy-1-methyl-2-oxo-1,2-dihydropyridin-3-yl)ureido)-3-(3-(m-tolyloxy)phenyl)propanoate 3-27

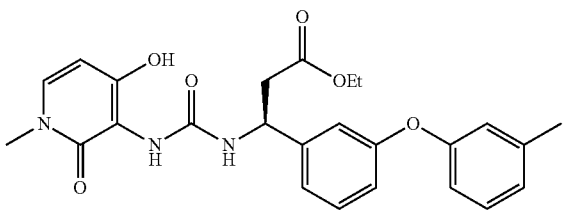

ethyl (S)-3-(3-(4-hydroxy-1-methyl-2-oxo-1,2-dihydropyridin-3-yl)ureido)-3-(3-(p-tolyloxy)phenyl)propanoate 3-28

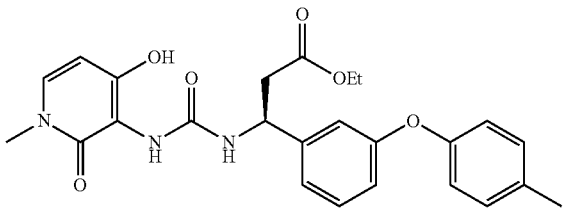

ethyl (S)-3-(3-(4-hydroxy-1-methyl-2-oxo-1,2-dihydropyridin-3-yl)ureido)-3-(3-(2-methoxyphenoxy)phenyl)propanoate 3-29

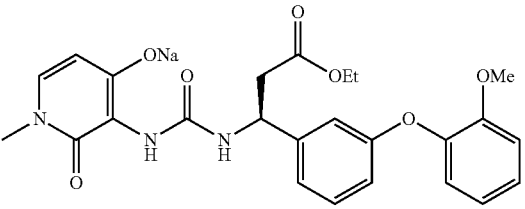

ethyl (S)-3-(3-(4-hydroxy-1-methyl-2-oxo-1,2-dihydropyridin-3-yl)ureido)-3-(3-(2-chlorophenoxy)phenyl)propanoate 3-30

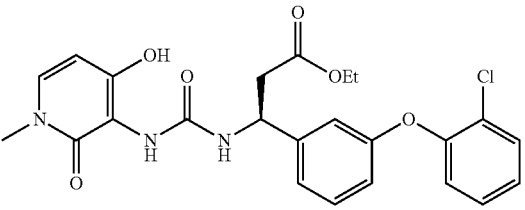 [SMILES: CCOC(=O)C[C@H](NC(=O)Nc1c(O)ccn(C)c1=O)c1cccc(Oc2ccccc2Cl)c1]

ethyl (S)-3-(3-(2,4-difluorophenoxy)phenyl)-3-(3-(4-hydroxy-1-methyl-2-oxo-1,2-dihydropyridin-3-yl)ureido)propanoate 3-31

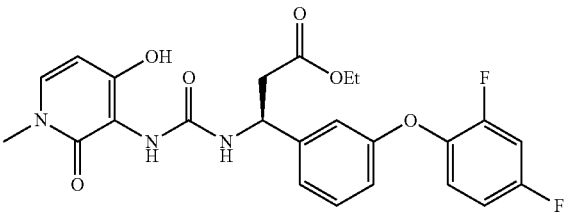 [SMILES: CCOC(=O)C[C@H](NC(=O)Nc1c(O)ccn(C)c1=O)c1cccc(Oc2ccc(F)cc2F)c1]

| | |
|---|---|
| ethyl (S)-3-(3-(2,6-dimethylphenoxy)phenyl)-3-(3-(4-hydroxy-1-methyl-2-oxo-1,2-dihydropyridin-3-yl)ureido)propanoate 3-32 | 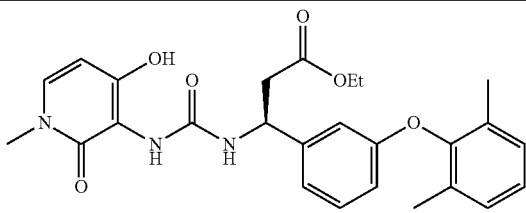 |

Step Two: In analogy to Example 1, Step Two, to a solution of 3-1 in THF at room temperature was added sodium hydroxide (2 N) and methanol. The mixture was stirred for 2 hours, and the organic solvents were removed on the rotary evaporator. The remaining aqueous solution was diluted with water, and extracted with ether. The aqueous layer was acidified with HCl (2 N) and extracted with ethyl acetate. The ethyl acetate layer was washed with brine, dried, filtered, and concentrated to give (S)-3-(3-(difluoro(o-tolyl)methyl)phenyl)-3-(3-(4-hydroxy-1-methyl-2-oxo-1,2-dihydropyridin-3-yl)ureido)propanoic acid 3-33. Likewise, this procedure was also used to prepare the other 3-aminopropanoic acids listed below. Compound 3-33 can also be prepared by this procedure without the aid of methanol as a co-solvent.

This procedure was also carried out using acetonitrile in place of THF, without the aid of methanol as a co-solvent, by stirring overnight. This modification was used to prepare compounds 3-36 and 3-37.

Likewise, in analogy with this procedure, the hydrolysis reaction of other ethyl 3-aminopropanoate analogs to free carboxylic acids was also used for the preparation of the following compounds.

| | |
|---|---|
| (S)-3-(3-(difluoro(o-tolyl)methyl)phenyl)-3-(3-(4-hydroxy-1-methyl-2-oxo-1,2-dihydropyridin-3-yl)ureido)propanoic acid 3-33 | 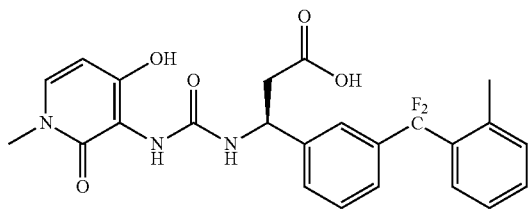 [SMILES: Cc1ccccc1C(F)(F)c1cccc([C@H](CC(=O)O)NC(=O)Nc2c(O)ccn(C)c2=O)c1] |
| (R)-3-(3-(difluoro(o-tolyl)methyl)phenyl)-3-(3-(4-hydroxy-1-methyl-2-oxo-1,2-dihydropyridin-3-yl)ureido)propanoic acid 3-34 | 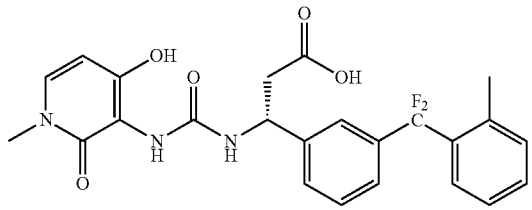 [SMILES: Cc1ccccc1C(F)(F)c1cccc([C@@H](CC(=O)O)NC(=O)Nc2c(O)ccn(C)c2=O)c1] |
| (S)-3-(3-(4-hydroxy-1-methyl-2-oxo-1,2-dihydropyridin-3-yl)ureido)-3-(3-phenoxyphenyl)propanoic acid 3-35 | 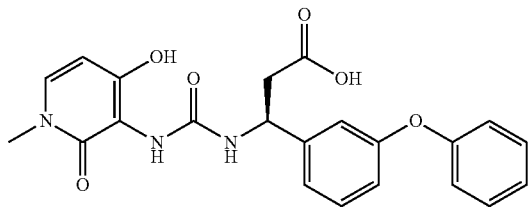 [SMILES: Cn1ccc(O)c(NC(=O)N[C@@H](CC(=O)O)c2cccc(Oc3ccccc3)c2)c1=O] |
| (S)-3-(3-(4-hydroxy-1-methyl-2-oxo-1,2-dihydropyridin-3-yl)ureido)-3-(4-(2-methoxyphenoxy)phenyl)propanoic acid 3-36 | 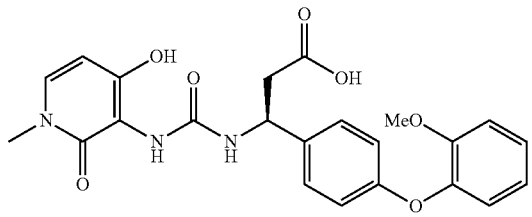 [SMILES: COc1ccccc1Oc1ccc([C@H](CC(=O)O)NC(=O)Nc2c(O)ccn(C)c2=O)cc1] |

-continued (S)-3-(3-(4-hydroxy-1-methyl-2-oxo-1,2-dihydropyridin-3-yl)ureido)-3-(4-(3-methoxyphenoxy)phenyl)propanoic acid 3-37

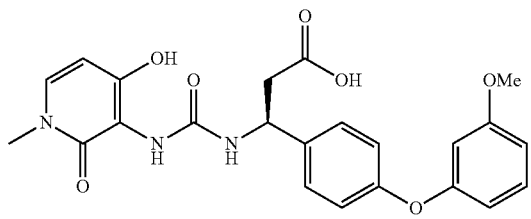 [SMILES: COc1cccc(Oc2ccc([C@H](CC(=O)O)NC(=O)Nc3c(O)ccn(C)c3=O)cc2)c1]

(S)-3-(3-(4-hydroxy-1-methyl-2-oxo-1,2-dihydropyridin-3-yl)ureido)-3-(4-(o-tolyloxy)phenyl)propanoic acid 3-38

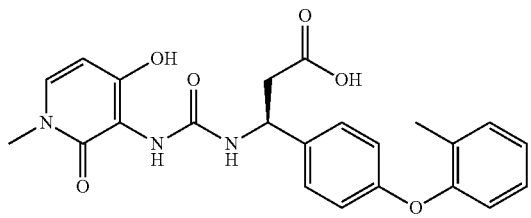

(S)-3-(3-(4-hydroxy-1-methyl-2-oxo-1,2-dihydropyridin-3-yl)ureido)-3-(4-(p-tolyloxy)phenyl)propanoic acid 3-39

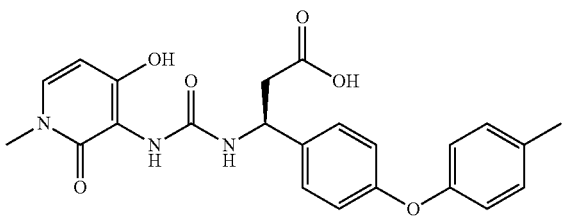

(S)-3-(4-benzylphenyl)-3-(3-(4-hydroxy-1-methyl-2-oxo-1,2-dihydropyridin-3-yl)ureido)propanoic acid 3-40

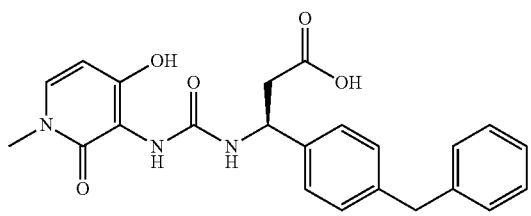 [SMILES: Cn1ccc(O)c(NC(=O)N[C@@H](CC(=O)O)c2ccc(Cc3ccccc3)cc2)c1=O]

(S)-3-(3-(4-hydroxy-1-methyl-2-oxo-1,2-dihydropyridin-3-yl)ureido)-3-(4-(2-methylbenzyl)phenyl)propanoic acid 3-41

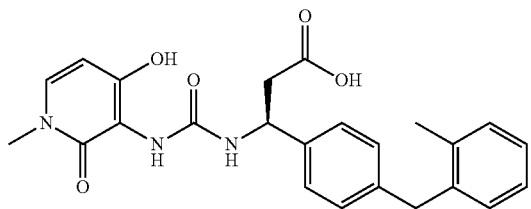

(S)-3-(3-(4-hydroxy-1-methyl-2-oxo-1,2-dihydropyridin-3-yl)ureido)-3-(4-(3-methylbenzyl)phenyl)propanoic acid 3-42

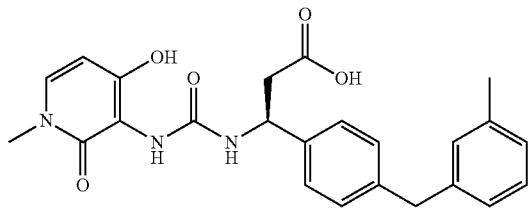 [SMILES: Cc1cccc(Cc2ccc([C@H](CC(=O)O)NC(=O)Nc3c(O)ccn(C)c3=O)cc2)c1]

(S)-3-(3-(4-hydroxy-1-methyl-2-oxo-1,2-dihydropyridin-3-yl)ureido)-3-(4-(4-methylbenzyl)phenyl)propanoic acid 3-43

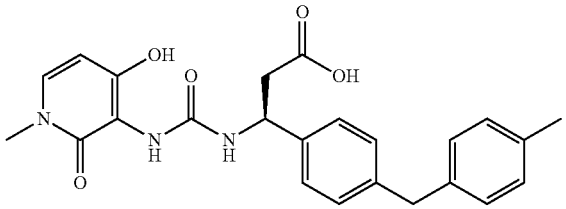

| | |
|---|---|
| (S)-3-(3-(2-ethylbenzyl)phenyl)-3-(3-(4-hydroxy-1-methyl-2-oxo-1,2-dihydropyridin-3-yl)ureido)propanoic acid 3-44 | 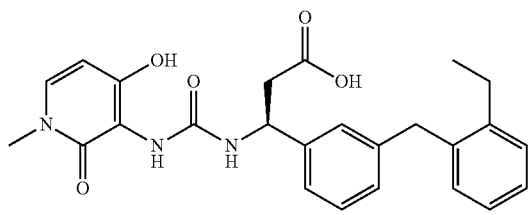 [SMILES: CCc1ccccc1Cc1cccc([C@H](CC(=O)O)NC(=O)Nc2c(O)ccn(C)c2=O)c1] |
| (S)-3-(3-(2-methylbenzyl)phenyl)-3-(3-(4-hydroxy-1-methyl-2-oxo-1,2-dihydropyridin-3-yl)ureido)propanoic acid 3-45 | 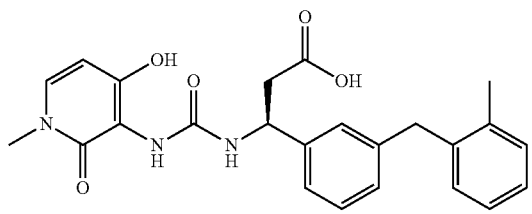 [SMILES: Cc1ccccc1Cc1cccc([C@H](CC(=O)O)NC(=O)Nc2c(O)ccn(C)c2=O)c1] |
| (S)-3-(3-(3-methylbenzyl)phenyl)-3-(3-(4-hydroxy-1-methyl-2-oxo-1,2-dihydropyridin-3-yl)ureido)propanoic acid 3-46 | 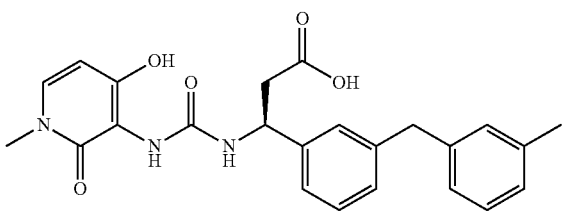 |
| S)-3-(3-(4-methylbenzyl)phenyl)-3-(3-(4-hydroxy-1-methyl-2-oxo-1,2-dihydropyridin-3-yl)ureido)propanoic acid 3-47 | 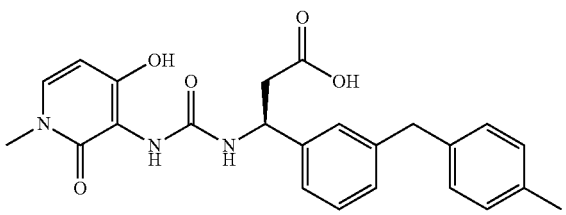 |
| (S)-3-(3-(4-hydroxy-1-methyl-2-oxo-1,2-dihydropyridin-3-yl)ureido)-3-(3-(o-tolyloxy)phenyl)propanoic acid 3-48 | 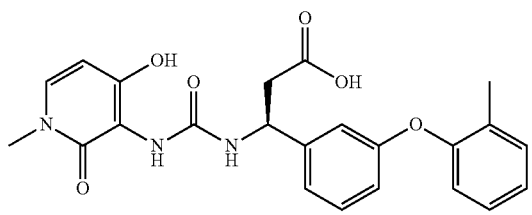 |
| (S)-3-(3-(4-hydroxy-1-methyl-2-oxo-1,2-dihydropyridin-3-yl)ureido)-3-(3-(2-methoxyphenoxy)phenyl)propanoic acid 3-49 | 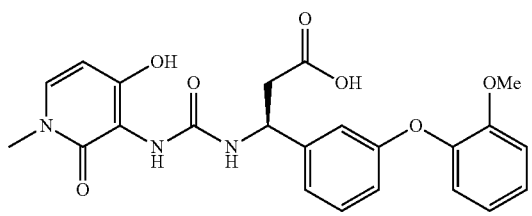 [SMILES: COc1ccccc1Oc1cccc([C@H](CC(=O)O)NC(=O)Nc2c(O)ccn(C)c2=O)c1] |
| (S)-3-(3-(2-chlorophenoxy)phenyl)-3-(3-(4-hydroxy-1-methyl-2-oxo-1,2-dihydropyridin-3-yl)ureido)propanoic acid 3-50 | 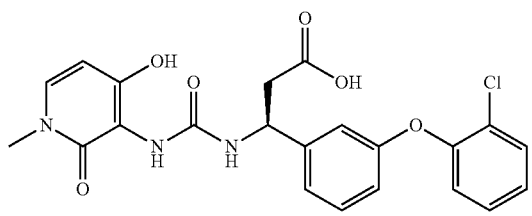 [SMILES: Cn1ccc(O)c(NC(=O)N[C@@H](CC(=O)O)c2cccc(Oc3ccccc3Cl)c2)c1=O] |

(S)-3-(3-(4-hydroxy-1-methyl-2-oxo-1,2-dihydropyridin-3-yl)ureido)-3-(3-(m-tolyloxy)phenyl)propanoic acid 3-51

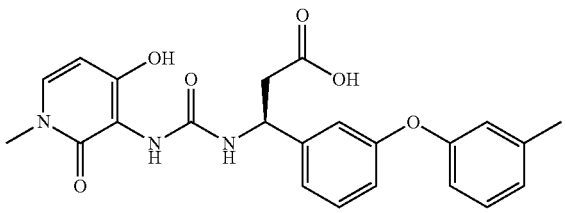

(S)-3-(3-(4-hydroxy-1-methyl-2-oxo-1,2-dihydropyridin-3-yl)ureido)-3-(3-(p-tolyloxy)phenyl)propanoic acid 3-52

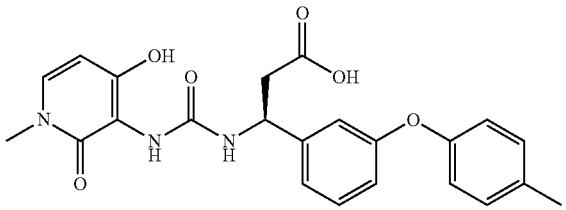

(S)-3-(3-(2,4-difluorophenoxy)phenyl)-3-(3-(4-hydroxy-1-methyl-2-oxo-1,2-dihydropyridin-3-yl)ureido)propanoic acid 3-53

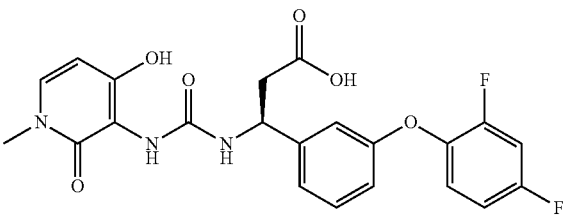 [SMILES: Cn1ccc(O)c(NC(=O)N[C@@H](CC(=O)O)c2cccc(Oc3ccc(F)cc3F)c2)c1=O]

(S)-3-(3-(2,6-dimethylphenoxy)phenyl)-3-(3-(4-hydroxy-1-methyl-2-oxo-1,2-dihydropyridin-3-yl)ureido)propanoic acid 3-54

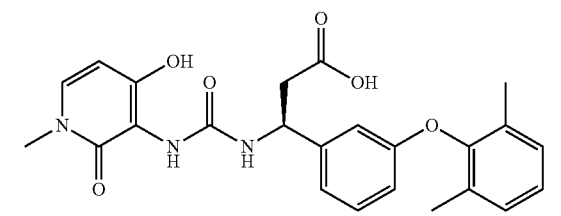

(S)-3-(3-(4-hydroxy-1-methyl-2-oxo-1,2-dihydropyridin-3-yl)ureido)-3-(3-(2-trifluoromethylbenzyl)phenyl)propanoic acid 3-55

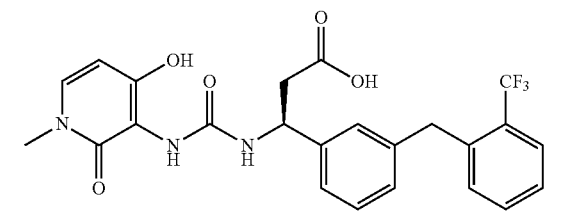 [SMILES: Cn1ccc(O)c(NC(=O)N[C@@H](CC(=O)O)c2cccc(Cc3ccccc3C(F)(F)F)c2)c1=O]

(S)-3-(3-(4-hydroxy-1-methyl-2-oxo-1,2-dihydropyridin-3-yl)ureido)-3-(3-(3-trifluoromethylbenzyl)phenyl)propanoic acid 3-56

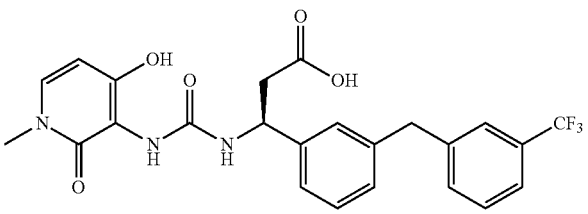 [SMILES: Cn1ccc(O)c(NC(=O)N[C@@H](CC(=O)O)c2cccc(Cc3cccc(C(F)(F)F)c3)c2)c1=O]

(S)-3-(3-(4-hydroxy-1-methyl-2-oxo-1,2-dihydropyridin-3-yl)ureido)-3-(3-(4-(trifluoromethyl)benzyl)phenyl)propanoic acid 3-57

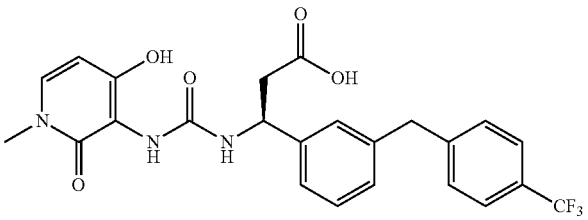

| | |
|---|---|
| (S)-3-(3-(2-(difluoromethoxy)benzyl)phenyl)-3-(3-(4-hydroxy-1-methyl-2-oxo-1,2-dihydropyridin-3-yl)ureido)propanoic acid 3-58 | 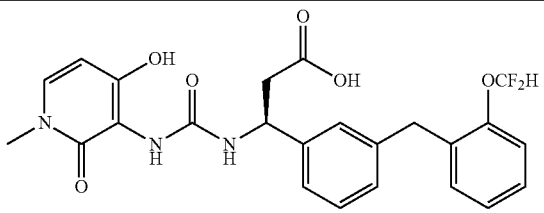 |
| (S)-3-(3-(4-hydroxy-1-methyl-2-oxo-1,2-dihydropyridin-3-yl)ureido)-3-(3-(2-methoxybenzyl)phenyl)propanoic acid 3-59 | 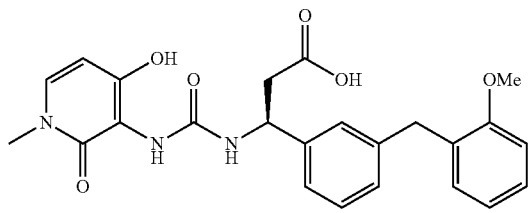 [SMILES: COc1ccccc1Cc1cccc([C@H](CC(=O)O)NC(=O)Nc2c(O)ccn(C)c2=O)c1] |
| (S)-3-(3-(2-fluorobenzyl)phenyl)-3-(3-(4-hydroxy-1-methyl-2-oxo-1,2-dihydropyridin-3-yl)ureido)propanoic acid 3-60 | 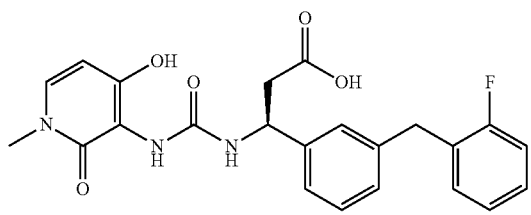 [SMILES: Cn1ccc(O)c(NC(=O)N[C@@H](CC(=O)O)c2cccc(Cc3ccccc3F)c2)c1=O] |
| (S)-3-(3-(2,6-dimethylbenzyl)phenyl)-3-(3-(4-hydroxy-1-methyl-2-oxo-1,2-dihydropyridin-3-yl)ureido)propanoic acid 3-61 | 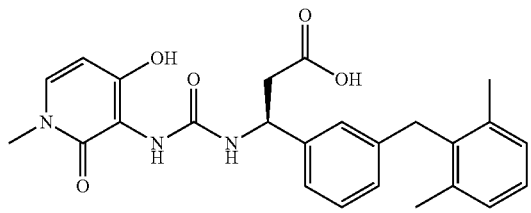 [SMILES: Cc1cccc(C)c1Cc1cccc([C@H](CC(=O)O)NC(=O)Nc2c(O)ccn(C)c2=O)c1] |
| (S)-3-(3-(5-fluoro-2-methylbenzyl)phenyl)-3-(3-(4-hydroxy-1-methyl-2-oxo-1,2-dihydropyridin-3-yl)ureido)propanoic acid 3-62 | 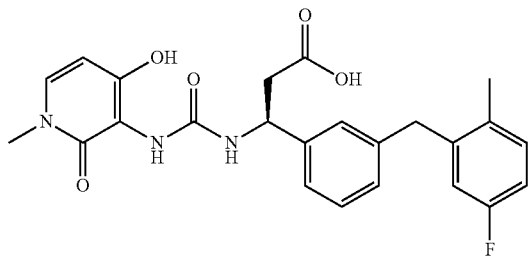 [SMILES: Cc1ccc(F)cc1Cc1cccc([C@H](CC(=O)O)NC(=O)Nc2c(O)ccn(C)c2=O)c1] |
| (S)-3-(3-(4-hydroxy-1-methyl-2-oxo-1,2-dihydropyridin-3-yl)ureido)-3-(5-(2-methylbenzyl)thiophen-2-yl)propanoic acid 3-63 | 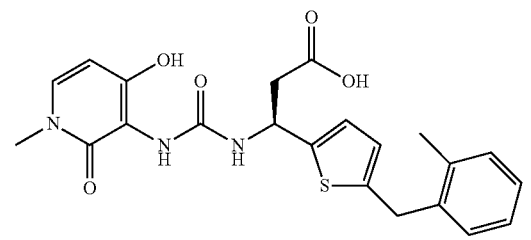 |
| (S)-3-(5-benzylthiophen-2-yl)-3-(3-(4-hydroxy-1-methyl-2-oxo-1,2-dihydropyridin-3-yl)ureido)propanoic acid 3-64 | 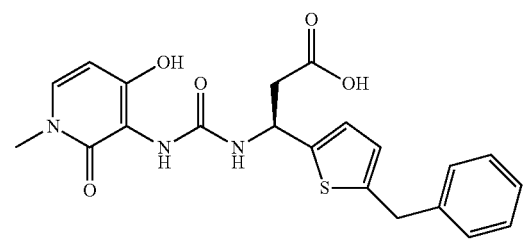 [SMILES: Cn1ccc(O)c(NC(=O)N[C@@H](CC(=O)O)c2ccc(Cc3ccccc3)s2)c1=O] |

Step Three: In analogy to Example 1, Step Three, to a solution of 3-33 in inhibitor free THF, aqueous sodium hydroxide (0.1000 N) was added. The mixture was heated briefly to 40° C. to give a homogeneous mixture, and the THF was removed by rotary evaporation. The mixture was diluted with deionized water, then frozen in a dry ice/acetone bath and lyophilized to give sodium sodium (S)-3-(3-(difluoro(o-tolyl)methyl) phenyl)-3-(3-(1-methyl-4-oxido-2-oxo-1,2-dihydropyridin-3-yl)ureido)propanoate 3-65.

This procedure could also be done using acetonitrile instead of THF. This modification was used to prepare sodium (S)-3-(3-(1-methyl-4-oxido-2-oxo-1,2-dihydropyridin-3-yl)ureido)-3-(3-phenoxyphenyl)propanoate 3-71.

Likewise, this procedure was also used to prepare the other 3-aminopropanoic acids listed below.

sodium (S)-3-(3-(difluoro(o-tolyl)methyl) phenyl)-3-(3-(1-methyl-4-oxido-2-oxo-1,2-dihydropyridin-3-yl)ureido)propanoate 3-65
MS [M + H$^+$]$^+$: 472.12; a4b1 IC$_{50}$ = <20 nM: a4b7 IC$_{50}$ = <200 nM

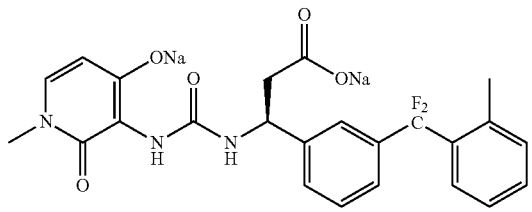

sodium (R)-3-(3-(difluoro(o-tolyl)methyl) phenyl)-3-(3-(1-methyl-4-oxido-2-oxo-1,2-dihydropyridin-3-yl)ureido)propanoate 3-66
MS [M + H$^+$]$^+$: 469.96; a4b1 IC$_{50}$ = >200 nM: a4b7 IC$_{50}$ = nd

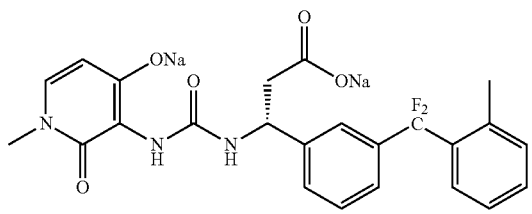

sodium (S)-3-(3-(1-methyl-4-oxido-2-oxo-1,2-dihydropyridin-3-yl)ureido)-3-(3-(o-tolyloxy)phenyl)propanoate 3-67
MS [M + H$^+$]$^+$: 437.97; a4b1 IC$_{50}$ = <20 nM: a4b7 IC$_{50}$ = nd

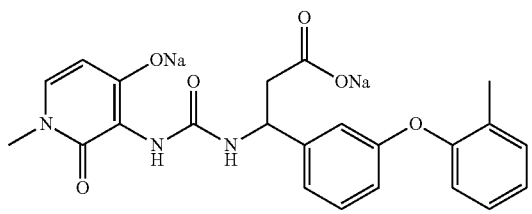

sodium (S)-3-(3-(2-methoxyphenoxy) phenyl)-3-(3-(1-methyl-4-oxido-2-oxo-1,2-dihydropyridin-3-yl)ureido)propanoate 3-68
MS [M + H$^+$]$^+$: 454.01; a4b1 IC$_{50}$ = <20 nM: a4b7 IC$_{50}$ = nd

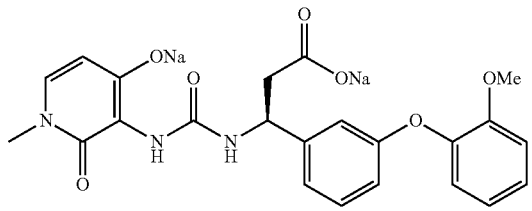

sodium (S)-3-(3-(2-chlorophenoxy) phenyl)-3-(3-(1-methyl-4-oxido-2-oxo-1,2-dihydropyridin-3-yl)ureido)propanoate 3-69,
MS [M + H$^+$]$^+$: 457.98; a4b1 IC$_{50}$ = <20 nM: a4b7 IC$_{50}$ = nd

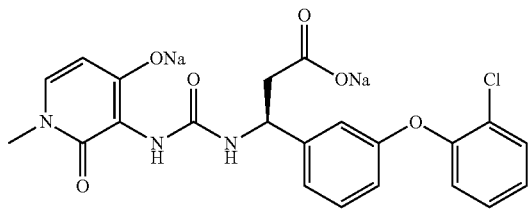

sodium (S)-3-(3-(5-fluoro-2-methylbenzyl) phenyl)-3-(3-(1-methyl-4-oxido-2-oxo-1,2-dihydropyridin-3-yl)ureido)propanoate 3-70
MS [M + H$^+$]$^+$: 454.03; a4b1 IC$_{50}$ = <20 nM: a4b7 IC$_{50}$ = nd

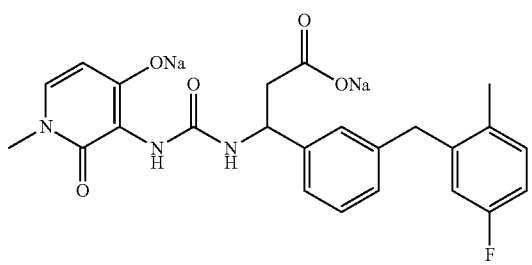

sodium (S)-3-(3-(1-methyl-4-oxido-2-oxo-1,2-dihydropyridin-3-yl)ureido)-3-(3-phenoxyphenyl)propanoate 3-71
MS [M + H$^+$]$^+$: 423.99; a4b1 IC$_{50}$ = <200: a4b7 IC$_{50}$ = <20 nM

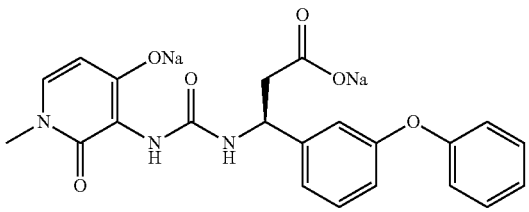

sodium (S)-3-(4-(2-methoxyphenoxy)phenyl)-3-(3-(1-methyl-4-oxido-2-oxo-1,2-dihydropyridin-3-yl)ureido)propanoate 3-72
MS [M + H$^+$]$^+$: 453.98; a4b1 IC$_{50}$ = <200 nM: a4b7 IC$_{50}$ = nd

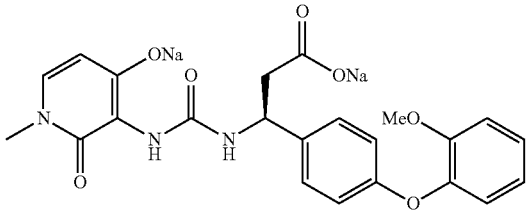

sodium (S)-3-(4-(3-methoxyphenoxy)phenyl)-3-(3-(1-methyl-4-oxido-2-oxo-1,2-dihydropyridin-3-yl)ureido)propanoate 3-73
MS [M + H$^+$]$^+$: 453.96; a4b1 IC$_{50}$ = <200 nM: a4b7 IC$_{50}$ = nd

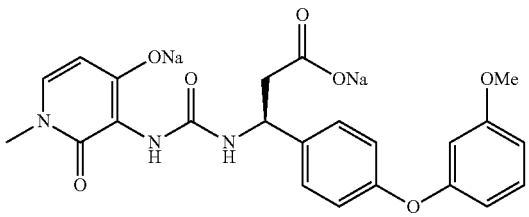

sodium (S)-3-(3-(1-methyl-4-oxido-2-oxo-1,2-dihydropyridin-3-yl)ureido)-3-(4-(o-tolyloxy)phenyl)propanoate 3-74
MS [M + H$^+$]$^+$: 438.34; a4b1 IC$_{50}$ = <20 nM: a4b7 IC$_{50}$ = nd

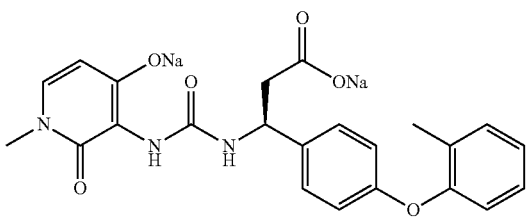

sodium (S)-3-(3-(1-methyl-4-oxido-2-oxo-1,2-dihydropyridin-3-yl)ureido)-3-(4-(p-tolyloxy)phenyl)propanoate 3-75
MS [M + H$^+$]$^+$: 437.97; a4b1 IC$_{50}$ = <200 nM: a4b7 IC$_{50}$ = nd

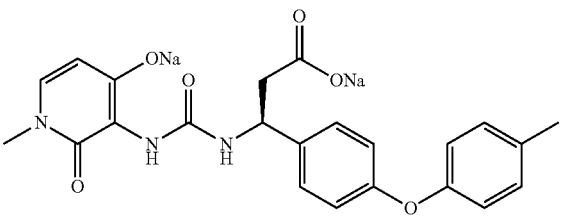

sodium (S)-3-(4-benzylphenyl)-3-(3-(1-methyl-4-oxido-2-oxo-1,2-dihydropyridin-3-yl)ureido)propanoate 3-76
MS [M + H$^+$]$^+$: 422.04; a4b1 IC$_{50}$ = <20 nM: a4b7 IC$_{50}$ = nd

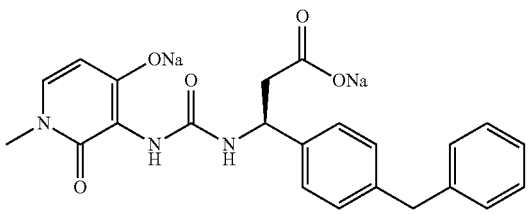

sodium (S)-3-(3-(1-methyl-4-oxido-2-oxo-1,2-dihydropyridin-3-yl)ureido)-3-(4-(2-methylbenzyl)phenyl)propanoate 3-77
MS [M + H$^+$]$^+$: 436.00; a4b1 IC$_{50}$ = <200 nM: a4b7 IC$_{50}$ = nd

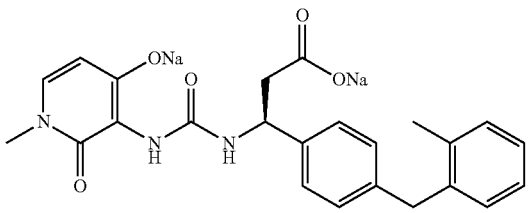

sodium (S)-3-(3-(1-methyl-4-oxido-2-oxo-
1,2-dihydropyridin-3-yl)ureido)-3-(4-(3-
methylbenzyl)phenyl)propanoate 3-78
MS [M + H$^+$]$^+$: 436.04; a4b1 IC$_{50}$ =
>200 nM: a4b7 IC$_{50}$ = nd

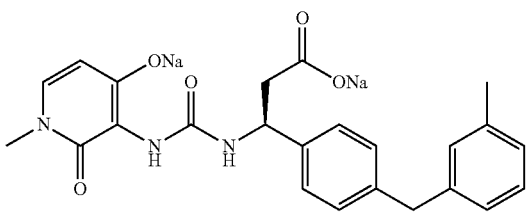

sodium (S)-3-(3-(1-methyl-4-oxido-2-oxo-
1,2-dihydropyridin-3-yl)ureido)-3-(4-(4-
methylbenzyl)phenyl)propanoate 3-79
MS [M + H$^+$]$^+$: 436.02; a4b1 IC$_{50}$ =
>200 nM: a4b7 IC$_{50}$ = nd

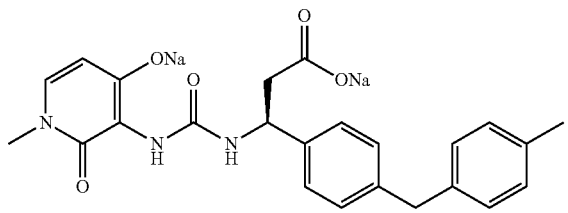

sodium (S)-3-(3-(2-ethylbenzyl)phenyl)-3-
(3-(1-methyl-4-oxido-2-oxo-1,2-dihydro-
pyridin-3-yl)ureido)propanoate 3-80
MS [M + H$^+$]$^+$: 450.05; a4b1 IC$_{50}$ =
<20 nM: a4b7 IC$_{50}$ = nd

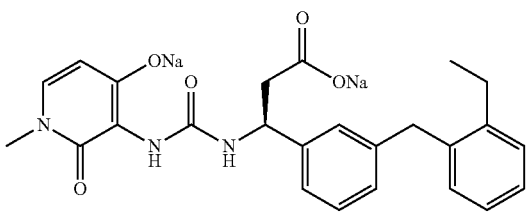

sodium (S)-3-(3-(1-methyl-4-oxido-2-oxo-
1,2-dihydropyridin-3-yl)ureido)-3-(3-(2-
methylbenzyl)phenyl)propanoate 3-81
MS [M + H$^+$]$^+$: 436.05; a4b1 IC$_{50}$ =
<20 nM: a4b7 IC$_{50}$ = nd

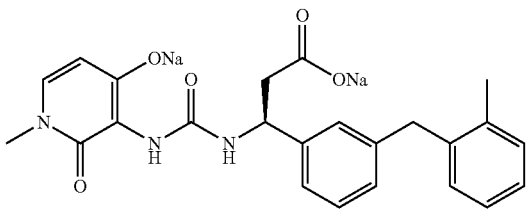

sodium (S)-3-(3-(1-methyl-4-oxido-2-oxo-
1,2-dihydropyridin-3-yl)ureido)-3-(3-(4-
methylbenzyl)phenyl)propanoate 3-82
MS [M + H$^+$]$^+$: 436.05; a4b1 IC$_{50}$ =
<20 nM: a4b7 IC$_{50}$ = nd

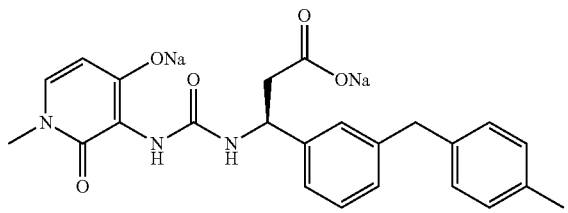

sodium (S)-3-(3-(1-methyl-4-oxido-2-oxo-
1,2-dihydropyridin-3-yl)ureido)-3-(3-(3-
methylbenzyl)phenyl)propanoate 3-83
MS [M + H$^+$]$^+$: 436.05; a4b1 IC$_{50}$ =
<200 nM: a4b7 IC$_{50}$ = nd

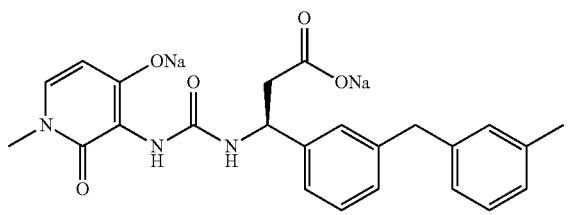

sodium (S)-3-(3-(1-methyl-4-oxido-2-oxo-
1,2-dihydropyridin-3-yl)ureido)-3-(3-(m-
tolyloxy)phenyl)propanoate 3-84
MS [M + H$^+$]$^+$: 438.22; a4b1 IC$_{50}$ =
<20 nM: a4b7 IC$_{50}$ = nd

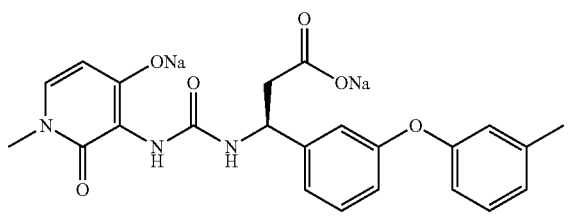

sodium (S)-3-(3-(1-methyl-4-oxido-2-oxo-1,2-dihydropyridin-3-yl)ureido)-3-(3-(p-tolyloxy)phenyl)propanoate 3-85
MS [M + H+]+: 438.28; a4b1 IC$_{50}$ = <20 nM: a4b7 IC$_{50}$ = nd

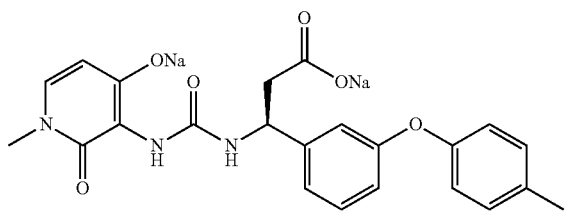

sodium(S)-3-(3-(2,4-difluorophenoxy)phenyl)-3-(3-(1-methyl-4-oxido-2-oxo-1,2-dihydropyridin-3-yl)ureido)propanoate 3-86
MS [M + H+]+: 460.10; a4b1 IC$_{50}$ = <20 nM: a4b7 IC$_{50}$ = nd

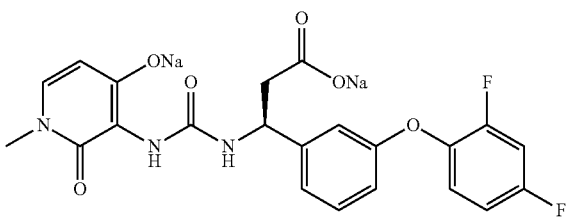

sodium(S)-3-(3-(2,6-dimethylphenoxy)phenyl)-3-(3-(1-methyl-4-oxido-2-oxo-1,2-dihydropyridin-3-yl)ureido)propanoate 3-87
MS [M + H+]+: 452.32; a4b1 IC$_{50}$ = <20 nM: a4b7 IC$_{50}$ = nd

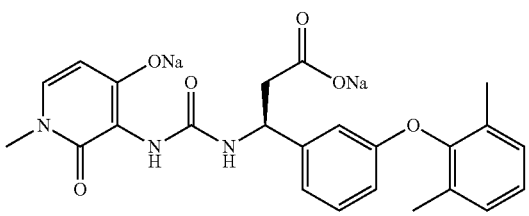

sodium (S)-3-(3-(1-methyl-4-oxido-2-oxo-1,2-dihydropyridin-3-yl)ureido)-3-(3-(2-(trifluoromethyl)benzyl)phenyl)propanoate 3-88
MS [M + H+]+: 490.05; a4b1 IC$_{50}$ = <20 nM: a4b7 IC$_{50}$ = nd

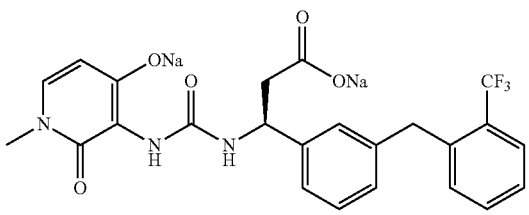

sodium (S)-3-(3-(1-methyl-4-oxido-2-oxo-1,2-dihydropyridin-3-yl)ureido)-3-(3-(3-(trifluoromethyl)benzyl)phenyl)propanoate 3-89
MS [M + H+]+: 490.06; a4b1 IC$_{50}$ = <20 nM: a4b7 IC$_{50}$ = nd

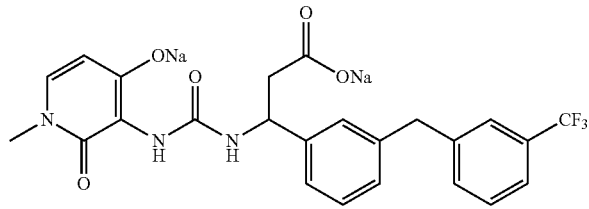

sodium (S)-3-(3-(1-methyl-4-oxido-2-oxo-1,2-dihydropyridin-3-yl)ureido)-3-(3-(4-(trifluoromethyl)benzyl)phenyl)propanoate 3-90
MS [M + H+]+: 490.04; a4b1 IC$_{50}$ = <20 nM: a4b7 IC$_{50}$ = nd

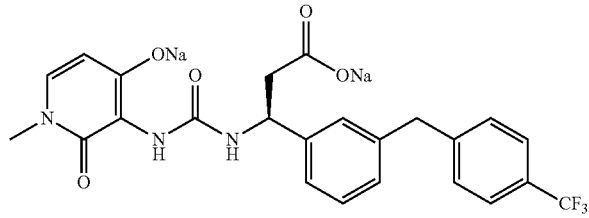

sodium(S)-3-(3-(2-(difluoromethoxy)benzyl)phenyl)-3-(3-(1-methyl-4-oxido-2-oxo-1,2-dihydropyridin-3-yl)ureido)propanoate 3-91
MS [M + H+]+: 488.02; a4b1 IC$_{50}$ = <20 nM: a4b7 IC$_{50}$ = nd

| | |
|---|---|
| sodium(S)-3-(3-(2-(methoxybenzyl)phenyl)-3-(3-(1-methyl-4-oxido-2-oxo-1,2-dihydropyridin-3-yl)ureido)propanoate 3-92<br>MS [M + H⁺]⁺: 452.04; a4b1 IC$_{50}$ = <20 nM; a4b7 IC$_{50}$ = nd | 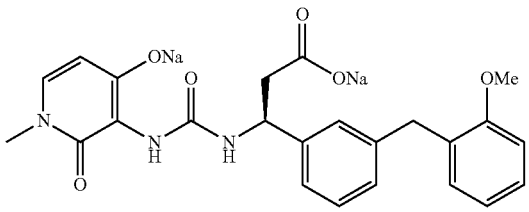 |
| sodium (S)-3-(3-(2-fluorobenzyl)phenyl)-3-(3-(1-methyl-4-oxido-2-oxo-1,2-dihydropyridin-3-yl)ureido)propanoate 3-93<br>MS [M + H⁺]⁺: 440.02; a4b1 IC$_{50}$ = <20 nM; a4b7 IC$_{50}$ = nd | 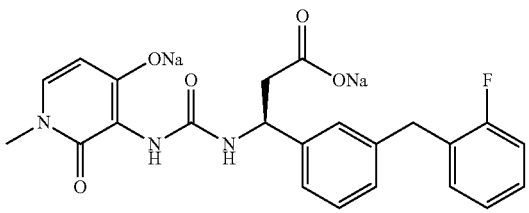 |
| sodium (S)-3-(3-(2,6-dimethylbenzyl)phenyl)-3-(3-(1-methyl-4-oxido-2-oxo-1,2-dihydropyridin-3-yl)ureido)propanoate 3-94<br>MS [M + H⁺]⁺: 450.07; a4b1 IC$_{50}$ = <20 nM; a4b7 IC$_{50}$ = nd | 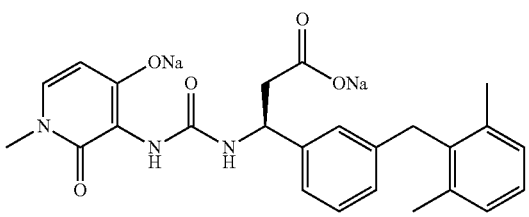 |
| sodium (S)-3-(3-(1-methyl-4-oxido-2-oxo-1,2-dihydropyridin-3-yl)ureido)-3-(5-(2-methylbenzyl)thiophen-2-yl)propanoate 3-95<br>MS [M + H⁺]⁺: 441.98; a4b1 IC$_{50}$ = <20 nM; a4b7 IC$_{50}$ = nd | 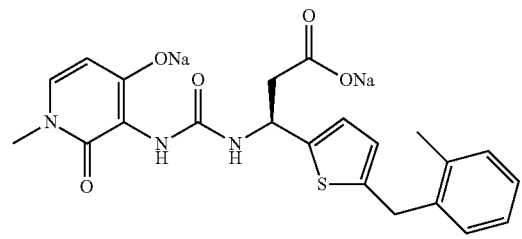 |
| sodium (S)-3-(5-benzylthiophen-2-yl)-3-(3-(1-methyl-4-oxido-2-oxo-1,2-dihydropyridin-3-yl)ureido)propanoate 3-96<br>MS [M + H⁺]⁺: 427.94; a4b1 IC$_{50}$ = <20 nM; a4b7 IC$_{50}$ = nd | 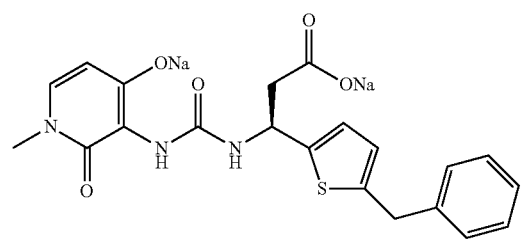 |

Example 4

Synthesis of 5,7-dimethyloxazolo[4,5-c]pyridine-2,4(3H,5H)-dione (4-5)

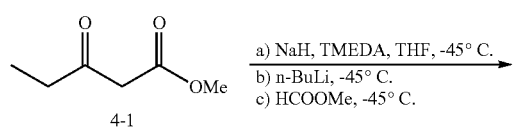

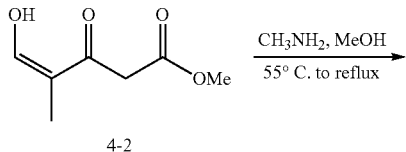

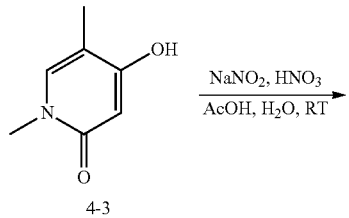

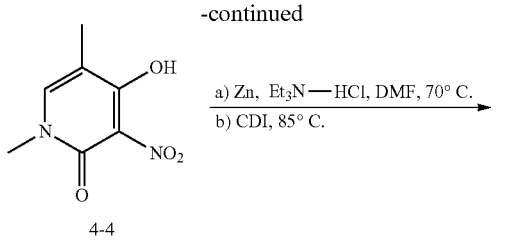

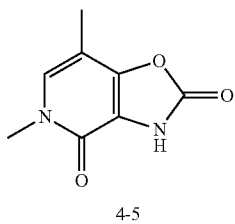

Step One: To a suspension of sodium hydride (6.4 g of 60% dispersion in mineral oil, 160 mmol) in THF (400 mL) under a dry nitrogen atmosphere, TMEDA (23.4 mL, 155 mmol) and methyl propionylacetate (4-1, 18.1 mL, 144 mmol) were added and the mixture was cooled to −45° C. A solution of n-butyllithium (90 mL, 1.6M in hexanes, 274 mmol) was added dropwise and the resulting mixture was stirred at −45° C. for 1 hour. Methyl formate (6.0 mL, 97 mmol) was then added rapidly and the mixture was allowed to stir for 30 minutes before quenching with HCl (6 N, 250 mL). The reaction was diluted with diethyl ether (150 mL) and the organic layer was washed twice more with water. The aqueous layers were combined and sodium chloride was added until saturated. This mixture was extracted with ethyl acetate (3 times). The original ether layer was washed with saturated sodium bicarbonate solution and water. The combined aqueous washes were acidified with excess HCl (2 N), saturated with sodium chloride and extracted with ethyl acetate (3 times). All of the ethyl acetate extracts were combined and dried over MgSO$_4$. The resulting mixture was vacuum filtered through coarse silica gel and the filtrate was concentrated under reduced pressure to give methyl 5-hydroxy-4-methyl-3-oxopent-4-enoate (4-2, 13.49 g, %) as a light yellow oil. This material was used without further purification.

Step Two: To a solution of 4-2 (13.49 g, 85.3 mmol) in anhydrous methanol (250 mL) at room temperature, a solution of methylamine anhydrous methanol (2.0 M, 46.9 mL, 93.8 mmol) was added slowly. The solution was heated at 55° C. two hours then refluxed overnight. The reaction mixture was cooled to room temperature and concentrated to dryness. The residue was brought up in dichloromethane and filtered. The solid was collected and dried under vacuum to give 4-hydroxy-1,5-dimethylpyridin-2(1H)-one (4-3, 4.056 g) as a light yellow solid. The filtrate was concentrated, taken up in acetone and filtered to yield and additional portion (1.636 g).

Step Three: To a suspension of 4-3 (1.636 g, 11.8 mmol) in glacial acetic acid (40 mL) at room temperature, NaNO$_2$ (41 mg, 0.59 mmol), water (3.36 mL) and HNO$_3$ (70%, 2.27 mL, 35.3 mmol) were added sequentially. The resulting bright yellow solution was stirred at room temperature overnight, was diluted with water, and extracted with ethyl acetate three times. The organic layers were combined and washed with brine, dried over MgSO$_4$ and filtered. This reaction was repeated on the remainder of the material from the previous step (4.047 g 4-3, 97 mL acetic acid, 100 mg NaNO$_2$, 8.3 mL water and 5.6 mL nitric acid). The filtrates from the two reactions were combined and concentrated under reduced pressure to give 4-hydroxy-1,5-dimethyl-3-nitropyridin-2(1H)-one (4-4, 6.47 g) as an yellow-orange solid.

Step Four: To a solution of 4-4 (6.45 g, 35.0 mmol) in DMF (117 mL) at room temperature under a dry nitrogen atmosphere, Zn powder (10.3 g, 158 mmol) and triethylamine hydrochloride (26.5 g, 193 mmol) were added. The resulting mixture was heated to 70° C. for 1 hour, and was cooled to room temperature. To the resulting mixture, CDI (11.36 g, 70.1 mmol) was added as a solid. Upon addition, gas evolution occurred. The mixture was then heated to 85° C. for 2 hours, cooled to room temperature, and filtered through a Buchner funnel into HCl (2 N). The suspension was stirred for 15 minutes, and filtered. The solid was resuspended in HCl (1 N), stirred for 15 minutes, and was filtered again, washing with water. The solid was dried under vacuum to give 5,7-dimethyloxazolo[4,5-c]pyridine-2,4(3H,5H)-dione (4-5, 3.981 g) as an off-white solid.

Example 5

Synthesis of 5,6-dimethyloxazolo[4,5-c]pyridine-2,4 (3H,5H)-dione (5-3)

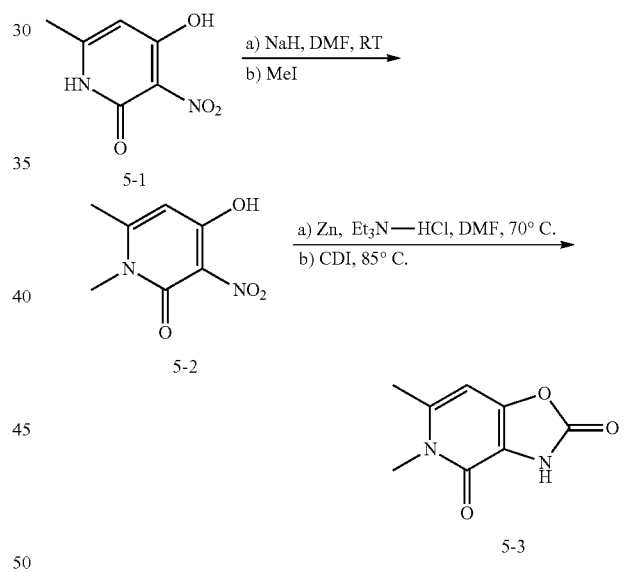

Step One: To a solution of 4-hydroxy-6-methyl-3-nitropyridone (998 mg, 5.87 mmol) in N,N-dimethylformamide at room temperature under argon, sodium hydride (60% dispersion in mineral oil, 517 mg, 12.9 mmol) was added in three portions. The resulting mixture was stirred for 1 hour and iodomethane (0.44 mL, 7.04 mmol) was added by syringe. The mixture was stirred overnight, during which time a solid had formed. The mixture was poured into 50% ethyl acetate in hexanes, rinsing the reaction flask with ethyl acetate. The resulting suspension was stirred for 30 minutes then filtered, washing with 50% ethyl acetate in hexanes. The solid cake was air dried for 15 minutes then was dissolved in water (40 mL) and acidified with aqueous hydrocholoric acid (2N, 10 mL). The resulting mixture was stirred for 30 minutes, during which time a yellow solid had formed. The mixture was filtered, washing with water, and the solid was dried under vacuum overnight to give 4-hydroxy-1,6-dimethyl-3-nitropyridin-2(1H)-one (5-2, 865 mg) as a yellow powder.

This procedure was also used to prepare 4-hydroxy-1-methyl-3-nitropyridin-2(1H)-one.

Step Two: To a solution of 5-2 (860 mg, 4.67 mmol) in N,N-dimethylformamide (15.6 mL) at room temperature under argon, zinc dust (1.374 g, 21.0 mmol) and trimethylamine hydrochloride (3.536 g, 25.7 mmol) were added. The mixture was heated to 60° C. for 3 hours then cooled to room temperature, and 1,1'-carbonyldiimidazole (2.27 g, 14.0 mmol) was added in one portion (gas evolution). The mixture was heated under argon to 80° C. for 2 hours then filtered hot to remove the unreacted zinc, washing with N,N-dimethylformamide. The filtrate was concentrated under reduced pressure and the residue was taken up in aqueous hydrochloric acid (1N, 50 mL). The flask was vigorously swirled for 5 minutes then the resulting suspension was filtered, washing with water. The solid was dried under vacuum to give 5,6-dimethyloxazolo[4,5-c]pyridine-2,4(3H,5H)-dione (5-3, 637 mg) as a cream colored powder.

This procedure was also used to prepare 5-methyloxazolo[4,5-c]pyridine-2,4(3H,5H)-dione.

Example 6

Synthesis of 5-methyloxazolo[4,5-c]pyridine-2,4(3H,5H)-dione. (6-3)

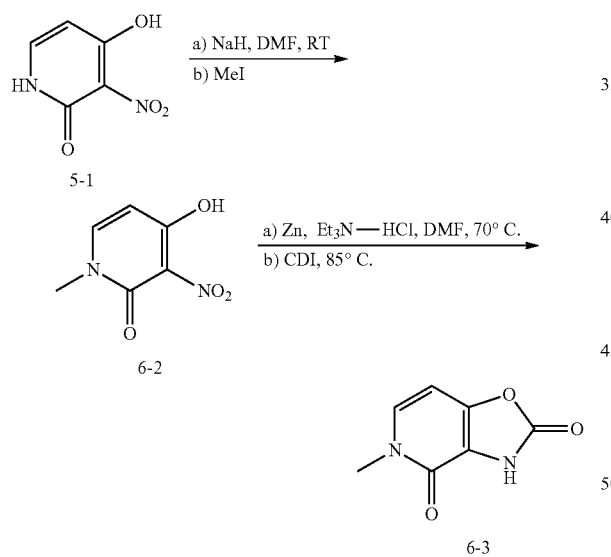

Step One: To a solution of 4-hydroxy-3-nitropyridone (1117 mg, 7.16 mmol) in N,N-dimethylformamide at room temperature under argon, sodium hydride (60% dispersion in mineral oil, 631 mg, 15.74 mmol) was added in three portions. The resulting mixture was stirred for 1 hour and iodomethane (0.54 mL 8.59 mmol) was added by syringe. The mixture was stirred overnight, during which time a solid had formed. The mixture was poured into 50% ethyl acetate in hexanes, rinsing the reaction flask with ethyl acetate. The resulting suspension was stirred for 30 minutes then filtered, washing with 50% ethyl acetate in hexanes. The solid cake was air dried for 15 minutes then was dissolved in water (55 mL) and acidified with aqueous hydrocholoric acid (2N, 13 mL). The resulting mixture was stirred for 30 minutes, during which time a yellow solid had formed. The mixture was filtered, washing with water, and the solid was dried under vacuum overnight to give 4-hydroxy-1-methyl-3-nitropyridin-2(1H)-one (6-2, 1036 mg) as a yellow powder.

Step Two: To a solution of 6-2 (995 mg, 5.99 mmol) in N,N-dimethylformamide (18.7 mL) at room temperature under argon, zinc dust (1.647 g, 25.2 mmol) and trimethylamine hydrochloride (4.239 g, 30.8 mmol) were added. The mixture was heated to 60° C. for 3 hours then cooled to room temperature, and 1,1'-carbonyldiimidazole (2.72 g, 16.8 mmol) was added in one portion (gas evolution). The mixture was heated under argon to 80° C. for 2 hours then filtered hot to remove the unreacted zinc, washing with N,N-dimethylformamide. The filtrate was concentrated under reduced pressure and the residue was taken up in aqueous hydrochloric acid (1N, 50 mL). The flask was vigorously swirled for 5 minutes then the resulting suspension was filtered, washing with water. The solid was dried under vacuum to give 5-methyloxazolo[4,5-c]pyridine-2,4(3H,5H)-dione (6-3, 752 mg) as a cream colored powder.

Example 7

Synthesis of (S)-ethyl 3-amino-3-(3-(difluoro(o-tolyl)methyl)phenyl)propanoate hydro chloride (7-6) and (R)-ethyl 3-amino-3-(3-(difluoro(o-tolyl)methyl)phenyl)propanoate hydrochloride (7-9)

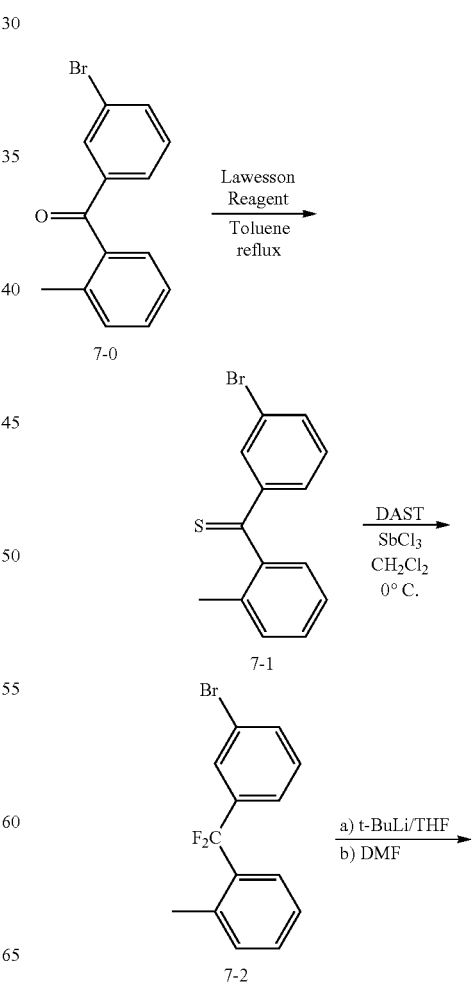

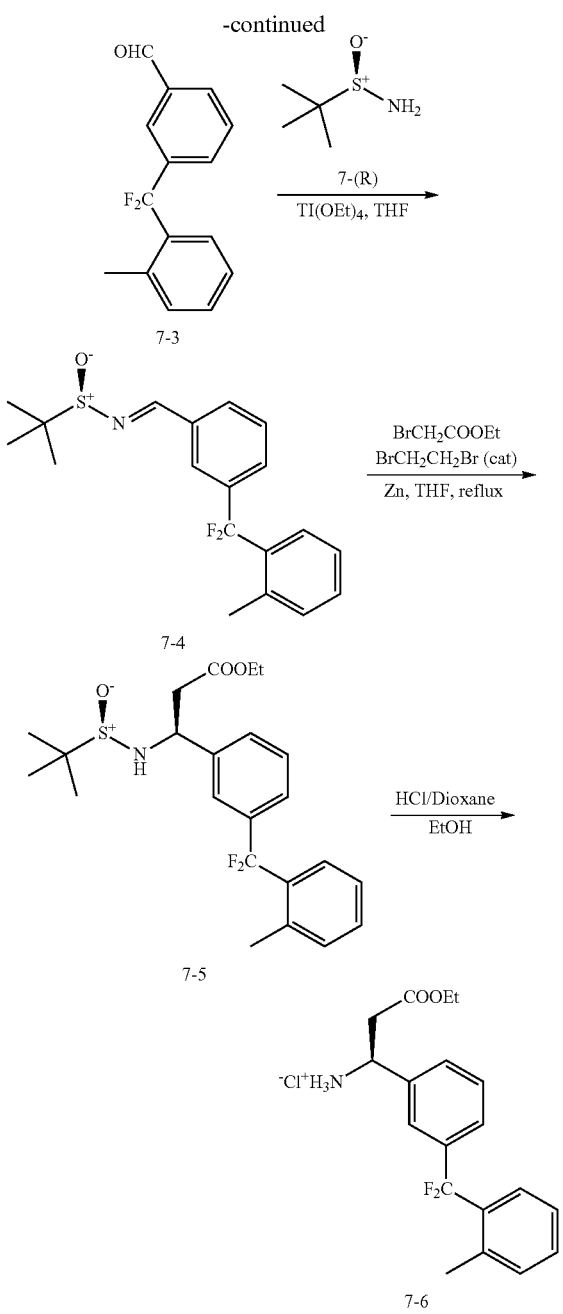

re-cooled to 0° C., and quenched with the slow addition of saturated aqueous sodium bicarbonate (vigorous gas evolution). The resulting mixture was filtered through Celite®. The aqueous layer from the filtrate was extracted three times with ethyl acetate and the four organic layers were combined, washed with brine, dried over magnesium sulfate, and filtered. This reaction was repeated using 14.27 g 7-1, 1.11 g antimony trichloride, and 9.10 mL DAST. The filtrates from the two reactions were combined, and filtered through a pad of silica gel, then concentrated. The residue was purified by silica gel chromatography, eluting with hexanes to give 1-((3-bromophenyl)difluoromethyl)-2-methylbenzene (7-2, 25.00 g) as a yellow oil.

Step Three: To each of two separate solutions of 7-2 (12.50 g, 42.1 mmol) in ether (84 mL) cooled to −78° C. under nitrogen, tert-butyllithium (1.7 M in pentane, 61.9 mL, 105.2 mmol) was added dropwise over the course of one hour. Each mixture was stirred at −78° C. for an additional one hour then N,N-dimethylformamide (16.2 mL, 210.4 mmol) was added dropwise to each. Each mixture was stirred at −78° C. for one hour then was warmed to room temperature and poured into aqueous hydrochloric acid (1 N). The mixtures from the two reactions were combined, stirred for 20 minutes, and the aqueous layer was extracted twice with ethyl acetate. The three organic layers were washed with brine, dried over magnesium sulfate, filtered and concentrated. The residue was purified by silica gel chromatography, eluting with 30% ether in hexanes to give 3-(difluoro(o-tolyl)methyl)benzaldehyde (7-3, 20.27 g) as a pale yellow oil.

Step Four: To a mixture of 7-3 (10.13 g, 41.2 mmol) and (R)-(+)-2-methyl-2-propanesulfinamide (7-R, 5.49 g, 45.3 mmol) in THF (100 mL) at room temperature under nitrogen, titanium(IV) ethoxide (1.11 mL, 5.38 mmol) was added. The resulting mixture was stirred overnight, diluted with ethyl acetate and brine, stirred an additional 20 minutes, and filtered through Celite®. The organic layer from the filtrate was separated, dried over magnesium sulfate, filtered and concentrated to give (R,E)-N-(3-(difluoro(o-tolyl)methyl)benzylidene)-2-methylpropane-2-sulfinamide (7-4, 15.57 g) as a yellow oil.

This procedure was also used to prepare (R,E)-2-methyl-N-(3-(o-tolyloxy)benzylidene)propane-2-sulfinamide;
(R,E)-N-(3-(2-methoxyphenoxy)benzylidene)-2-methylpropane-2-sulfinamide;
(R,E)-N-(3-(2-chlorophenoxy)benzylidene)-2-methylpropane-2-sulfinamide;
(R,E)-2-methyl-N-(3-(p-tolyloxy)benzylidene)propane-2-sulfinamide;
(R,E)-2-methyl-N-(3-(m-tolyloxy)benzylidene)propane-2-sulfinamide;
(R,E)-N-(3-(2,4-difluorophenoxy)benzylidene)-2-methylpropane-2-sulfinamide;
and (R,E)-N-(3-(2,6-dimethylphenoxy)benzylidene)-2-methylpropane-2-sulfinamide.

This reaction could also be accomplished by using 2.5 equivalents of $CuSO_4$ in place of titanium(IV) ethoxide and dichloromethane in place of THF. This modification was used to prepare (R,E)-2-methyl-N-((5-(2-methylbenzyl)thiophen-2-yl)methylene)propane-2-sulfinamide and (R,E)-N-((5-benzylthiophen-2-yl)methylene)-2-methylpropane-2-sulfinamide Step Five: To a mixture of zinc powder (7.28 g, 111.4 mmol) in THF (42 mL) at room temperature under nitrogen, 1,2-dibromoethane (0.2 mL) and ethyl bromoacetate (1.0 mL, 9.0 mmol) were added and the mixture was heated to reflux for 15 minutes. To this refluxing mixture, a solution Step One: To a solution of 3-bromo-2'-methylbenzophenone (7-0, 31.00 g, 111.9 mmol) in toluene (220 mL) at room temperature under nitrogen, Lawesson reagent [2,4-bis-(4-methoxyphenyl)-1,3-dithia-2,4-diphosphetane 2,4-disulfide, 90.47 g, 223.7 mmol] was added. The mixture was heated to reflux for 5 hours, cooled to room temperature and filtered through a pad of silica gel, washing with 10% ether in hexanes. The filtrate was concentrated to give (3-bromophenyl)(o-tolyl)methanethione (7-1, 29.27 g) as a dark blue liquid.

Step Two: To a solution of 7-1 (15.00 g, 51.50 mmol) in dichloromethane (25 mL) cooled to 0° C. under nitrogen, antimony trichloride (1.17 g, 5.15 mmol) was added followed by the dropwise addition of DAST [(diethylamino)sulfur trifluoride, 9.53 mL, 72.1 mmol] by syringe. The mixture was warmed to room temperature, stirred 48 hours, of 7-4 (15.57 g, 44.6 mmol) and ethyl bromoacetate (11.8 mL, 106.8 mmol) in THF (100 mL) was added dropwise. The mixture was refluxed for 3 hours, cooled to room temperature, and poured into saturated aqueous ammonium chloride. The resulting mixture was extracted three times with ethyl acetate and the combined organic layers were washed and brine, dried over magnesium sulfate, and filtered. The filtrate was concentrated and the residue was purified by silica gel column chromatography, eluting with 50% ethyl acetate in hexanes to give ethyl (S)-3-(3-(difluo (o-tolyl)methyl)phenyl)-3-((R)-1,1-dimethylethylsulfinamido)propanoate (7-5, 10.5 g) as a yellow oil.

This procedure was also used to prepare (S)-ethyl 3-((R)-1,1-dimethylethylsulfinamido)-3-(3-(o-tolyloxy)phenyl) propanoate;
ethyl (S)-3-((R)-1,1-dimethylethylsulfinamido)-3-(3-(2-methoxyphenoxy)phenyl) propanoate;
ethyl (S)-3-(4-(2-methoxyphenoxy)phenyl)-3-((R)-4-methylphenylsulfinamido) propanoate;
ethyl (S)-3-(4-(3-methoxyphenoxy)phenyl)-3-((R)-4-methylphenylsulfinamido) propanoate;
ethyl (S)-3-((R)-1,1-dimethylethylsulfinamido)-3-(3-(p-tolyloxy)phenyl)propanoate;
ethyl (S)-3-((R)-1,1-dimethylethylsulfinamido)-3-(3-(m-tolyloxy)phenyl) propanoate;
ethyl (S)-3-(3-(2,4-difluorophenoxy)phenyl)-3-((R)-1,1-dimethylethylsulfinamido) propanoate; and
ethyl (S)-3-((R)-1,1-dimethylethylsulfinamido)-3-(3-(2,6-dimethylphenoxy)phenyl) propanoate.

Step Six: To a solution of 7-5 (10.5 g, 24.4 mmol) in ethanol (50 mL), hydrochloric acid (4.0 M in dioxane, 30.5 mL, 122 mmol) was added. The mixture was stirred for 4 hours and concentrated. The residue was taken up in a mixture of ether (100 mL), hexanes (400 mL) and dichloromethane (100 mL). The mixture was heated to boiling for 10 minutes, cooled to room temperature, and filtered to give ethyl (S)-3-amino-3-(3-(difluoro(o-tolyl)methyl)phenyl) propanoate hydrochloride (7-6, 5.92 g) as a white solid.

This procedure was also used to prepare ethyl (S)-3-amino-3-(3-(o-tolyloxy)phenyl)propanoate hydrochloride;
ethyl (S)-3-amino-3-(3-(2-methoxyphenoxy)phenyl)propanoate hydrochloride;
ethyl (S)-3-amino-3-(3-(2-chlorophenoxy)phenyl)propanoate hydrochloride;
ethyl (S)-3-amino-3-(3-(p-tolyloxy)phenyl)propanoate hydrochloride;
ethyl (S)-3-amino-3-(3-(m-tolyloxy)phenyl)propanoate hydrochloride;
ethyl (S)-3-amino-3-(3-(2,4-difluorophenoxy)phenyl)propanoate hydrochloride;
and ethyl (S)-3-amino-3-(3-(2,6-dimethylphenoxy)phenyl) propanoate hydrochloride.

The product from this reaction could also be isolated as a freebase. The residue was taken up in water and was extracted with ether. The aqueous layer was basified with saturated aqueous sodium bicarbonate and extracted three times with chloroform. The chloroform extracts were combined, washed with brine, dried over magnesium sulfate, filtered and concentrated. This variation was used to prepare ethyl (S)-3-amino-3-(4-(2-methylbenzyl)phenyl)propanoate;
ethyl (S)-3-amino-3-(4-(3-methylbenzyl)phenyl)propanoate;
ethyl (S)-3-amino-3-(4-(4-methylbenzyl)phenyl)propanoate;
ethyl (S)-3-amino-3-(5-(2-methylbenzyl)thiophen-2-yl)propanoate;
and ethyl (S)-3-amino-3-(5-benzylthiophen-2-yl)propanoate.

This procedure could also be accomplished using trifluoroacetic acid in place of hydrochloric acid. The workup described above was used to isolate ethyl (S)-3-amino-3-(4-(2-methoxyphenoxy)phenyl)propanoate and ethyl (S)-3-amino-3-(4-(3-methoxyphenoxy)phenyl)propanoate as freebases.

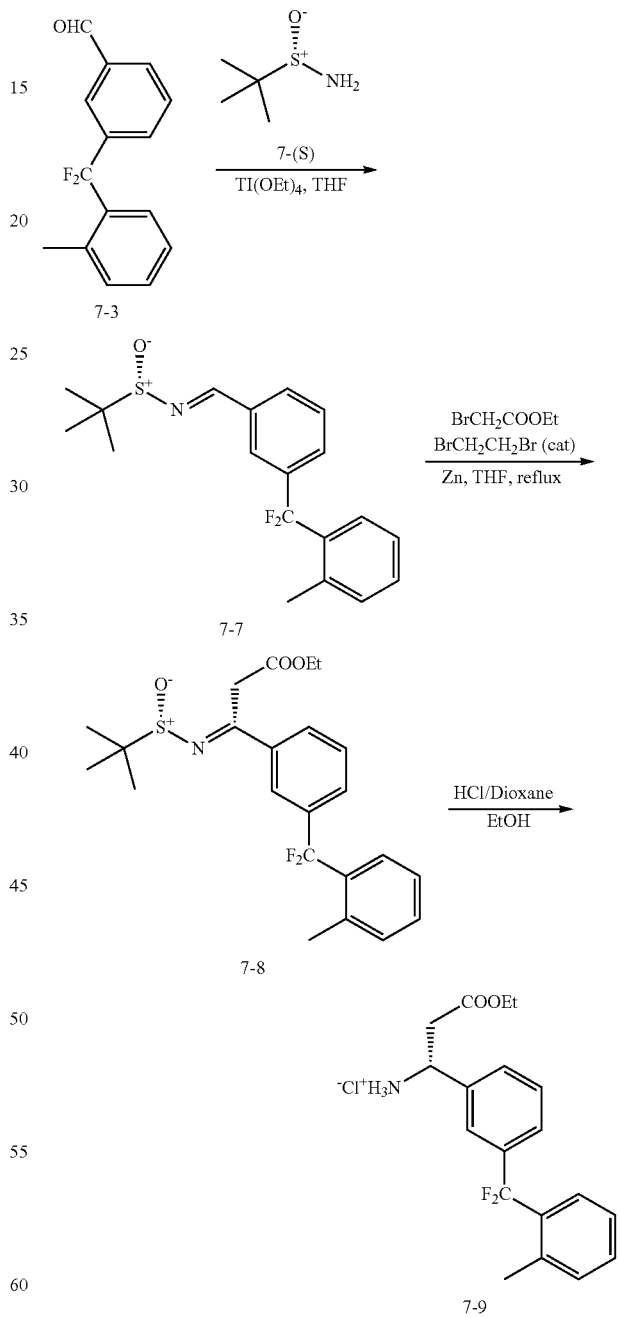

The use of (S)-(−)-2-methyl-2-propanesulfinamide (7-S) in Step Four and following through to Step Six gives ethyl (R)-3-amino-3-(3-(difluoro(o-tolyl)methyl)phenyl)propanoate hydrochloride (7-9) as a white solid.

Example 8

Synthesis of (R,E)-N-(4-(2-methoxyphenoxy)benzylidene)-4-methylbenzene sulfonamide (8-4)

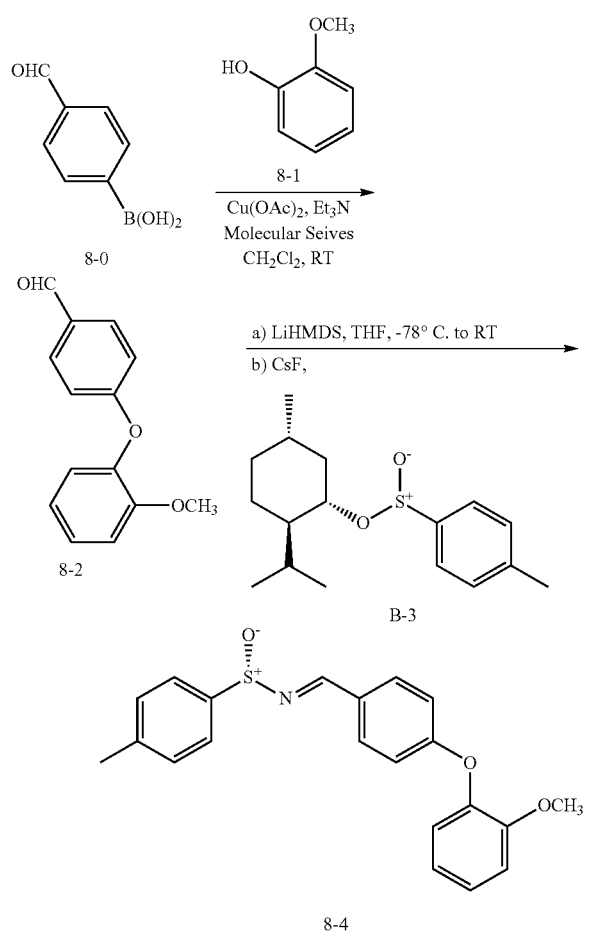

Step One: To a solution of 2-methoxyphenol (8-1, 1.5 g, 12 mmol) in dichloromethane (30 mL), molecular sieves (4 angstrom), 4-formylphenylboronic acid (8-0, 1.8 g, 12 mmol), triethylamine (1.65 mL, 12 mmol), and copper(II) acetate (0.66 g, 3.6 mmol) were added. Air from a calcium chloride packed drying tube was gently drawn through the reaction flask with vacuum for 4 hours. Vacuum was discontinued and the resulting mixture was stirred overnight, diluted with hexanes, filtered through a pad of silica gel. The filtrate was concentrated and the residue was purified by silica gel column chromatography, eluting with 5% ethyl acetate in hexanes to give 4-(2-methoxyphenoxy)benzaldehyde (8-2, 1.17 g) as a white solid.

This procedure was also used to prepare 4-(3-methoxyphenoxy)benzaldehyde and 4-(o-tolyloxy)benzaldehyde.

Step Two: To a mixture of (+)-(1S)-menthyl (R)-p-toluenesulfinate (8-3, 1.40 g, 4.7 mmol) in ether (6 mL) at −78° C. under nitrogen, lithium hexamethyldisilazide (1.0 M in THF, 4.7 mL, 4.7 mmol) was added by syringe. The mixture allowed to warm to room temperature then stirred for 4 hours, and a solution of 8-2 (1.17 g, 4.3 mmol) in ether (2 mL) was added by syringe followed by cesium fluoride (0.71 g, 4.7 mmol). The mixture was stirred overnight then was diluted with water and ether. The aqueous layer was extracted twice with ether and the combined organic layers were washed with brine, dried over magnesium sulfate, filtered and concentrated. The residue was purified by silica gel column chromatography, eluting with 5% increasing to 25% ethyl acetate in hexanes to give (R,E)-N-(4-(2-methoxyphenoxy)benzylidene)-4-methylbenzene sulfinamide (8-4, 1.11 g) as a yellow oil. This material contained a trace of 4-1 but was used without further purification.

This procedure was also used to prepare (R,E)-N-(4-(3-methoxyphenoxy) benzylidene)-4-methylbenzenesulfinamide.

This procedure was modified by omitting the addition of cesium fluoride after the addition of the aldehyde. This modification was used to prepare (R,E)-4-methyl-N-(4-(2-methylbenzyl)benzylidene)benzenesulfinamide, (R,E)-4-methyl-N-(4-(3-methylbenzyl)benzylidene)benzenesulfinamide, and (R,E)-4-methyl-N-(4-(4-methylbenzyl)benzylidene)benzenesulfinamide.

Example 9

Synthesis of ethyl (E)-3-(4-(p-tolyloxy)phenyl)acrylate (9-2)

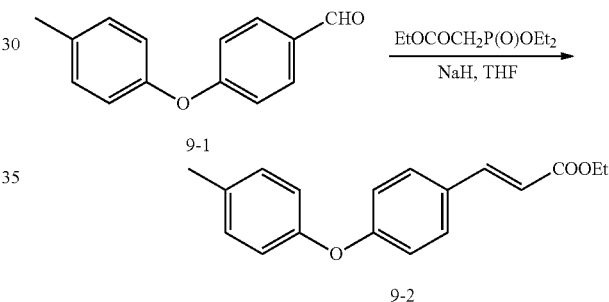

Step One: To suspension of sodium hydride (60% dispersion in mineral oil, 215 mg, 5.4 mmol) in THF (5.4 mL) cooled to 0° C., triethyl phosphonoacetate (1.10 mL, 5.4 mmol) was added dropwise by syringe. The resulting mixture was stirred at 0° C. for 20 minutes and a solution of 9-1 (prepared according to the procedure in example 8 step one, 1.10 g, 4.9 mmol) in THF (10 mL) was added by syringe. The mixture was stirred for 2 hour, carefully quenched with saturated aqueous sodium bicarbonate, and extracted three times with ethyl acetate. The combined organic layers were washed with brine, dried, filtered and concentrated. The residue was purified by silica gel chromatography, eluting with 10% ethyl acetate in hexanes to give ethyl (E)-3-(4-(p-tolyloxy)phenyl)acrylate (9-2, 560 mg) as a yellow oil.

This procedure was also used to prepare ethyl (E)-3-(3-phenoxyphenyl)acrylate,
ethyl (E)-3-(4-(o-tolyloxy)phenyl)acrylate,
ethyl (E)-3-(3-(3-methylbenzyl)phenyl)acrylate,
ethyl (E)-3-(3-(4-methylbenzyl)phenyl)acrylate,
ethyl (E)-3-(3-(2-methylbenzyl)phenyl)acrylate,
ethyl (E)-3-(4-benzylphenyl)acrylate,
ethyl (E)-3-(3-(3-(trifluoromethyl)benzyl)phenyl)acrylate,
ethyl (E)-3-(3-(4-(trifluoromethyl)benzyl)phenyl)acrylate,
ethyl (E)-3-(3-(4-(difluoromethoxy)benzyl)phenyl)acrylate,
ethyl (E)-3-(3-(2-ethylbenzyl)phenyl)acrylate,
ethyl (E)-3-(3-(2-fluorobenzyl)phenyl)acrylate, ethyl (E)-3-(3-(2,6-dimethylbenzyl)phenyl)acrylate,
ethyl (E)-3-(3-(2-methoxybenzyl)phenyl)acrylate, and
ethyl (E)-3-(3-(5-fluoro-2-methylbenzyl)phenyl)acrylate.

Example 10

Synthesis of ethyl (S)-3-amino-3-(3-benzylphenyl)propanoate (10-9)

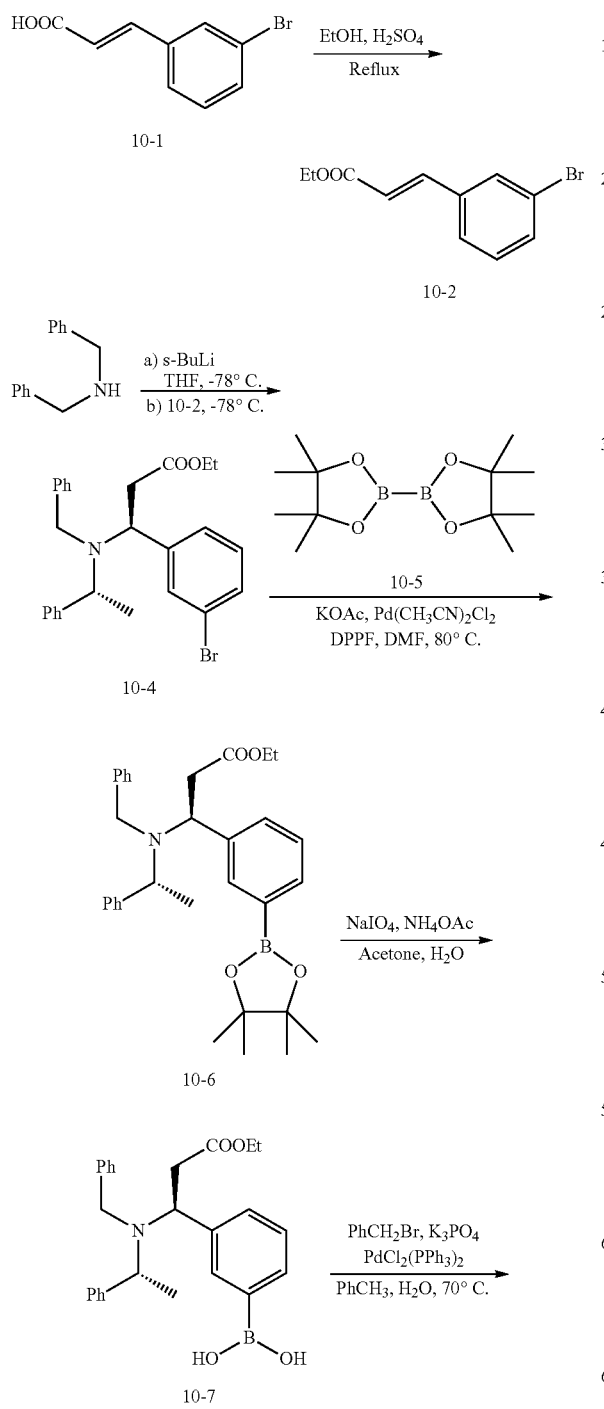

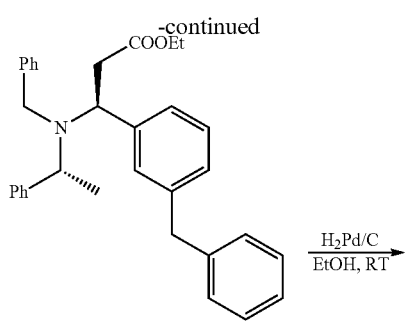

Step One: To a solution of 3-bromocinnamic acid (29.0 g, 127.7 mmol) in ethanol (450 mL), catalytic concentrated sulfuric (about 10 drops) was added. The reaction was heated to reflux overnight, concentrated under reduced pressure (to approximately 0.1 L), diluted with hot ethyl acetate, and washed with water (3 times) and saturated brine. The organic layer was dried over magnesium sulfate, filtered, and concentrated under reduced pressure to give ethyl (E)-3-(3-bromophenyl)acrylate (10-1, 32.5 g).

Step Two: To a solution of (R)-(+)-N-benzyl-α-methylbenzylamine (20.3 g, 96 mmol) in THF (150 mL) cooled to −78° C. under a nitrogen atmosphere, s-butyllithium (1.3 M in cyclohexane, 77 mL, 100 mmol) was added dropwise over 30 minutes. The mixture was stirred for 30 minutes, and a solution of 10-1 (20.4 g, 80 mmol) in THF (100 mL) was added dropwise over 30 minutes. The resulting solution was stirred at −78° C. for 3 hours, ethanol (8 mL) was added and the mixture was poured onto saturated aqueous ammonium chloride. The resulting mixture was extracted with ethyl acetate (3 times), and the organic layers were combined, washed with brine, dried over magnesium sulfate (anhydrous), filtered and concentrated under reduced pressure. The residue was purified by chromatography on silica gel, eluting with hexanes increasing to hexanes:acetate (9:1) to give ethyl (S)-3-(benzyl((R)-1-phenylethyl)amino)-3-(3-bromophenyl)propanoate (10-2, 27.19 g).

In general, n-butyllithium could be used interchangeably with s-butyllithium. This procedure was also used to prepare ethyl (S)-3-(benzyl((R)-1-phenylethyl)amino)-3-(3-phenoxyphenyl)propanoate,
ethyl (S)-3-(benzyl((R)-1-phenylethyl)amino)-3-(4-(p-tolyloxy)phenyl)propanoate,
ethyl (S)-3-(benzyl((R)-1-phenylethyl)amino)-3-(4-(o-tolyloxy)phenyl)propanoate,
ethyl (S)-3-(benzyl((R)-1-phenylethyl)amino)-3-(3-(3-methylbenzyl)phenyl) propanoate,
ethyl (S)-3-(benzyl((R)-1-phenylethyl)amino)-3-(3-(4-methylbenzyl)phenyl) propanoate, ethyl (S)-3-(benzyl((R)-1-phenylethyl)amino)-3-(3-(2-methylbenzyl)phenyl) propanoate,
ethyl (S)-3-(benzyl((R)-1-phenylethyl)amino)-3-(4-benzylphenyl)propanoate,
ethyl (S)-3-(benzyl((R)-1-phenylethyl)amino)-3-(3-(3-(trifluoromethyl)benzyl) phenyl)propanoate,
ethyl (S)-3-(benzyl((R)-1-phenylethyl)amino)-3-(3-(4-(trifluoromethyl)benzyl) phenyl) propanoate,
ethyl (S)-3-(benzyl((R)-1-phenylethyl)amino)-3-(3-(2-(difluoromethoxy)benzyl) phenyl)propanoate,
ethyl (S)-3-(benzyl((R)-1-phenylethyl)amino)-3-(3-(2-ethylbenzyl)phenyl) propanoate,
ethyl (S)-3-(benzyl((R)-1-phenylethyl)amino)-3-(3-(2-fluorobenzyl)phenyl) propanoate,
ethyl (S)-3-(benzyl((R)-1-phenylethyl)amino)-3-(3-(2,6-dimethylbenzyl)phenyl) propanoate,
ethyl (S)-3-(benzyl((R)-1-phenylethyl)amino)-3-(3-(2-methoxybenzyl)phenyl) propanoate, and
ethyl (S)-3-(benzyl((R)-1-phenylethyl)amino)-3-(3-(5-fluoro-2-methylbenzyl) phenyl) propanoate.

Step Three: A mixture of Pd(CH$_3$CN)$_2$Cl$_2$ (39 mg, 0.15 mmol) and DPPF (84 mg, 0.15 mmol) in DMF (5 mL) at room temperature under nitrogen was stirred for 30 minutes. To the resulting mixture, a solution of 10-2 (2.50 g, 5.05 mmol) in DMF (15 mL), bis(pinacolato)diboron (1.41 g, 5.56 mmol) and potassium acetate (1.49 g, 15.2 mmol) were added. The resulting mixture was heated to 80° C. under nitrogen overnight then was cooled to room temperature and diluted with ethyl acetate. The mixture was washed with saturated aqueous ammonium chloride and brine, dried over magnesium sulfate, filtered and concentrated. The residue was purified by silica gel chromatography to give ethyl (S)-3-(benzyl((R)-1-phenylethyl)amino)-3-(3-(4,4,5,5-tetramethyl-1,3,2-dioxaborolan-2-yl)phenyl)propanoate (10-3, 2.42 g).

Step Four: To a solution of 10-3 (1.00 g, 1.84 mmol) in acetone (50 mL), sodium periodate (789 mg, 3.69 mmol), ammonium acetate (284 mg, 3.69 mmol) and water (50 mL) were added. The resulting mixture was stirred at room temperature for 2 days then the acetone was removed by rotary evaporation. The aqueous mixture was extracted three times with chloroform and the combined organic layers were washed with brine, dried over magnesium sulfate, filtered and concentrated to give 3-((S)-1-(benzyl((R)-1-phenylethyl)amino)-3-ethoxy-3-oxopropyl)phenylboronic acid (10-4, 689 mg) as a brown foam.

Step Five: To a mixture of 10-4 (150 mg, 0.36 mmol) and bis(triphenylphoshine)palladium(II) dichloride (95 mg, 0.13 mmol) in a mixture of toluene and water (1:1, 3.3 mL) at room temperature under nitrogen, benzyl bromide (0.040 mL, 0.33 mmol), and tribasic potassium phosphate (140 mg, 0.66 mmol) and were added. The mixture was deoxygenated (toggle between vacuum and nitrogen gas 5 times), heated to 70° C. overnight, cooled to room temperature, and aqueous HCl (2N) was added. The mixture extracted twice with ethyl acetate, and the combined organic layers were washed with water and brine, dried, filtered and concentrated. The residue was purified by column chromatography on silica gel, eluting with 25% increasing to 50% ethyl acetate in hexanes to give ethyl (S)-3-(benzyl((R)-1-phenylethyl)amino)-3-(3-benzylphenyl)propanoate (10-5, 91 mg).

This procedure was also used to prepare ethyl (S)-3-(benzyl((R)-1-phenylethyl)amino)-3-(3-(2-(trifluoromethyl)benzyl)phenyl)propanoate,
3-(2-chlorobenzyl)benzaldehyde (from 3-formylphenylboronic acid),
3-(3-chlorobenzyl)benzaldehyde,
3-(3-methyl benzyl)benzaldehyde,
3-(2-methyl benzyl)benzaldehyde,
3-(2-fluorobenzyl)benzaldehyde,
3-(2,6-dimethylbenzyl)benzaldehyde,
3-(5-fluoro-2-methylbenzyl)benzaldehyde,
3-(4-chlorobenzyl)benzaldehyde,
3-(4-methyl benzyl)benzaldehyde,
4-(2-chlorobenzyl)benzaldehyde,
3-(3-(trifluoromethyl)benzyl)benzaldehyde,
3-(4-(trifluoromethyl)benzyl)benzaldehyde,
3-(2-(difluoromethoxy)benzyl)benzaldehyde,
3-(2-ethylbenzyl)benzaldehyde,
3-(2-methoxybenzyl)benzaldehyde, and
4-benzylbenzaldehyde (from 4-formylphenylboronic acid).

This procedure could also be performed using DMF instead of toluene, heating to 70° C. instead of 70° C. This modification was used to prepare 4-(2-methylbenzyl)benzaldehyde,
4-(3-methylbenzyl)benzaldehyde, and
4-(4-methyl benzyl)benzaldehyde.

This procedure could also be accomplished by using sodium bicarbonate and dimethoxyethane instead of tribasic potassium phosphate and toluene. This variation was used to prepare 5-(2-methylbenzyl)thiophene-2-carbaldehyde (from 5-formyl-2-thiopheneboronic acid) and 5-benzylthiophene-2-carbaldehyde.

Step Six: To a solution of 10-5 (170 mg, 0.45 mmol) in ethanol (9 mL), glacial acetic acid (0.1 mL), palladium metal on carbon (Degussa type E101 NE/W, 50% H$_2$O, 10% Pd dry weight basis, 100 mg, 0.047 mmol Pd). The atmosphere was replaced with hydrogen (toggling between vacuum and hydrogen from a balloon several times) and the reaction was stirred overnight. By TLC, the reaction had stalled so the mixture was filtered through Celite® and the filtrate was concentrated. The material was reset using the same amounts of reagents as before then was heated to 40° C. for one hour. The reaction had gone to completion by TLC analysis the mixture was filtered and concentrated as before. The residue was brought up in ethyl acetate, washed with saturated aqueous sodium carbonate, and the organic layer was dried over magnesium sulfate, filtered, and concentrated. The residue was purified by column chromatography on silica gel, eluting with ethyl acetate in hexanes, followed by 10% methanol in chloroform to give ethyl (S)-3-amino-3-(3-benzylphenyl)propanoate (10-6, 47 mg).

When preparing other analogs, this reaction generally proceeded to completion after the initial overnight period. This method was also used to prepare ethyl (S)-3-amino-3-(3-phenoxyphenyl)propanoate,
ethyl (S)-3-amino-3-(4-(p-tolyloxy)phenyl)propanoate,
ethyl (S)-3-amino-3-(4-(o-tolyloxy)phenyl)propanoate,
ethyl (S)-3-amino-3-(3-(3-methylbenzyl)phenyl)propanoate,
ethyl (S)-3-amino-3-(3-(4-methylbenzyl)phenyl)propanoate,
ethyl (S)-3-amino-3-(3-(2-methylbenzyl)phenyl)propanoate,
ethyl (S)-3-amino-3-(3-(2-(trifluoromethyl)benzyl)phenyl) propanoate,
ethyl (S)-3-amino-3-(4-benzylphenyl)propanoate,
ethyl (S)-3-amino-3-(3-(3-(trifluoromethyl)benzyl)phenyl) propanoate,
ethyl (S)-3-amino-3-(3-(4-(trifluoromethyl)benzyl)phenyl) propanoate,
ethyl (S)-3-amino-3-(3-(2-(difluoromethoxy)benzyl)phenyl)propanoate, ethyl (S)-3-amino-3-(3-(2-ethylbenzyl)phenyl)propanoate,
ethyl (S)-3-amino-3-(3-(2-fluorobenzyl)phenyl)propanoate,
ethyl (S)-3-amino-3-(3-(2,6-dimethylbenzyl)phenyl)propanoate,
ethyl (S)-3-amino-3-(3-(2-methoxybenzyl)phenyl)propanoate, and
ethyl (S)-3-amino-3-(3-(5-fluoro-2-methylbenzyl)phenyl)propanoate.

Example 11

Synthesis of ethyl (S)-3-(4-(2-methylbenzyl)phenyl)-3-((R)-4-methylphenyl sulfinamido) propanoate (11-2)

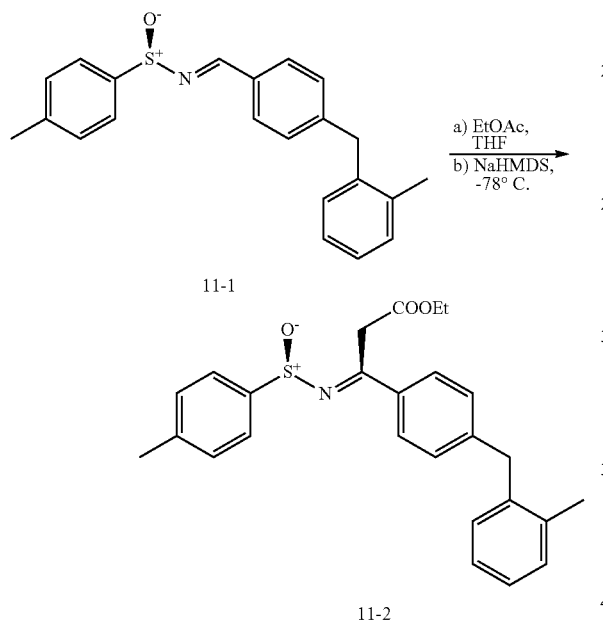

Step One: To a solution of ethyl acetate (0.63 mL, 6.5 mmol) in THF (19 mL) at −78° C. under nitrogen, sodium hexamethyldisilazide (1.0 M in THF, 6.5 mL, 6.5 mmol) was added by syringe. The resulting mixture was stirred for 30 minutes, then a solution of 11-1 (prepared according to the procedure described in example four step one, 1.50 g, 4.3 mmol) in THF (10 mL) was added. The mixture was stirred at −78° C. for 2.5 hours then was quenched with saturated aqueous ammonium chloride. The mixture was warmed to room temperature and extracted with ethyl acetate. The organic layer was dried over magnesium sulfate, filtered and concentrated to give ethyl (S)-3-(4-(2-methylbenzyl)phenyl)-3-((R)-4-methylphenylsulfinamido)propanoate (11-2, 1.91 g). This material was used without further purification.

This procedure was also used to prepare ethyl (S)-3-(3-(2-chlorophenoxy)phenyl)-3-((R)-1,1-dimethylethylsulfinamido)propanoate,
ethyl (S)-3-((R)-1,1-dimethylethylsulfinamido)-3-(5-(2-methylbenzyl)thiophen-2-yl) propanoate,
ethyl (S)-3-(5-benzylthiophen-2-yl)-3-((R)-1,1-dimethylethylsulfinamido) propanoate,
ethyl (S)-3-(4-(3-methylbenzyl)phenyl)-3-((R)-4-methylphenylsulfinamido) propanoate, and
ethyl (S)-3-(4-(4-methylbenzyl)phenyl)-3-((R)-4-methylphenyl sulfinamido) propanoate.

Example 12

Synthesis of 3-(p-tolyloxy)benzaldehyde (12-4)

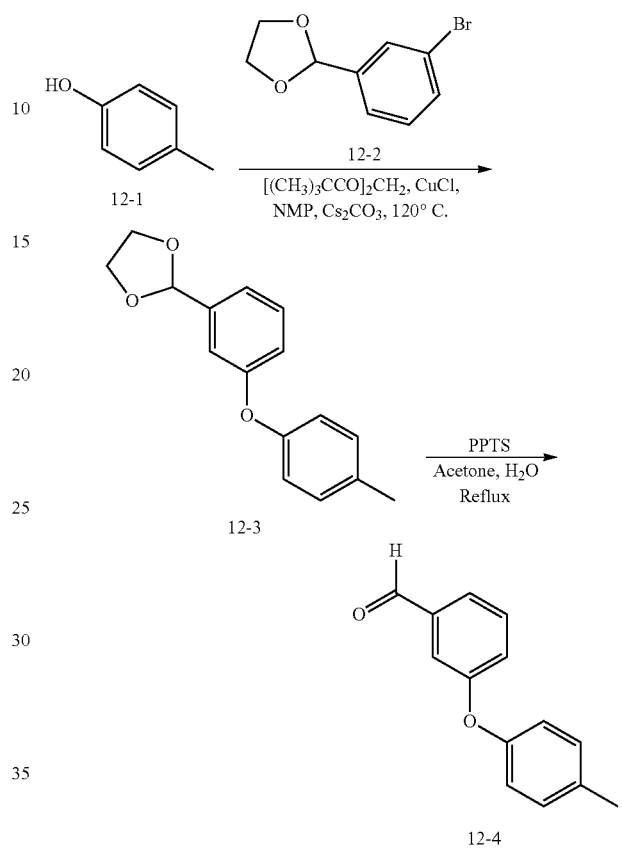

Step One: To a suspension of cesium carbonate (2.84 g, 8.72 mmol) in NMP (7 mL) at room temperature, p-cresol (12-1, 0.90 mL, 8.7 mmol) was added. The mixture was deoxygenated (toggle three times between vacuum and nitrogen gas), and 2-(3-bromophenyl)-1,3-dioxolane (12-2, 0.66 mL, 4.4 mmol), 2,2,6,6-tetramethyl-3,5-heptanedione (0.089 mL, 0.44 mmol) and CuCl (215 mg, 2.18 mmol) were added. The mixture was heated to 120° C. overnight, cooled to room temperature and diluted with ether. The mixture was filtered through Celite®, washing with ether. The filtrate was washed with aqueous HCl (2N), aqueous NaOH (2N) and brine, dried over magnesium sulfate, filtered and concentrated. The residue was purified by silica gel chromatography, eluting with 7% ethyl acetate in hexanes to give 2-(3-(p-tolyloxy)phenyl)-1,3-dioxolane (12-3, 719 mg) as a pale yellow oil.

This procedure was also used to prepare 2-(3-(o-tolyloxy)phenyl)-1,3-dioxolane,
2-(3-(2-methoxyphenoxy)phenyl)-1,3-dioxolane,
2-(3-(2-chlorophenoxy)phenyl)-1,3-dioxolane,
2-(3-(m-tolyloxy)phenyl)-1,3-dioxolane,
2-(3-(2,4-difluorophenoxy)phenyl)-1,3-dioxolane, and
2-(3-(2,6-dimethylphenoxy)phenyl)-1,3-dioxolane.

In a modification of this procedure, 4-bromobenzaldehyde dimethyl acetal was used instead of the dioxolane. In this reaction, an additional wash with aqueous HCl was done, and the diethyl acetal hydrolyzed during workup to give 4-(p-tolyloxy)benzaldehyde.

Step Two: A solution of 12-3 (719 mg, 2.81 mmol) and PPTS (176 mg, 0.70 mmol) in acetone (3.5 mL) and water (3.5 mL) was heated to reflux for 90 minutes then was cooled to room temperature and diluted with dichloromethane. The organic layer was washed with aqueous HCl (1 N), saturated aqueous sodium bicarbonate, and brine, dried over magnesium sulfate, filtered, and concentrated to give 3-(p-tolyloxy)benzaldehyde (12-4, 507 mg) as a pale yellow oil.

This procedure was also used to prepare 3-(o-tolyloxy)benzaldehyde,
3-(2-methoxyphenoxy)benzaldehyde,
3-(2-chlorophenoxy)benzaldehyde,
3-(m-tolyloxy)benzaldehyde,
3-(2,4-difluorophenoxy)benzaldehyde, and
3-(2,6-dimethylphenoxy)benzaldehyde.

Example 13

Synthesis of 1-(bromomethyl)-2-ethylbenzene (9-1)

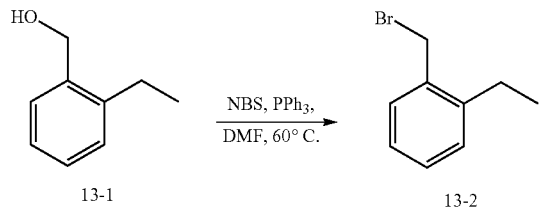

Step One: To a solution of (2-ethylphenyl)methanol (13-1, 1.00 g, 7.3 mmol) in DMF (25 mL) at room temperature under nitrogen, NBS (2.6 g, 14.6 mmol) and triphenylphosphine (4.03 g, 15.3 mmol) were added sequentially. The mixture was heated to 50° C. overnight, cooled to room temperature and diluted with water and dichloromethane. The aqueous layer was extracted twice more with dichloromethane and the organic layers were combined, washed with brine, dried, filtered and concentrated. The residue was purified by silica gel column chromatography, eluting with 10% ethyl acetate in hexanes to give 1-(bromomethyl)-2-ethylbenzene (13-2, 1.1 g) as an oil.

Example 14

Synthesis of ethyl 3-amino-3-(3-phenoxy)phenyl) propanoate (14-3)

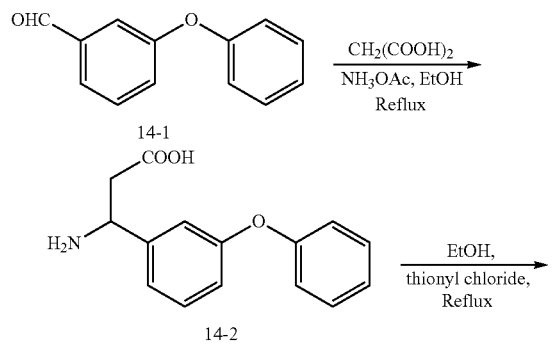

-continued

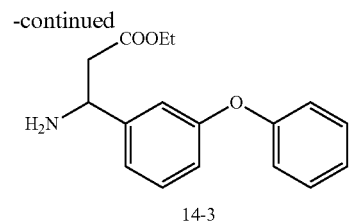

14-3

Step One: A solution of 3-phenoxybenzaldehyde (14-1, 1.47 g, 7.4 mmol), malonic acid (0.92 g, 8.9 mmol) and ammonium acetate (1.50 g, 14.8 mmol) in absolute ethanol (30 mL) was refluxed overnight then cooled to room temperature. The suspension was filtered, and the white solid was dried under vacuum to give 3-amino-3-(3-phenoxyphenyl)propanoic acid (14-2).

This procedure was also used to prepare
3-amino-3-(3-(2-chlorobenzyl)phenyl)propanoic acid,
3-amino-3-(3-(3-chlorobenzyl)phenyl)propanoic acid,
3-amino-3-(3-(4-chlorobenzyl)phenyl)propanoic acid, and
3-amino-3-(4-(2-chlorobenzyl)phenyl)propanoic acid.

Step Two: To a mixture of 14-2 (250 mg, 0.97 mmol) in absolute ethanol under nitrogen, thionyl chloride (0.095 mL, 1.5 mmol) was added dropwise. The mixture was refluxed for 5 hours then cooled to room temperature and concentrated to a volume of approximately 10 mL. The mixture was diluted with ethyl acetate, and washed with saturated aqueous NaHCO₃. The organic layer was dried, filtered and concentrated to give ethyl 3-amino-3-(3-phenoxyphenyl)propanoate (14-3, 153 mg).

This procedure was also used to prepare ethyl 3-amino-3-(4-(2-chlorobenzyl)phenyl)propanoate.

This procedure was modified by using p-toluenesulfonic acid in place of thionyl chloride. This modification was used to prepare:
ethyl 3-amino-3-(3-(2-chlorobenzyl)phenyl)propanoate,
ethyl 3-amino-3-(3-(3-chlorobenzyl)phenyl)propanoate, and
ethyl 3-amino-3-(3-(4-chlorobenzyl)phenyl)propanoate.

Example 15

Synthesis of t-butyl 3-amino-3-(3-(2-methylbenzyl) phenyl) propanoate (15-2)

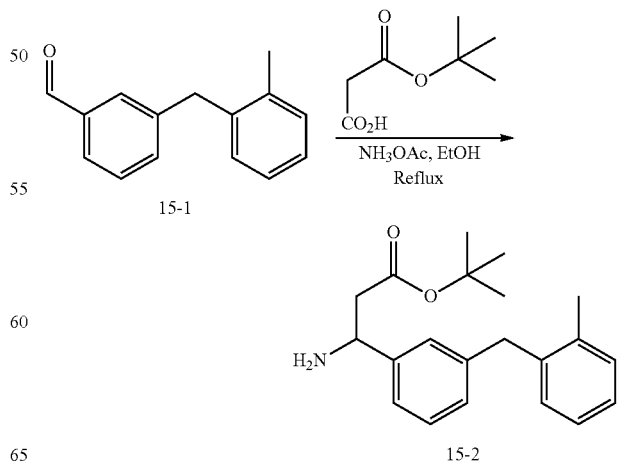

A solution of 3-(2-methylbenzyl)benzalahyde (15-1), t-butyl hydrogen malonate and ammonium acetate in absolute ethanol is refluxed for 12 hours and then cooled to room temperature. The majority of the ethanol is removed under vacuo and the residual materials taken up in diethyl ether. The ether solution is washed with sodium bicarbonate solution, dried (MgSO$_4$), filtered and the ether solution condensed in vacuo to yield compound 15-2.

Example 16

Synthesis of methyl 3-amino-3-(3-(2-methylbenzyl)phenyl) propanoate (16-2)

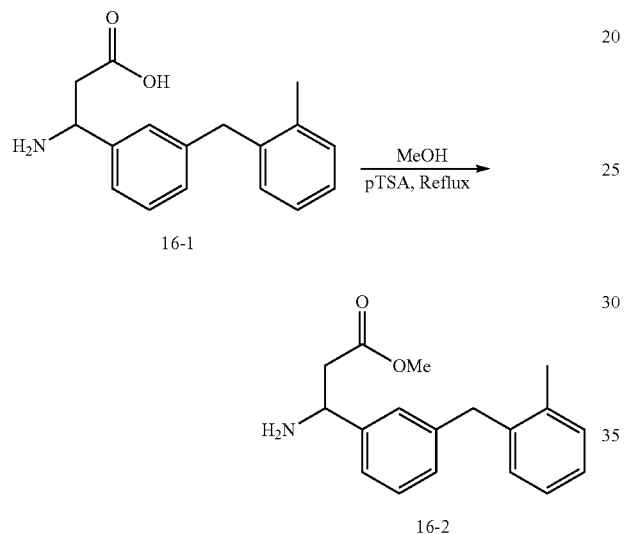

A solution of 3-amino-3-(3-(2-methylbenzyl)phenyl) propanoic acid (16-1) and a catalytic amount of p-toluene sulfonic acid in absolute methanol is refluxed for 12 hours and then cooled to room temperature. The majority of the methanol is removed under vacuo and the residual materials taken up in diethyl ether. The ether solution is washed with NaHCO$_3$ solution, dried (MgSO$_4$), filtered and the ether solution condensed in vacuo to yield compound 16-2.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A compound of formula I having a chemical structure of

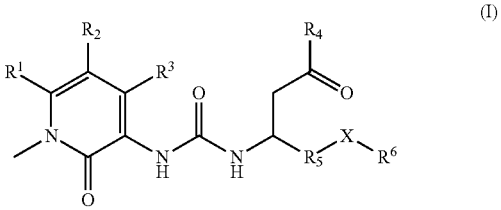

(I)

wherein $R^1$ and $R^2$ are independently hydrogen, halogen, $C_{1-4}$ alkyl, $C_{3-6}$ cycloalkyl, or arylalkyl;

$R^3$ is hydroxyl or oxido paired with a pharmaceutically acceptable cation;

$R^4$ is hydroxyl, $C_{1-4}$ alkyoxy, or oxido paired with a pharmaceutically acceptable cation;

$R^5$ is aryl, heteroaryl or arylalkyl which is substituted with one or more of $C_{1-4}$ alkyl, alkoxy, aryloxy, halogen, haloalkoxy, —CF$_3$, hydroxyl, —OCF$_3$, aryl, —OCF$_2$H, —OCF$_2$CF$_2$H, —O(C$_{3-6}$ cycloalkyl), —OCH$_2$CF$_3$, thioalkoxy, dialkylamino, $C_{3-6}$ cycloalkyl, haloalkyl;

X is CH$_2$, O, or CF$_2$;

$R^6$ is $C_{1-4}$ alkyl, aryl, heteroaryl which is substituted with one or more of $C_{1-4}$ alkyl, alkoxy, aryloxy, halogen, haloalkoxy, —CF$_3$, hydroxyl, —OCF$_3$, aryl, —OCF$_2$H, —OCF$_2$CF$_2$H, —O(C$_{3-6}$ cycloalkyl), —OCH$_2$CF$_3$, thioalkoxy, dialkylamino, $C_{3-6}$ cycloalkyl, haloalkyl; or a pharmaceutically acceptable salt form or stereoisomer(s) thereof.

2. The compound of claim 1, wherein $R^4$ is hydroxyl, methoxy, ethoxy or t-butoxy or oxido paired with a pharmaceutically acceptable cation.

3. The compound of claim 1, wherein $R^3$ is hydroxyl or oxido paired with a pharmaceutically acceptable cation.

4. The compound of claim 1, wherein the compound of formula I is a compound of formula IA having a chemical structure of

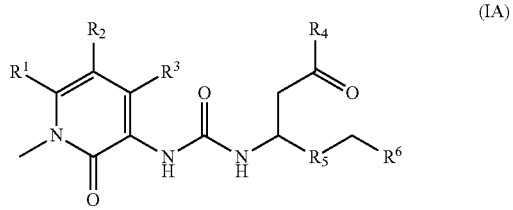

(IA)

wherein, $R^1$, $R^2$, $R^3$, $R^4$, $R^5$, and $R^6$ are as defined in claim 1; or a pharmaceutically acceptable salt or stereoisomer(s) thereof.

5. The compound of claim 1, wherein the compound of formula I is a compound of formula IB having a chemical structure of

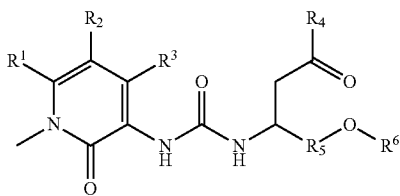

(IB)

wherein, $R^1$, $R^2$, $R^3$, $R^4$, $R^5$, and $R^6$ are as defined in claim 1; or a pharmaceutically acceptable salt or stereoisomer(s) thereof.

6. The compound of claim 1, wherein the compound of formula I is a compound of formula IC having a chemical structure of

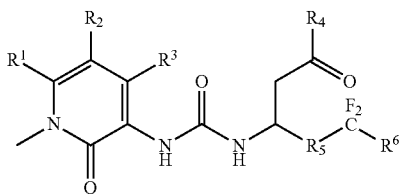

(IC)

wherein, $R^1$, $R^2$, $R^3$, $R^4$, $R^5$, and $R^6$ are the same as defined in claim 1; or a pharmaceutically acceptable salt or stereoisomers thereof.

7. The compound of claim 1, wherein the pharmaceutically acceptable salt is the mono or disodium sodium salt.

8. The compound of claim 1, wherein the stereoisomer is of the (S)-configuration.

9. A pharmaceutical composition, comprising at least one compound of claim 1 and one or more pharmaceutically acceptable carriers.

10. A compound of formula II having the chemical structure of

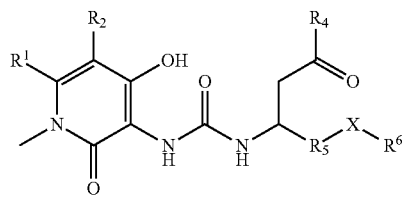

(II)

wherein
$R^1$ and $R^2$ are independently hydrogen or methyl;
$R^4$ is hydroxyl, $C_{1-4}$ alkyoxy, or oxido paired with a pharmaceutically acceptable cation;
$R^5$ is, aryl, heteroaryl or arylalkyl which is substituted with one or more of $C_{1-4}$ alkyl, alkoxy, aryloxy, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl, haloalkyl;
X is $CH_2$, O, or $CF_2$; and
$R^6$ is $C_{1-4}$ alkyl, aryl, heteroaryl which is substituted with one or more of $C_{1-4}$ alkyl, alkoxy, aryloxy, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl, haloalkyl; or a pharmaceutically acceptable salt or stereoisomer(s) thereof.

11. The compound of claim 10, wherein the compound of formula II is a compound of formula II A having a chemical structure of

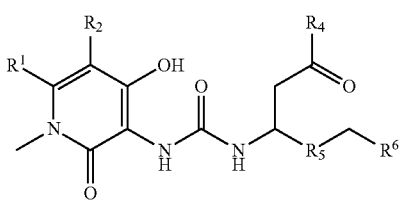

(IIA)

wherein, $R^1$, $R^2$, $R^4$, $R^5$, and $R^6$ are the same as defined in claim 10; or a pharmaceutically acceptable salt or stereoisomer(s) thereof.

12. The compound of claim 10, wherein the compound of formula II is a compound of formula II B having a chemical structure of

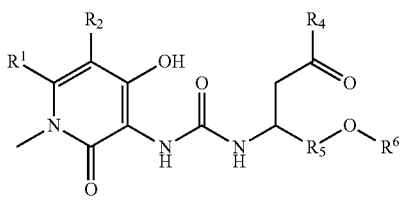

(IIB)

wherein $R^1$, $R^2$, $R^4$, $R^5$, and $R^6$ are the same as defined in claim 10; or a pharmaceutically acceptable salt or stereoisomer(s) thereof.

13. The compound of claim 10, wherein the compound of formula II is a compound of formula II C having a chemical structure of

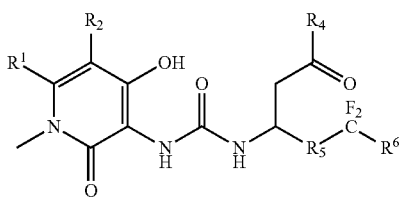

(IIC)

wherein, $R^1$, $R^2$, $R^4$, $R^5$, and $R^6$ are the same as defined in claim 10; or a pharmaceutically acceptable salt or stereoisomer(s) thereof.

14. A compound that is:
ethyl 3-(3-(4-hydroxy-1,5-dimethyl-2-oxo-1,2-dihydropyridin-3-yl)ureido)-3-(3-phenoxyphenyl)propanoate,
ethyl (S)-3-(3-(4-hydroxy-1,5-dimethyl-2-oxo-1,2-dihydropyridin-3-yl)ureido)-3-(3-phenoxyphenyl)propanoate,
ethyl (S)-3-(3-benzylphenyl)-3-(3-(4-hydroxy-1,5-dimethyl-2-oxo-1,2-dihydropyridin-3-yl)ureido)propanoate,
ethyl 3-(3-(2-chlorobenzyl)phenyl)-3-(3-(4-hydroxy-1,5-dimethyl-2-oxo-1,2-dihydropyridin-3-yl)ureido)propanoate, ethyl 3-(3-(3-chlorobenzyl)phenyl)-3-(3-(4-hydroxy-1,5-dimethyl-2-oxo-1,2-dihydropyridin-3-yl)ureido)propanoate,
ethyl 3-(3-(4-chlorobenzyl)phenyl)-3-(3-(4-hydroxy-1,5-dimethyl-2-oxo-1,2-dihydropyridin-3-yl)ureido)propanoate,
ethyl (S)-3-(4-(2-chlorobenzyl)phenyl)-3-(3-(4-hydroxy-1,5-dimethyl-2-oxo-1,2-dihydropyridin-3-yl)ureido)propanoate,
ethyl (S)-3-(3-(4-hydroxy-1,5-dimethyl-2-oxo-1,2-dihydropyridin-3-yl)ureido)-3-(3-(2-methylbenzyl)phenyl)propanoate,
ethyl (S)-3-(3-(4-hydroxy-1,5-dimethyl-2-oxo-1,2-dihydropyridin-3-yl)ureido)-3-(3-(3-methylbenzyl)phenyl)propanoate,
ethyl (S)-3-(3-(4-hydroxy-1,5-dimethyl-2-oxo-1,2-dihydropyridin-3-yl)ureido)-3-(3-(4-methylbenzyl)phenyl)propanoate,
ethyl (S)-3-(3-(4-hydroxy-1,6-dimethyl-2-oxo-1,2-dihydropyridin-3-yl)ureido)-3-(4-(2-methoxyphenoxy)phenyl)propanoate,
ethyl (S)-3-(3-(4-hydroxy-1,6-dimethyl-2-oxo-1,2-dihydropyridin-3-yl)ureido)-3-(4-(3-methoxyphenoxy)phenyl)propanoate,
ethyl (S)-3-(3-(4-hydroxy-1,6-dimethyl-2-oxo-1,2-dihydropyridin-3-yl)ureido)-3-(3-(p-tolyloxy)phenyl)propanoate,
ethyl (S)-3-(3-(4-hydroxy-1,6-dimethyl-2-oxo-1,2-dihydropyridin-3-yl)ureido)-3-(3-(2-methylbenzyl)phenyl)propanoate,
ethyl (S)-3-(3-(4-hydroxy-1,6-dimethyl-2-oxo-1,2-dihydropyridin-3-yl)ureido)-3-(5-(2-methylbenzyl)thiophen-2-yl)propanoate,
ethyl (S)-3-(3-(difluoro(o-tolyl)methyl)phenyl)-3-(3-(4-hydroxy-1-methyl-2-oxo-1,2-dihydropyridin-3-yl)ureido propanoate,
ethyl (S)-3-(3-(4-hydroxy-1-methyl-2-oxo-1,2-dihydropyridin-3-yl)ureido)-3-(3-phenoxyphenyl)propanoate,
ethyl (S)-3-(3-(4-hydroxy-1-methyl-2-oxo-1,2-dihydropyridin-3-yl)ureido)-3-(4-(2-methoxyphenoxy)phenyl)propanoate,
ethyl (S)-3-(3-(4-hydroxy-1-methyl-2-oxo-1,2-dihydropyridin-3-yl)ureido)-3-(4-(3-methoxyphenoxy)phenyl)propanoate,
ethyl (S)-3-(3-(4-hydroxy-1-methyl-2-oxo-1,2-dihydropyridin-3-yl)ureido)-3-(4-(0-tolyloxy)phenyl)propanoate,
ethyl (S)-3-(3-(4-hydroxy-1-methyl-2-oxo-1,2-dihydropyridin-3-yl)ureido)-3-(4-(p-tolyloxy)phenyl)propanoate,
ethyl (S)-3-(4-benzylphenyl)-3-(3-(4-hydroxy-1-methyl-2-oxo-1,2-dihydropyridin-3-yl)ureido)propanoate,
ethyl (S)-3-(3-(4-hydroxy-1-methyl-2-oxo-1,2-dihydropyridin-3-yl)ureido)-3-(4-(2-methylbenzyl)phenyl)propanoate,
ethyl (S)-3-(3-(4-hydroxy-1-methyl-2-oxo-1,2-dihydropyridin-3-yl)ureido)-3-(4-(3-methylbenzyl)phenyl)propanoate,
ethyl (S)-3-(3-(4-hydroxy-1-methyl-2-oxo-1,2-dihydropyridin-3-yl)ureido)-3-(4-(4-methylbenzyl)phenyl)propanoate,
ethyl (S)-3-(3-(2-ethylbenzyl)phenyl)phenyl)-(3-(4-hydroxy-1-methyl-2-oxo-1,2-dihydropyridin-3-yl)ureido)propanoate,
ethyl (S)-3-(3-(4-hydroxy-1-methyl-2-oxo-1,2-dihydropyridin-3-yl)ureido)-3-(3-(2-methylbenzyl)phenyl)propanoate,
ethyl (S)-3-(3-(4-hydroxy-1-methyl-2-oxo-1,2-dihydropyridin-3-yl)ureido)-3-(3-(3-methylbenzyl)phenyl)propanoate,
ethyl (S)-3-(3-(4-hydroxy-1-methyl-2-oxo-1,2-dihydropyridin-3-yl)ureido)-3-(3-(4-methylbenzyl)phenyl)propanoate,
ethyl (S)-3-(3-(4-hydroxy-1-methyl-2-oxo-1,2-dihydropyridin-3-yl)ureido)-3-(3-(2-(trifluoromethyl)benzyl)phenyl)propanoate,
ethyl (S)-3-(3-(4-hydroxy-1-methyl-2-oxo-1,2-dihydropyridin-3-yl)ureido)-3-(3-(3-(trifluoromethyl)benzyl)phenyl)propanoate,
ethyl (S)-3-(3-(4-hydroxy-1-methyl-2-oxo-1,2-dihydropyridin-3-yl)ureido)-3-(3-(4-(trifluoromethyl)benzyl)phenyl)propanoate,
ethyl (S)-3-(3-(2-(difluoromethoxy)benzyl)phenyl)-3-(3-(4-hydroxy-1-methyl-2-oxo-1,2-dihydropyridin-3-yl)ureido)propanoate,
ethyl (S)-3-(3-(4-hydroxy-1-methyl-2-oxo-1,2-dihydropyridin-3-yl)ureido)-3-(3-(2-methoxybenzyl)phenyl)propanoate,
ethyl (S)-3-(3-(2-fluorobenzyl)phenyl)-3-(3-(4-hydroxy-1-methyl-2-oxo-1,2-dihydropyridin-3-yl)ureido)propanoate,
ethyl (S)-3-(3-(2,6-dimethylbenzyl)phenyl)-3-(3-(4-hydroxy-1-methyl-2-oxo-1,2-dihydropyridin-3-yl)ureido)propanoate,
ethyl (S)-3-(3-(5-fluoro-2-methyl benzyl)phenyl)-3-(3-(4-hydroxy-1-methyl-2-oxo-1,2-dihydropyridin-3-yl)ureido)propanoate,
ethyl (S)-3-(3-(4-hydroxy-1-methyl-2-oxo-1,2-dihydropyridin-3-yl)ureido)-3-(5-(2-methylbenzyl)thiophen-2-yl)propanoate,
ethyl (S)-3-(5-benzylthiophen-2-yl)-3-(3-(4-hydroxy-1-methyl-2-oxo-1,2-dihydropyridin-3-yl)ureido)propanoate,
ethyl (S)-3-(3-(4-hydroxy-1-methyl-2-oxo-1,2-dihydropyridin-3-yl)ureido)-3-(3-(0-tolyloxy)phenyl)propanoate,
ethyl (S)-3-(3-(4-hydroxy-1-methyl-2-oxo-1,2-dihydropyridin-3-yl)ureido)-3-(3-(m-tolyloxy)phenyl)propanoate,
ethyl (S)-3-(3-(4-hydroxy-1-methyl-2-oxo-1,2-dihydropyridin-3-yl)ureido)-3-(3-(ptolyloxy)phenyl)propanoate,
ethyl (S)-3-(3-(4-hydroxy-1-methyl-2-oxo-1,2-dihydropyridin-3-yl)ureido)-3-(3-(2-methoxyphenoxy)phenyl)propanoate,
ethyl (S)-3-(3-(2-chlorophenoxy)phenyl)-3-(3-(4-hydroxy-1-methyl-2-oxo-1,2-dihydropyridin-3-yl)ureido)propanoate,
ethyl (S)-3-(3-(2,4-difluorophenoxy)phenyl)-3-(3-(4-hydroxy-1-methyl-2-oxo-1,2-dihydropyridin-3-yl)ureido)propanoate,
ethyl (S)-3-(3-(2,6-dimethylphenoxy)phenyl)-3-(3-(4-hydroxy-1-methyl-2-oxo-1,2-dihydropyridin-3-yl)ureido)propanoate,
3-(3-(4-hydroxy-1,5-dimethyl-2-oxo-1,2-dihydropyridin-3-yl)ureido)-3-(3-phenoxyphenyl)propanoic acid,
(S)-3-(3-(4-hydroxy-1,5-dimethyl-2-oxo-1,2-dihydropyridin-3-yl)ureido)-3-(3-phenoxyphenyl)propanoic acid,
(S)-3-(3-benzylphenyl)-3-(3-(4-hydroxy-1,5-dimethyl-2-oxo-1,2-dihydropyridin-3-yl)ureido)propanoic acid,
3-(3-(2-chlorobenzyl)phenyl)-3-(3-(4-hydroxy-1,5-dimethyl-2-oxo-1,2-dihydropyridin-3-yl)ureido)propanoic acid, 3-(3-(3-chlorobenzyl)phenyl)-3-(3-(4-hydroxy-1,5-dimethyl-2-oxo-1,2-dihydropyridin-3-yl)ureido)propanoic acid, 3-(3-(4-chlorobenzyl)phenyl)-3-(3-(4-hydroxy-1,5-dimethyl-2-oxo-1,2-dihydropyridin-3-yl)ureido)propanoic acid, (S)-3-(4-(2-chlorobenzyl)phenyl)-3-(3-(4-hydroxy-1,5-dimethyl-2-oxo-1,2-dihydropyridin-3-yl)ureido)propanoic acid, (S)-3-(3-(4-hydroxy-1,5-dimethyl-2-oxo-1,2-dihydropyridin-3-yl)ureido)-3-(3-(2-methylbenzyl)phenyl)propanoic acid, (S)-3-(3-(4-hydroxy-1,5-dimethyl-2-oxo-1,2-dihydropyridin-3-yl)ureido)-3-(3-(3-methylbenzyl)phenyl)propanoic acid, (S)-3-(3-(4-hydroxy-1,5-dimethyl-2-oxo-1,2-dihydropyridin-3-yl)ureido)-3-(3-(4-methylbenzyl)phenyl)propanoic acid, (S)-3-(3-(4-hydroxy-1,6-dimethyl-2-oxo-1,2-dihydropyridin-3-yl)ureido)-3-(4-(2-methoxyphenoxy)phenyl)propanoic acid, (S)-3-(3-(4-hydroxy-1,6-dimethyl-2-oxo-1,2-dihydropyridin-3-yl)ureido)-3-(4-(3-methoxyphenoxy)phenyl)propanoic acid, (S)-3-(3-(4-hydroxy-1,6-dimethyl-2-oxo-1,2-dihydropyridin-3-yl)ureido)-3-(3-(ptolyloxy)phenyl)propanoic acid, (S)-3-(3-(4-hydroxy-1,6-dimethyl-2-oxo-1,2-dihydropyridin-3-yl)ureido)-3-(3-(2-methylbenzyl)phenyl)propanoic acid, (S)-3-(3-(4-hydroxy-1,6-dimethyl-2-oxo-1,2-dihydropyridin-3-yl)ureido)-3-(5-(2-methylbenzyl)thiophen-2-yl)propanoic acid, (S)-3-(3-(difluoro(o-tolyl)methyl)phenyl)-3-(3-(4-hydroxy-1-methyl-2-oxo-1,2-dihydropyridin-3-yl)ureido)propanoic acid, (S)-3-(3-(4-hydroxy-1-methyl-2-oxo-1,2-dihydropyridin-3-yl)ureido)-3-(3-phenoxyphenyl)propanoic acid, (S)-3-(3-(4-hydroxy-1-methyl-2-oxo-1,2-dihydropyridin-3-yl)ureido)-3-(4-(2-methoxyphenoxy)phenyl)propanoic acid, (S)-3-(3-(4-hydroxy-1-methyl-2-oxo-1,2-dihydropyridin-3-yl)ureido)-3-(4-(3-methoxyphenoxy)phenyl)propanoic acid, (S)-3-(3-(4-hydroxy-1-methyl-2-oxo-1,2-dihydropyridin-3-yl)ureido)-3-(4-(0-tolyloxy)phenyl)propanoic acid, (S)-3-(3-(4-hydroxy-1-methyl-2-oxo-1,2-dihydropyridin-3-yl)ureido)-3-(4-(p-tolyloxy)phenyl)propanoic acid, (S)-3-(4-benzylphenyl)-3-(3-(4-hydroxy-1-methyl-2-oxo-1,2-dihydropyridin-3-yl)ureido)propanoic acid, (S)-3-(3-(4-hydroxy-1-methyl-2-oxo-1,2-dihydropyridin-3-yl)ureido)-3-(4-(2-methylbenzyl)phenyl)propanoic acid, (S)-3-(3-(4-hydroxy-1-methyl-2-oxo-1,2-dihydropyridin-3-yl)ureido)-3-(4-(3-methylbenzyl)phenyl)propanoic acid, (S)-3-(3-(4-hydroxy-1-methyl-2-oxo-1,2-dihydropyridin-3-yl)ureido)-3-(4-(4-methylbenzyl)phenyl)propanoic acid, (S)-3-(3-(2-ethylbenzyl)phenyl)phenyl)-(3-(4-hydroxy-1-methyl-2-oxo-1,2-dihydropyridin-3-yl)ureido)propanoic acid, (S)-3-(3-(4-hydroxy-1-methyl-2-oxo-1,2-dihydropyridin-3-yl)ureido)-3-(3-(2-methylbenzyl)phenyl)propanoic acid, (S)-3-(3-(4-hydroxy-1-methyl-2-oxo-1,2-dihydropyridin-3-yl)ureido)-3-(3-(3-methylbenzyl)phenyl)propanoic acid, (S)-3-(3-(4-hydroxy-1-methyl-2-oxo-1,2-dihydropyridin-3-yl)ureido)-3-(3-(4-methylbenzyl)phenyl)propanoic acid, (S)-3-(3-(4-hydroxy-1-methyl-2-oxo-1,2-dihydropyridin-3-yl)ureido)-3-(3-(2-(trifluoromethyl)benzyl)phenyl)propanoic acid, (S)-3-(3-(4-hydroxy-1-methyl-2-oxo-1,2-dihydropyridin-3-yl)ureido)-3-(3-(3-(trifluoromethyl)benzyl)phenyl)propanoic acid, (S)-3-(3-(4-hydroxy-1-methyl-2-oxo-1,2-dihydropyridin-3-yl)ureido)-3-(3-(4-(trifluoromethyl)benzyl)phenyl)propanoic acid, (S)-3-(3-(2-(difluoromethoxy)benzyl)phenyl)-3-(3-(4-hydroxy-1-methyl-2-oxo-1,2-dihydropyridin-3-yl)ureido)propanoic acid, (S)-3-(3-(4-hydroxy-1-methyl-2-oxo-1,2-dihydropyridin-3-yl)ureido)-3-(3-(2-methoxybenzyl)phenyl)propanoic acid, (S)-3-(3-(2-fluorobenzyl)phenyl)-3-(3-(4-hydroxy-1-methyl-2-oxo-1,2-dihydropyridin-3-yl)ureido)propanoic acid, (S)-3-(3-(2,6-dimethylbenzyl)phenyl)-3-(3-(4-hydroxy-1-methyl-2-oxo-1,2-dihydropyridin-3-yl)ureido)propanoic acid, (S)-3-(3-(5-fluoro-2-methylbenzyl)phenyl)-3-(3-(4-hydroxy-1-methyl-2-oxo-1,2-dihydropyridin-3-yl)ureido)propanoic acid, (S)-3-(3-(4-hydroxy-1-methyl-2-oxo-1,2-dihydropyridin-3-yl)ureido)-3-(5-(2-methylbenzyl)thiophen-2-yl)propanoic acid, (S)-3-(5-benzylthiophen-2-yl)-3-(3-(4-hydroxy-1-methyl-2-oxo-1,2-dihydropyridin-3-yl)ureido)propanoic acid, (S)-3-(3-(4-hydroxy-1-methyl-2-oxo-1,2-dihydropyridin-3-yl)ureido)-3-(3-(o-tolyloxy)phenyl)propanoic acid, (S)-3-(3-(4-hydroxy-1-methyl-2-oxo-1,2-dihydropyridin-3-yl)ureido)-3-(3-(m-tolyloxy)phenyl)propanoic acid, (S)-3-(3-(4-hydroxy-1-methyl-2-oxo-1,2-dihydropyridin-3-yl)ureido)-3-(3-(p-tolyloxy)phenyl)propanoic acid, (S)-3-(3-(4-hydroxy-1-methyl-2-oxo-1,2-dihydropyridin-3-yl)ureido)-3-(3-(2-methoxyphenoxy)phenyl)propanoic acid, (S)-3-(3-(2-chlorophenoxy)phenyl)-3-(3-(4-hydroxy-1-methyl-2-oxo-1,2-dihydropyridin-3-yl)ureido)propanoic acid, (S)-3-(3-(2,4-difluorophenoxy)phenyl)-3-(3-(4-hydroxy-1-methyl-2-oxo-1,2-dihydropyridin-3-yl)ureido)propanoic acid, (S)-3-(3-(2,6-dimethylphenoxy)phenyl)-3-(3-(4-hydroxy-1-methyl-2-oxo-1,2-dihydropyridin-3-yl)ureido)propanoic acid, sodium 3-(3-(1,5-dimethyl-4-oxido-2-oxo-1,2-dihydropyridin-3-yl)ureido)-3-(3-phenoxyphenyl)propanoate, sodium (S)-3-(3-benzylphenyl)-3-(3-(1,5-dimethyl-4-oxido-2-oxo-1,2-dihydropyridin-3-yl)ureido)propanoate, sodium 3-(3-(2-chlorobenzyl)phenyl)-3-(3-(1,5-dimethyl-4-oxido-2-oxo-1,2-dihydropyridin-3-yl)ureido)propanoate, sodium 3-(3-(3-chlorobenzyl)phenyl)-3-(3-(1,5-dimethyl-4-oxido-2-oxo-1,2-dihydropyridin-3-yl)ureido)propanoate, sodium 3-(3-(4-chlorobenzyl)phenyl)-3-(3-(1,5-dimethyl-4-oxido-2-oxo-1,2-dihydropyridin-3-yl)ureido) propanoate, sodium 3-(4-(2-chlorobenzyl)phenyl)-3-(3-(1,5-dimethyl-4-oxido-2-oxo-1,2-dihydropyridin-3-yl)ureido) propante, sodium (S)-3-(3-(1,5-dimethyl-4-oxido-2-oxo-1,2-dihydropyridin-3-yl)ureido)-3-(3-(2-methylbenzyl)phenyl) propanoate, sodium (S)-3-(3-(1,5-dimethyl-4-oxido-2-oxo-1,2-dihydropyridin-3-yl)ureido)-3-(3-(3-methylbenzyl)phenyl) propanoate, sodium (S)-3-(3-(1,5-dimethyl-4-oxido-2-oxo-1,2-dihydropyridin-3-yl)ureido)-3-(3-(4-methylbenzyl)phenyl) propanoate, sodium (S)-3-(3-(1,6-dimethyl-4-oxido-2-oxo-1,2-dihydropyridin-3-yl)ureido)-3-(4-(2-methoxyphenoxy)phenyl)propanoate, sodium (S)-3-(3-(1,6-dimethyl-4-oxido-2-oxo-1,2-dihydropyridin-3-yl)ureido)-3-(4-(3-methoxyphenoxy)phenyl)propanoate, sodium (S)-3-(3-(1,6-dimethyl-4-oxido-2-oxo-1,2-dihydropyridin-3-yl)ureido)-3-(3-(p-tolyloxy)phenyl)propanoate, sodium (S)-3-(3-(1,6-dimethyl-4-oxido-2-oxo-1,2-dihydropyridin-3-yl)ureido)-3-(3-(2-methylbenzyl)phenyl) propanoate, sodium (S)-3-(3-(1,6-dimethyl-4-oxido-2-oxo-1,2-dihydropyridin-3-yl)ureido)-3-(5-(2-methylbenzyl)thiophen-2-yl)propanoate, sodium (S)-3-(3-(difluoro(o-tolyl)methyl)phenyl)-3-(3-(1-methyl-4-oxido-2-oxo-1,2-dihydropyridin-3-yl)ureido), sodium (S)-3-(3-(1-methyl-4-oxido-2-oxo-1,2-dihydropyridin-3-yl)ureido)-3-(3-(0-tolyloxy)phenyl)propanoate, sodium (S)-3-(3-(2-methoxyphenoxy)phenyl)-3-(3-(1-methyl-4-oxido-2-oxo-1,2-dihydropyridin-3-yl)ureido) propanoate, sodium (S)-3-(3-(2-chlorophenoxy)phenyl)-3-(3-(1-methyl-4-oxido-2-oxo-1,2-dihydropyridin-3-yl)ureido) propanoate, sodium (S)-3-(3-(5-fluoro-2-methylbenzyl)phenyl)-3-(3-(1-methyl-4-oxido-2-oxo-1,2-dihydropyridin-3-yl) ureido)propanoate, sodium (S)-3-(3-(1-methyl-4-oxido-2-oxo-1,2-dihydropyridin-3-yl)ureido)-3-(3-phenoxyphenyl)propanoate, sodium (S)-3-(4-(2-methoxyphenoxy)phenyl)-3-(3-(1-methyl-4-oxido-2-oxo-1,2-dihyropriddin-3-yl)ureido) propanoate, sodium (S)-3-(4-(3-methoxyphenoxy)phenyl)-3-(3-(1-methyl-4-oxido-2-oxo-1,2-dihydropyridin-3-yl)ureido) propanoate, sodium (S)-3-(3-(1-methyl-4-oxido-2-oxo-1,2-dihydropyridin-3-yl)ureido)-3-(4-(0-tolyloxy)phenyl)propanoate, sodium (S)-3-(3-(1-methyl-4-oxido-2-oxo-1,2-dihydropyridin-3-yl)ureido)-3-(4-(p-tolyloxy)phenyl)propanoate, sodium (S)-3-(4-benzylphenyl)-3-(3-(1-methyl-4-oxido-2-oxo-1,2-dihydropyridin-3-yl)ureido)propanoate, sodium (S)-3-(3-(1-methyl-4-oxido-2-oxo-1,2-dihydropyridin-3-yl)ureido)-3-(4-(2-methylbenzyl)phenyl) propanoate, sodium (S)-3-(3-(1-methyl-4-oxido-2-oxo-1,2-dihydropyridin-3-yl)ureido)-3-(4-(3-methylbenzyl)phenyl) propanoate, sodium (S)-3-(3-(1-methyl-4-oxido-2-oxo-1,2-dihydropyridin-3-yl)ureido)-3-(4-(4-methylbenzyl)phenyl) propanoate, sodium (S)-3-(3-(2-ethylbenzyl)phenyl)-3-(3-(1-methyl-4-oxido-2-oxo-1,2-dihydropyridin-3-yl)ureido)propanoate, sodium (S)-3-(3-(1-methyl-4-oxido-2-oxo-1,2-dihydropyridin-3-yl)ureido)-3-(3-(2-methylbenzyl)phenyl) propanoate, sodium (S)-3-(3-(1-methyl-4-oxido-2-oxo-1,2-dihydropyridin-3-yl)ureido)-3-(3-(4-methylbenzyl)phenyl) propanoate, sodium (S)-3-(3-(1-methyl-4-oxido-2-oxo-1,2-dihydropyridin-3-yl)ureido)-3-(3-(mtolyloxy)phenyl)propanoate, sodium (S)-3-(3-(1-methyl-4-oxido-2-oxo-1,2-dihydropyridin-3-yl)ureido)-3-(3-(ptolyloxy)phenyl)propanoate, sodium (S)-3-(3-(2,4-difluorophenoxy)phenyl)-3-(3-(1-methyl-4-oxido-2-oxo-1,2-dihydropyridin-3-yl)ureido) propanoate, sodium (S)-3-(3-(2,6-dimethylphenoxy)phenyl)-3-(3-(1-methyl-4-oxido-2-oxo-1,2-dihydropyridin-3-yl)ureido) propanoate, sodium (S)-3-(3-(1-methyl-4-oxido-2-oxo-1,2-dihydropyridin-3-yl)ureido)-3-(3-(2-(trifluoromethyl)benzyl) phenyl)propanoate, sodium (S)-3-(3-(1-methyl-4-oxido-2-oxo-1,2-dihydropyridin-3-yl)ureido)-3-(3-(3-(trifluoromethyl)benzyl) phenyl)propanoate, sodium (S)-3-(3-(1-methyl-4-oxido-2-oxo-1,2-dihydropyridin-3-yl)ureido)-3-(3-(4-(trifluoromethyl)benzyl) phenyl)propanoate, sodium (S)-3-(3-(2-(difluoromethoxy)benzyl)phenyl)-3-(3-(1-methyl-4-oxido-2-oxo-1,2-dihydropyridin-3-yl) ureido)propanoate, sodium (S)-3-(3-(2-methoxybenzyl)phenyl)-3-(3-(1-methyl-4-oxido-2-oxo-1,2-dihydropyridin-3-yl)ureido) propanoate, sodium (S)-3-(3-(2-fluorobenzyl)phenyl)-3-(3-(1-methyl-4-oxido-2-oxo-1,2-dihydropyridin-3-yl)ureido)propanoate, sodium (S)-3-(3-(2,6-dimethylbenzyl)phenyl)-3-(3-(1-methyl-4-oxido-2-oxo-1,2-dihydropyridin-3-yl)ureido) propanoate, sodium (S)-3-(3-(1-methyl-4-oxido-2-oxo-1,2-dihydropyridin-3-yl)ureido)-3-(5-(2-methylbenzyl)thiophen-2-yl)propanoate, sodium (S)-3-(5-benzylthiophen-2-yl)-3-(3-(1-methyl-4-oxido-2-oxo-1,2-dihydropyridin-3-yl)ureido)propanoate.

* * * * *